US009012223B2

(12) United States Patent
Ko et al.

(10) Patent No.: US 9,012,223 B2
(45) Date of Patent: Apr. 21, 2015

(54) METHODS FOR ENHANCING GENOME STABILITY AND TELOMERE ELONGATION IN EMBRYONIC STEM CELLS

(71) Applicant: The United States of America, as represented by the Secretary, Department of Health and Human Services, Washington, DC (US)

(72) Inventors: Minoru S. H. Ko, Tokyo (JP); Michal Zalzman, Baltimore, MD (US); Lioudmila V. Sharova, Pasadena, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/259,600

(22) Filed: Apr. 23, 2014

(65) Prior Publication Data
US 2014/0234969 A1   Aug. 21, 2014

Related U.S. Application Data

(63) Continuation of application No. 13/393,456, filed as application No. PCT/US2010/047644 on Sep. 2, 2010, now Pat. No. 8,741,649.

(60) Provisional application No. 61/275,983, filed on Sep. 4, 2009.

(51) Int. Cl.
| C12N 15/00 | (2006.01) |
| C12N 15/86 | (2006.01) |
| C12N 5/07 | (2010.01) |
| C12N 5/10 | (2006.01) |
| C12N 5/02 | (2006.01) |
| C12N 15/85 | (2006.01) |
| C07K 14/47 | (2006.01) |
| C12N 5/0735 | (2010.01) |
| C12N 5/00 | (2006.01) |

(52) U.S. Cl.
CPC ............ *C12N 15/85* (2013.01); *C07K 14/4705* (2013.01); *C12N 5/0606* (2013.01); *C12N 2501/40* (2013.01); *C12N 2501/60* (2013.01); *C12N 2501/00* (2013.01); *C12N 5/00* (2013.01); *C12N 15/00* (2013.01); *C12N 15/86* (2013.01)

(58) Field of Classification Search
USPC ......................................................... 435/455
See application file for complete search history.

(56) References Cited

U.S. PATENT DOCUMENTS

| 5,226,914 A | 7/1993 | Caplan et al. |
| 5,670,372 A | 9/1997 | Hogan |
| 5,750,376 A | 5/1998 | Weiss et al. |
| 6,090,622 A | 7/2000 | Gearhart et al. |
| 6,200,806 B1 | 3/2001 | Thomson |
| 6,506,559 B1 | 1/2003 | Fire et al. |
| 6,943,241 B2 | 9/2005 | Isogai et al. |
| 2005/0042748 A1 | 2/2005 | Ochiya et al. |
| 2006/0251642 A1 | 11/2006 | Wolffe et al. |
| 2009/0068742 A1 | 3/2009 | Yamanaka |

FOREIGN PATENT DOCUMENTS

| WO | WO 00/27995 | 5/2000 |
| WO | WO 00/70021 | 11/2000 |
| WO | WO 02/096203 | 12/2002 |
| WO | WO 2006/052646 | 5/2006 |
| WO | WO 2006/126972 | 11/2006 |
| WO | WO 2007/069666 | 6/2007 |
| WO | WO 2007/098047 | 8/2007 |
| WO | WO 2007/102787 | 9/2007 |
| WO | WO 2007/141657 | 12/2007 |
| WO | WO 2008/118957 | 10/2008 |
| WO | WO 2009/047568 | 4/2009 |

OTHER PUBLICATIONS

Chin, 2009, Cell Stem Cell, 5:111-123.*
International Search Report from PCT/US2008/058261, dated Jan. 19, 2009.
Written Opinion of the International Searching Authority from PCT/US2008/058261, dated, Jan. 19, 2009.
International Search Report from PCT/US2010/047644, dated May 2, 2011.
Written Opinion of the International Searching Authority from PCT/US2010/047644, dated, May 2, 2011.
Andrews et al., "Embryonic stem (ES) cells and embryonal carcinoma (EC) cells: opposite sides of the same coin," *Biochem Soc Trans* 33(Pt6):1526-1530, 2005.
Database Geneseq [Online], "Viral vector-related plasmid—pcDNA6.2/GFP-DEST." XP002492234 retrieved from EBI accession No. GSN:ADQ48564 Database accession No. ADQ48564, Sep. 9, 2004.

(Continued)

*Primary Examiner* — Valarie Bertoglio
(74) *Attorney, Agent, or Firm* — Klarquist Sparkman, LLP

(57) ABSTRACT

The disclosure provides methods for increasing genome stability of an embryonic stem (ES) cell or induced pluripotent stem (iPS) cell, increasing telomere length in an ES or iPS cell, or both, for example by contacting an ES or iPS cell with an agent that increases expression of Zscan4 in the cell. Methods for increasing genome stability or increasing telomere length in a population of ES or iPS cells are provided, for example by selecting Zscan4+ ES or iPS cells from the population of ES or iPS cells (which can include both Zscan4+ and Zscan4− ES or iPS cells). Therapeutic methods of using ES or iPS cells expressing Zscan4 are also provided. Further provided are methods of treating cancer by administering a Zscan4 polynucleotide or Zscan4 polypeptide. Also provided are methods of inducing differentiation of isolated ES or iPS cells into germ cells.

12 Claims, 42 Drawing Sheets

(56) References Cited

OTHER PUBLICATIONS

Carter et al., "An in situ hybridization-based screen for heterogeneously expressed genes in mouse ES cells," *Gene Expression Patterns* 8(3):181-198, Nov. 4, 2007.
Chambers et al., "Functional Expression Cloning of Nanog, a Pluripotency Sustaining Factor in Embryonic Stem Cells," *Cell* 113:643-655, 2003.
Dahéron et al., "LIF/STAT3 Signaling Fails to Maintain Self-Renewal of Human Embryonic Stem Cells," *Stem Cells* 22:770-778, 2004.
Edelstein et al., "The SCAN domain family of zinc finger transcription factors," *Gene* 359:1-1, Oct. 10, 2005.
Falco, "Zgal, a 2-cell Specific Gene Required for 2-cell to 4-cell Progression in Mouse Preimplantation Embryos," PowerPoint presentation from the Annual Meeting of the Society for the Study of Reproduction, Jul. 24-27, 2005.
Falco et al., "Identification and Characterization of Zygotic Genomic Activation Gene 1 (Zgal) in Mouse," Abstract from the Annual Meeting of the Society for the Study of Reproduction, Jul. 24-27, 2005.
Falco et al., "Zscan4: A novel gene expressed exclusively in late 2-cell embryos and embryonic stem cells," *Dev. Biol.*, vol. 307:539-550, 2007.
Falco et al., "Use of Chuk as an internal standard suitable for quantitative RT-PCR in mouse preimplantation embryos," *Reprod Biomed Online* 13(3):394-403, 2006.
Gerhard et al., "The status, quality, and expansion of the NIH full-length cDNA project: the Mammalian Gene Collection (MGC)," *Genome Res* 14:2121-2127, 2004.
Ginis et al., "Differences between human and mouse embryonic stem cells," *Dev Biol* 269:360-380, 2004.
Hanna et al., "Metastable Pluripotent States in NOD-Mouse-Derived ESCs," *Cell Stem Cell*, vol. 4:513-524, 2009.
Hanna et al., "Human Embryonic Stem Cells with Biological and Epigenetic Characteristics Similar to those of Mouse ESCs," *Proc. Nat. Acad. Sci. USA*, vol. 107:9222-9227, 2010.
Huminiecki et al., "Divergence of Spatial Gene Expression Profiles Following Species-Specific Gene Duplications in Human and Mouse," *Genome Res.*, vol. 14:1870-1879, 2004.
Humphrey et al., "Maintenance of Pluripotency in Human Embryonic Stem Cells is STAT3 Independent," *Stem Cells* 22:522-530, 2004.
Koestenbauer et al., "Embryonic Stem Cells: Similarities and Differences Between Human and Murine Embryonic Stem Cells," *Am J Reprod Immunol* 55(3):169-180, 2006.
Ota et al., "Complete sequencing and characterization of 21,243 full-length human cDNAs," *Nat Genet* 36(1):40-45, 2004.
Romano, "Gene Transfer in Experimental Medicine," *Drug News Prospect* 16(5):267-276, 2003.
Sato et al., "Maintenance of pluripotency in human and mouse embryonic stem cells through activation of Wnt signaling by a pharmacological GSK-3-specific inhibitor," *Nat Med* 10:55-63, 2004.
Sharov et al., "Transcriptome analysis of mouse stem cells and early embryos," *PLoS Bio* 1(3):410-419, 2003.
Storm et al., "Characterization of the phosphoinositide 3-kinase-dependent transcriptome in murine embryonic stem cells: identification of novel regulator of pluripotency," *Stem Cells* 27(4):764-765, 2009.
Strausberg et al., "Generation and initial analysis of more than 15,000 full-length human and mouse cDNA sequences," *Proc Natl Acad Sci USA* 99(26):16899-16903, 2002.
Thomas et al., "Progress and Problems with the Use of Viral Vectors for Gene Therapy," *Nature Rev Genet* 4:346-358, 2004.
Verma and Weitzman, "Gene Therapy: Twenty-First Century Medicine," *Annu Rev Biochem* 74:711-738, 2005.
Zalzman et al., "Zscan4 regulates telomere elongation and genomic stability in ES cells," *Nature*, vol. 464: 858-863, 2010.
Zhang et al., "Zfp206 regulates ES cell gene expression and differentiation," *Nucleic Acids Research* 34(17):4780-4790, 2006.
GenBank Accession No. AK141250, Oct. 5, 2006.
Guenther et al., "Chromatin Structure and Gene Expression Programs of Human Embryonic and Induced Pluripotent Stem Cells," *Cell Stem Cell* 7(2):249-257, 2010.
Marion et al., "Telomeres Acquire Embryonic Stem Cell Characteristics in Induced Pluripotent Stem Cells," *Cell Stem Cell* 4:141-154, 2009.

* cited by examiner

FIG. 1J

| Gene Symbol | Annotation | GenBank No. | Fold change |
|---|---|---|---|
| Zscan4c | zinc finger and SCAN domain containing 4C | NM_001013765 | 127.9 |
| Tcstv3 | 2-cell-stage, variable group, member 3 | NM_153523 | 107.9 |
| Tcstv1 | 2-cell-stage, variable group, member 1 | NM_018756 | 60.0 |
| Tmem92 | transmembrane protein 92 | NM_001034896 | 40.7 |
| A530040E14Rik | RIKEN cDNA A530040E14 gene | AK163084 | 39.7 |
| Eif1a | eukaryotic translation initiation factor 1A | NM_010120 | 25.4 |
| Arg2 | arginase type II | NM_009705 | 24.9 |
| BC061212 | cDNA sequence BC061212 | NM_198667 | 21.9 |
| AF067063 | cDNA sequence AF067063 | NM_001001449 | 20.7 |
| EG627488 | predicted gene, EG627488 | XM_001004017 | 20.7 |
| Lgals4 | lectin, galactose binding, soluble 4 | NM_010706 | 16.2 |
| Drr2 | developmentally regulated repeat element-containing transcript 2 | U51726 | 14.4 |
| Pif1 | PIF1 5'-to-3' DNA helicase homolog (S. cerevisiae) | NM_172453 | 13.9 |
| EG667568 | predicted gene, EG667568 | BC158090 | 13.5 |
| 2310065F04Rik | RIKEN cDNA 2310065F04 gene | AK010044 | 10.5 |
| Gm428 | gene model 428, (NCBI) | NM_001081644 | 9.8 |
| Ly6h | lymphocyte antigen 6 complex, locus H | NM_001135688 | 9.2 |
| EG668777 | predicted gene, EG668777 | XM_001474936 | 9.1 |
| Calcoco2 | calcium binding and coiled-coil domain 2 | NM_001100177 | 9.0 |
| Myo3a | myosin IIIA | NM_148413 | 8.4 |

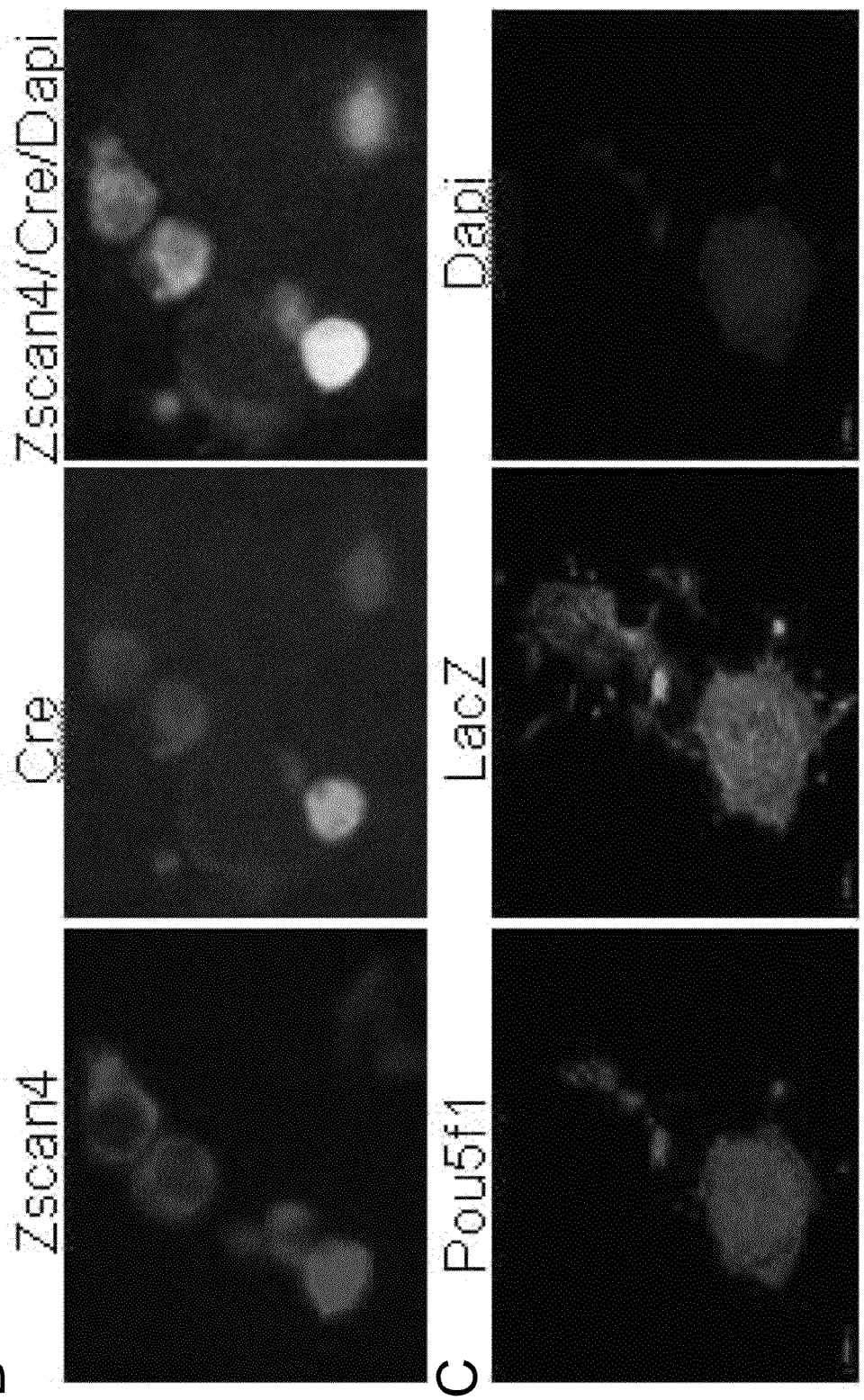

FIG. 4G

Karyotype Analysis to Zscan4 knockdown and rescue cells

| | Passage 3 | | | | Passage 10 | | | |
|---|---|---|---|---|---|---|---|---|
| | shRNA Control Dox+ | shRNA Control Dox- | Knock-down | Rescue | shRNA Control Dox+ | shRNA Control Dox- | Knock-down | Rescue |
| Fragmentations | 0 | 1 | 4 | 1 | 1 | 1 | 7 | 1 |
| Fusions | 2 | 1 | 7 | 2 | 2 | 1 | 7 | 4 |
| Centromere Fragments | 1 | 0 | 1 | 1 | 0 | 0 | 5 | 0 |
| Dicentric | 0 | 0 | 1 | 2 | 0 | 1 | 9 | 1 |
| Acentric | 0 | 0 | 1 | 0 | 1 | 0 | 1 | 0 |
| Chromosomes /metaphase | 39.75 | 40 | 39.75 | 39.8 | 39.56 | 39.78 | 39.65 | 39.68 |
| Total normal Karyotype (%) | 82.5% | 85% | 65% | 75% | 65% | 67.5% | 35% | 60% |
| Sum abnormal | 3 | 2 | 14 | 6 | 3 | 3 | 29 | 6 |

FIG. 6C
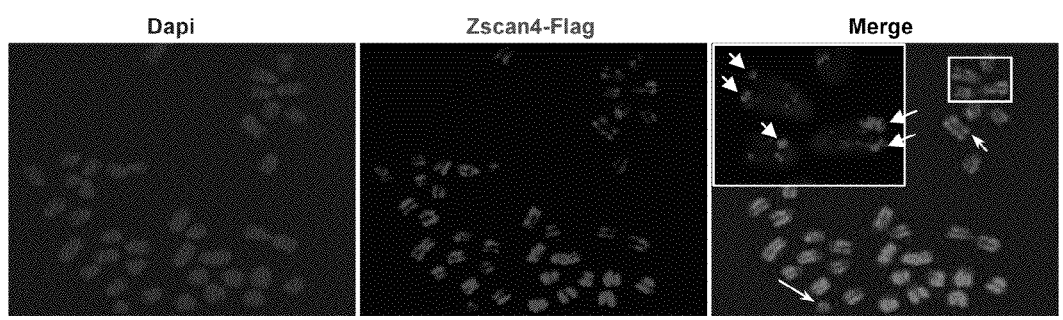
FIG. 6D
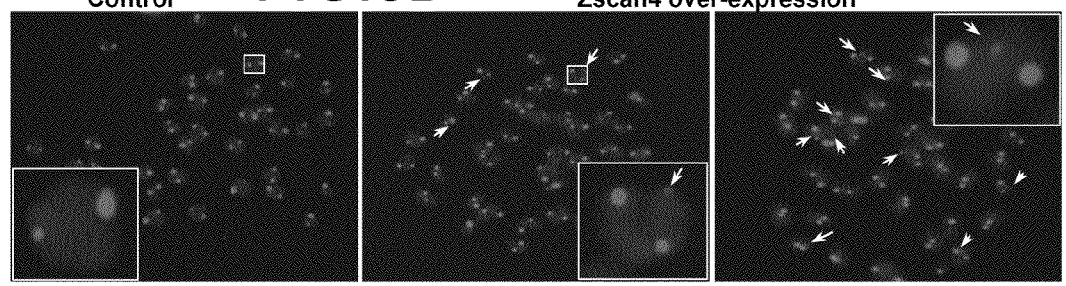
FIG. 6E
| | Empty Dox+ | Empty Dox- | Zscan4 Dox+ | Zscan4 Over-expression |
|---|---|---|---|---|
| Cells | 21 | 25 | 35 | 45 |
| Total No. of Chromosomes | 829 | 992 | 1150 | 1835 |
| Total No. of T-SCE | 4 | 6 | 9 | 134 |
| % cells with T-SCE | 19 | 20 | 17 | 76 |
| No. of T-SCE per cell | 0.19 | 0.24 | 0.26 | 2.97 |

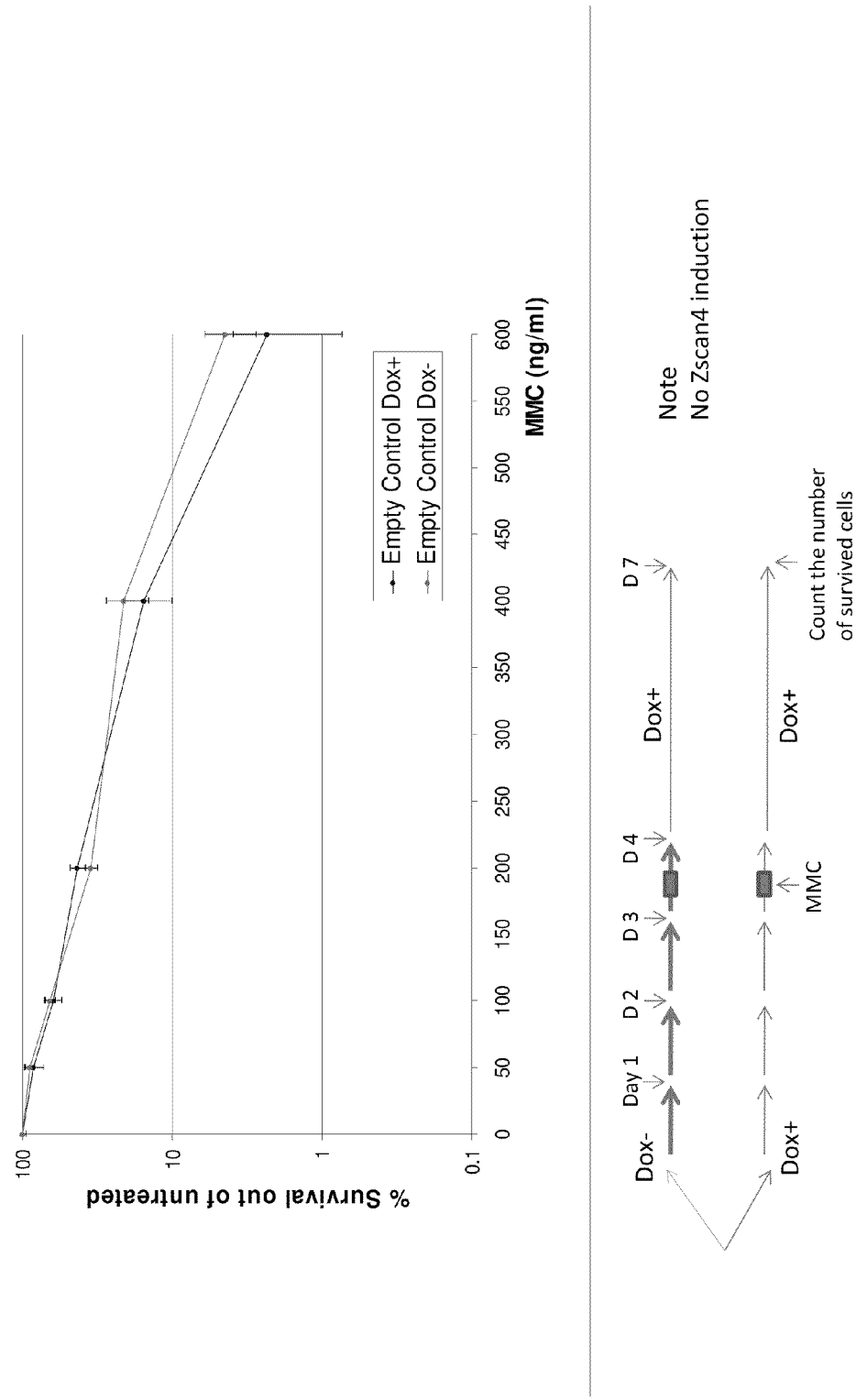

SEQUENCE LISTING

```
<160> NUMBER OF SEQ ID NOS: 39

<210> SEQ ID NO 1
<211> LENGTH: 21
<212> TYPE: DNA
<213> ORGANISM: Artificial Sequence
<220> FEATURE:
<223> OTHER INFORMATION: forward primer to amplify Zscan4 promoter

<400> SEQUENCE: 1
``` ggcaaccetta ctacttctat c        21

<210> SEQ ID NO 2
<211> LENGTH: 20
<212> TYPE: DNA
<213> ORGANISM: Artificial Sequence
<220> FEATURE:
<223> OTHER INFORMATION: reverse primer to amplify Zscan4 promoter

<400> SEQUENCE: 2
agcatcaacc actttggtac        20

<210> SEQ ID NO 3
<211> LENGTH: 22
<212> TYPE: DNA
<213> ORGANISM: Artificial Sequence
<220> FEATURE:
<223> OTHER INFORMATION: qPCR primer

<400> SEQUENCE: 3 tcagagggggg ccacaagtgt tc        22

<210> SEQ ID NO 4
<211> LENGTH: 22
<212> TYPE: DNA
<213> ORGANISM: Artificial Sequence
<220> FEATURE:
<223> OTHER INFORMATION: qPCR primer

<400> SEQUENCE: 4
cagaccaacc cttgccaagc tt        22

<210> SEQ ID NO 5
<211> LENGTH: 25
<212> TYPE: DNA
<213> ORGANISM: Artificial Sequence
<220> FEATURE:
<223> OTHER INFORMATION: qPCR primer

<400> SEQUENCE: 5
ccatgcaagg tgtccacttt ctcac        25

<210> SEQ ID NO 6
<211> LENGTH: 24
<212> TYPE: DNA
<213> ORGANISM: Artificial Sequence
<220> FEATURE:
<223> OTHER INFORMATION: qPCR primer

<400> SEQUENCE: 6
ggggtccctc tccatcactc acta        24

<210> SEQ ID NO 7
<211> LENGTH: 20
<212> TYPE: DNA
<213> ORGANISM: Artificial Sequence
<220> FEATURE:
<223> OTHER INFORMATION: qPCR primer

<400> SEQUENCE: 7
tgctcgtccg gctgtgacgg        20

<210> SEQ ID NO 8
<211> LENGTH: 24
<212> TYPE: DNA
<213> ORGANISM: Artificial Sequence

```
<220> FEATURE:
<223> OTHER INFORMATION: qPCR primer

<400> SEQUENCE: 8
gctctcagaa gccaggactc tgca                                          24

<210> SEQ ID NO 9
<211> LENGTH: 22
<212> TYPE: DNA
<213> ORGANISM: Artificial Sequence
<220> FEATURE:
<223> OTHER INFORMATION: qPCR primer

<400> SEQUENCE: 9
tgtacgagat cttgggccac cc                                            22

<210> SEQ ID NO 10
<211> LENGTH: 24
<212> TYPE: DNA
<213> ORGANISM: Artificial Sequence
<220> FEATURE:
<223> OTHER INFORMATION: qPCR primer

<400> SEQUENCE: 10
cacggtaacc caccagcttc ctat                                          24

<210> SEQ ID NO 11
<211> LENGTH: 22
<212> TYPE: DNA
<213> ORGANISM: Artificial Sequence
<220> FEATURE:
<223> OTHER INFORMATION: qPCR primer

<400> SEQUENCE: 11
atggacactt ggaggcagcc ag                                            22

<210> SEQ ID NO 12
<211> LENGTH: 22
<212> TYPE: DNA
<213> ORGANISM: Artificial Sequence
<220> FEATURE:
<223> OTHER INFORMATION: qPCR primer

<400> SEQUENCE: 12
gacgcccagc tggatgctta tc                                            22

<210> SEQ ID NO 13
<211> LENGTH: 20
<212> TYPE: DNA
<213> ORGANISM: Artificial Sequence
<220> FEATURE:
<223> OTHER INFORMATION: qPCR primer

<400> SEQUENCE: 13
agaccacagc ctggcaatag                                               20

<210> SEQ ID NO 14
<211> LENGTH: 20
<212> TYPE: DNA
<213> ORGANISM: Artificial Sequence
<220> FEATURE:
<223> OTHER INFORMATION: qPCR primer

<400> SEQUENCE: 14
aaggtaccac aactgccagg                                               20
```

```
<210> SEQ ID NO 15
<211> LENGTH: 28
<212> TYPE: DNA
<213> ORGANISM: Artificial Sequence
<220> FEATURE:
<223> OTHER INFORMATION: qPCR primer

<400> SEQUENCE: 15
tctccagctg ttgtggaata agttcaac                                        28

<210> SEQ ID NO 16
<211> LENGTH: 37
<212> TYPE: DNA
<213> ORGANISM: Artificial Sequence
<220> FEATURE:
<223> OTHER INFORMATION: qPCR primer

<400> SEQUENCE: 16
cttcttggct ttatccatgg atccctgaag gtaaatc                              37

<210> SEQ ID NO 17
<211> LENGTH: 21
<212> TYPE: DNA
<213> ORGANISM: Artificial Sequence
<220> FEATURE:
<223> OTHER INFORMATION: qPCR primer

<400> SEQUENCE: 17
cctccctggg cttcttggca t                                               21

<210> SEQ ID NO 18
<211> LENGTH: 24
<212> TYPE: DNA
<213> ORGANISM: Artificial Sequence
<220> FEATURE:
<223> OTHER INFORMATION: qPCR primer

<400> SEQUENCE: 18
agctgccaac cagaaagaca ctgt                                            24

<210> SEQ ID NO 19
<211> LENGTH: 24
<212> TYPE: DNA
<213> ORGANISM: Artificial Sequence
<220> FEATURE:
<223> OTHER INFORMATION: qPCR primer

<400> SEQUENCE: 19
caggaccgtg ttctcaagga gctg                                            24

<210> SEQ ID NO 20
<211> LENGTH: 24
<212> TYPE: DNA
<213> ORGANISM: Artificial Sequence
<220> FEATURE:
<223> OTHER INFORMATION: qPCR primer

<400> SEQUENCE: 20
gctctggtcc tcatttgctt cacg                                            24

<210> SEQ ID NO 21
<211> LENGTH: 83
<212> TYPE: DNA
<213> ORGANISM: Artificial Sequence
<220> FEATURE:
<223> OTHER INFORMATION: primer
```

<400> SEQUENCE: 21
cataacctga aaaaacagaa gcctggcatt ccctaagctt agggaatgcc aggcttctgc   60
gcgtcctttc acaagatat ata   83

<210> SEQ ID NO 22
<211> LENGTH: 83
<212> TYPE: DNA
<213> ORGANISM: Artificial Sequence
<220> FEATURE:
<223> OTHER INFORMATION: primer

<400> SEQUENCE: 22
cataacctga aaaaacagaa gcctggcatt ccctttcgaa agggaatgcc aggcttctgc   60
gcgtcctttc acaagatat ata   83

<210> SEQ ID NO 23
<211> LENGTH: 42
<212> TYPE: DNA
<213> ORGANISM: Artificial Sequence
<220> FEATURE:
<223> OTHER INFORMATION: nucleotide repeat used for CO-FISH analysis

<400> SEQUENCE: 23
ttagggttag ggttagggtt agggttaggg ttagggttag gg   42

<210> SEQ ID NO 24
<211> LENGTH: 2275
<212> TYPE: DNA
<213> ORGANISM: Mus musculus
<220> FEATURE:
<221> NAME/KEY: CDS
<222> LOCATION: (201)..(1280)

<400> SEQUENCE: 24
cacagtgcct ccctgggctt cttggcatca cccttgaagt tcactggaga aagagttgag   60
gtggaggaat aggtaaactt cccttcctag tggtcttgaa tgtcttttac agtacatcca   120
tcaactgtta gcattttcgt aaagtcacaa aacagatatt aaactactat agttgaatct   180
ttcacaccat tgtcaccaca atg gct tca cag cag gca cca gca aaa gac ctt   233
                        Met Ala Ser Gln Gln Ala Pro Ala Lys Asp Leu
                        1               5                   10 cag acc aac aat tta gag ttt act cca act gat agt tct ggt gtg cag   281
Gln Thr Asn Asn Leu Glu Phe Thr Pro Thr Asp Ser Ser Gly Val Gln
            15                  20                  25 tgg gca gaa gac atc tct aac tca cca agt gct cag cta aac ttt tcc   329
Trp Ala Glu Asp Ile Ser Asn Ser Pro Ser Ala Gln Leu Asn Phe Ser
        30                  35                  40 cca agt aac aat ggc tgc tgg gca act cag gag ctg caa agt ctc tgg   377
Pro Ser Asn Asn Gly Cys Trp Ala Thr Gln Glu Leu Gln Ser Leu Trp
    45                  50                  55 aag atg ttc aac tcc tgg ttg cag cca gaa aag cag act aag gag cag   425
Lys Met Phe Asn Ser Trp Leu Gln Pro Glu Lys Gln Thr Lys Glu Gln
60                  65                  70                  75 atg att tct caa ctg gtc ttg gag cag ttt ctc ctc act ggg cac tgc   473
Met Ile Ser Gln Leu Val Leu Glu Gln Phe Leu Leu Thr Gly His Cys
                80                  85                  90 aag gac aag tat gct ttg aca gag aag tgg aaa gcc agt ggt agc gat   521
Lys Asp Lys Tyr Ala Leu Thr Glu Lys Trp Lys Ala Ser Gly Ser Asp
            95                  100                 105 atg agg aga ttc atg gag agt ctg act gat gag tgc ttg aag cct cct   569

```
Met Arg Arg Phe Met Glu Ser Leu Thr Asp Glu Cys Leu Lys Pro Pro
            110                 115                 120 gtc atg gtc cat gtc tca atg caa gga caa gaa gcc ctc ttt tct gaa         617
Val Met Val His Val Ser Met Gln Gly Gln Glu Ala Leu Phe Ser Glu
    125                 130                 135 aac atg cca tta aaa gaa gtc atc aag ctt ttg aaa caa cag caa tct         665
Asn Met Pro Leu Lys Glu Val Ile Lys Leu Leu Lys Gln Gln Gln Ser
140                 145                 150                 155 gca aca agg cca aca cca gat aat gca cag atg cca gta gac acc aca         713
Ala Thr Arg Pro Thr Pro Asp Asn Ala Gln Met Pro Val Asp Thr Thr
                160                 165                 170 caa gat aga tta ttg gcc aca gga caa gaa aac agt gaa aat gaa tgc         761
Gln Asp Arg Leu Leu Ala Thr Gly Gln Glu Asn Ser Glu Asn Glu Cys
            175                 180                 185 aac acc tct tgt aat gct act gaa gga aat gtt ggt gag agc tgt agt         809
Asn Thr Ser Cys Asn Ala Thr Glu Gly Asn Val Gly Glu Ser Cys Ser
        190                 195                 200 gga aat gaa atg gac tcc tct ctt att atc cag aaa gaa cag tac cct         857
Gly Asn Glu Met Asp Ser Ser Leu Ile Ile Gln Lys Glu Gln Tyr Pro
205                 210                 215 gag cat gaa gag ggg aat gtt gtt tgt caa ttc cct ctt gat gcc aga         905
Glu His Glu Glu Gly Asn Val Val Cys Gln Phe Pro Leu Asp Ala Arg
220                 225                 230                 235 aga gca agt caa ggc acc tcc agt cat cat gta gac ttc ctg agt gct         953
Arg Ala Ser Gln Gly Thr Ser Ser His His Val Asp Phe Leu Ser Ala
            240                 245                 250 ctg act act gcc gat gtc ccc atg gag gaa caa cca aag gat tta tcc        1001
Leu Thr Thr Ala Asp Val Pro Met Glu Glu Gln Pro Lys Asp Leu Ser
        255                 260                 265 aga gaa aac atc tct gag gac aag aac aat tgc tat aac act tcc agg        1049
Arg Glu Asn Ile Ser Glu Asp Lys Asn Asn Cys Tyr Asn Thr Ser Arg
    270                 275                 280 aat gca gct act aaa gta tat agt ggt gat aat att ccc agg aaa aag        1097
Asn Ala Ala Thr Lys Val Tyr Ser Gly Asp Asn Ile Pro Arg Lys Lys
285                 290                 295 aca gac tcc ctt tcc att aac aag agg ata tat cat cct gag cct gag        1145
Thr Asp Ser Leu Ser Ile Asn Lys Arg Ile Tyr His Pro Glu Pro Glu
300                 305                 310                 315 gtg gga gat att cct tat gga gtt cct cag gat tct aca aga gca agt        1193
Val Gly Asp Ile Pro Tyr Gly Val Pro Gln Asp Ser Thr Arg Ala Ser
            320                 325                 330 caa gga aca tct aca tgc ctg caa gag tca ctt ggg gga tgt ttt tcc        1241
Gln Gly Thr Ser Thr Cys Leu Gln Glu Ser Leu Gly Gly Cys Phe Ser
        335                 340                 345 gaa aaa gac cct agg gag gta cca ggg ttg cag tct agg taagagcagc        1290
Glu Lys Asp Pro Arg Glu Val Pro Gly Leu Gln Ser Arg
350                 355                 360 ctatctctga tcctgtcctt cttggtaaga atcatgaggc aaacttacca tgtgaaagtc     1350
atcaaaagag attctgtaga gatgccaaac tatacaagtg tgaagaatgt tctaggatgt     1410
tcaaacatgc caggagcctt tcatcccacc agagaactca cctgaataag aagagtgaat     1470
tgctttgtgt cacctgtcag aaaattttca aacgagtctc tgaccgccga acccatgaga     1530
tcatacacat gccagaaaag cctttcaagt gcagcacatg tgaaaagtcc ttcagccaca     1590
agaccaacct gaagtctcat gagatgattc acacaggaga aatgccttat gtctgttccc     1650
tatgtagccg tcgctttcgc caatcatcca cttaccatcg tcacctgagg aattatcaca     1710
gatctgactg aagtatctaa catcctcagc agagactggt agggcttcag cctcagtatg     1770
```

-continued

```
tcatcttcaa agagagaaga atgttgcaag taaattgtac tgtcccaata atgatataac    1830
atgcttgtgg attgccactt ttatgttttg ttttgttttg ttttttattt tgtgtgtgtg    1890
tatgtaattt tttgtctgta tttccatagt tccacagcat aagttattag aatactttgc    1950
tgttaattct tgagttgctt cttgctttta gacagtgtct ttctggttgg cagctttata    2010
cacctgtctt tctggcacta gagtttccaa acatttctg atctccactt ttattttcta    2070
cagtggtcct gacagaggcc tgccattccc tctgacattt ttctacatgt tggggtttca    2130
tcccaagtct tagggttgca agttaaatgc attgcctctt cagacatctc atgtcatgtc    2190
tactgcttac agttcaagaa tatttctcta cattactaga acgacgttca aagtggaata    2250
ataaataaat aaataatcaa caatt                                         2275
```

<210> SEQ ID NO 25
<211> LENGTH: 360
<212> TYPE: PRT
<213> ORGANISM: Mus musculus

<400> SEQUENCE: 25

```
Met Ala Ser Gln Gln Ala Pro Ala Lys Asp Leu Gln Thr Asn Asn Leu
1               5                   10                  15

Glu Phe Thr Pro Thr Asp Ser Ser Val Gln Trp Ala Glu Asp Ile
            20                  25                  30

Ser Asn Ser Pro Ser Ala Gln Leu Asn Phe Ser Pro Ser Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Ala Gln Met Pro Val Asp Thr Thr Gln Asp Arg Leu Leu
                165                 170                 175

Ala Thr Gly Gln Glu Asn Ser Glu Asn Glu Cys Asn Thr Ser Cys Asn
            180                 185                 190

Ala Thr Glu Gly Asn Val Gly Glu Ser Cys Ser Gly Asn Glu Met Asp
        195                 200                 205

Ser Ser Leu Ile Ile Gln Lys Glu Gln Tyr Pro Glu His Glu Gly
    210                 215                 220

Asn Val Val Cys Gln Phe Pro Leu Asp Ala Arg Arg Ala Ser Gln Gly
225                 230                 235                 240

Thr Ser Ser His His Val Asp Phe Leu Ser Ala Leu Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Lys
        275                 280                 285
```

```
Val Tyr Ser Gly Asp Asn Ile Pro Arg Lys Lys Thr Asp Ser Leu Ser
        290                 295                 300
Ile Asn Lys Arg Ile Tyr His Pro Glu Pro Glu Val Gly Asp Ile Pro
305                 310                 315                 320
Tyr Gly Val Pro Gln Asp Ser Thr Arg Ala Ser Gln Gly Thr Ser Thr
                325                 330                 335
Cys Leu Gln Glu Ser Leu Gly Gly Cys Phe Ser Glu Lys Asp Pro Arg
            340                 345                 350
Glu Val Pro Gly Leu Gln Ser Arg
            355                 360

<210> SEQ ID NO 26
<211> LENGTH: 1774
<212> TYPE: DNA
<213> ORGANISM: Mus musculus
<220> FEATURE:
<221> NAME/KEY: CDS
<222> LOCATION: (201)..(788)

<400> SEQUENCE: 26
```

| | | |
|---|---|---|
| cacagtgcct ccctgggctt cttggcatca cccttgaagt tcactggaga aagaggtgat | | 60 |
| gtggagaagt aggtaaactt ccctttcttg tggtcttgaa tgtcttttac agtacatccg | | 120 |
| tcaactgtta gcattttcct aaagtcacaa aacagatact aaactgctat agttgaatct | | 180 |
| ttcagaccat tgtcaccaca atg gct tca cag cag gca cca gca aaa gac ctt<br>                                 Met Ala Ser Gln Gln Ala Pro Ala Lys Asp Leu<br>                                  1           5                  10 | | 233 |
| cag acc aac aat tta gag ttt act cca act gat agt tct ggt gtg cag<br>Gln Thr Asn Asn Leu Glu Phe Thr Pro Thr Asp Ser Ser Gly Val Gln<br>               15                  20                  25 | | 281 |
| tgg gca gaa gac atc tct aac tca cca agt gct cag cta aac ttt tcc<br>Trp Ala Glu Asp Ile Ser Asn Ser Pro Ser Ala Gln Leu Asn Phe Ser<br>           30                  35                  40 | | 329 |
| cca agt aac aat ggc tgc tgg gca act cag gag ctg caa agt ctc tgg<br>Pro Ser Asn Asn Gly Cys Trp Ala Thr Gln Glu Leu Gln Ser Leu Trp<br> 45                  50                  55 | | 377 |
| aag atg ttc aac tcc tgg ttg cag cca gaa aag cag act aag gag cag<br>Lys Met Phe Asn Ser Trp Leu Gln Pro Glu Lys Gln Thr Lys Glu Gln<br>60                  65                  70                  75 | | 425 |
| atg att tct caa ttg gtc ttg gag cag ttt ctc ctc act ggg cac tgc<br>Met Ile Ser Gln Leu Val Leu Glu Gln Phe Leu Leu Thr Gly His Cys<br>               80                  85                  90 | | 473 |
| aag gac aag tat gct ttg aca gag aag tgg aaa gcc agt ggt agc gat<br>Lys Asp Lys Tyr Ala Leu Thr Glu Lys Trp Lys Ala Ser Gly Ser Asp<br>               95                 100                 105 | | 521 |
| atg agg aga ttc atg gag agt ctg act gat gag tgc ttg aag cct cct<br>Met Arg Arg Phe Met Glu Ser Leu Thr Asp Glu Cys Leu Lys Pro Pro<br>           110                 115                 120 | | 569 |
| gtc atg gtc cat gtt tca atg caa gga caa gaa gcc ctc ttt tct gaa<br>Val Met Val His Val Ser Met Gln Gly Gln Glu Ala Leu Phe Ser Glu<br>           125                 130                 135 | | 617 |
| aac atg cca tta aaa gaa gtc atc aag ctt ttg aaa caa cag caa tct<br>Asn Met Pro Leu Lys Glu Val Ile Lys Leu Leu Lys Gln Gln Gln Ser<br>140                 145                 150                 155 | | 665 |
| gca aca agg cca ata cca gat aat gca cag atg cca gta gac acc aca<br>Ala Thr Arg Pro Ile Pro Asp Asn Ala Gln Met Pro Val Asp Thr Thr<br>               160                 165                 170 | | 713 |
| caa gat aga tta ttg gcc aca ggc aag aaa aca gtg aaa atg aat gca<br>Gln Asp Arg Leu Leu Ala Thr Gly Lys Lys Thr Val Lys Met Asn Ala | | 761 |

```
                 175               180               185
aca cct ctt gca atg cta ctg aag taa atgttggtga aagctgtagt           808
Thr Pro Leu Ala Met Leu Leu Lys
        190               195 ggaaatgaaa aggactccct tcttattacc cagaaagaac aaaaccatga gcatgaagag   868
gggaatgttg tttgtcaatt ccctcgtggt gccagaagag caagtcaaga cacctccagt   928
catcatgtag acttcccgag tgctctgact cctgcagatg tccccatgga ggaacaacca   988
atggatttat ccagagaaaa catctctgag gacaagaaca attgctataa cacttccagg  1048
aatgcagcta tcaagtata tagtggtgat aatattccca ggaacaagac agactccctt  1108
ttcattaaca agagaatata tcatcctgag cctgaggtgg agatattcc ttatggagtt   1168
cctcaggatt ctacaagagc aagtcaagga acatctacat gcctgcaaga gtcacttggg  1228
gaatgttttt ctgaaaaaga cccaagggag gtaccagggt tgcagtctag caagagcag   1288
cctatctctg atcctgtcct tggtaagaat catgaggcaa acttaccatg tgaaagtcat  1348
caaaagagat tccatagaga tgccaaacta tacaagtgtg aagaatgttc taggatgttc  1408
aaacatgcca ggagcctttc atcccaccag agaactcacc tgaataagaa gagtgaattg  1468
ctttgcatca cctgtcagaa aatattcaaa cgagtttctg accttcgaac ccatgagatc  1528
atacacatgt cagaaaagcc tttcaagtgc agcacatgtg aaaagtcctt cagccacaag  1588
accaacctga gtatcatga gatgattcac acaggagaaa tgccttatgt ctgttcccta   1648
tgtagccgtc gctttcgcca atcatccact taccatcgtc acctgaggaa ttaccacaga  1708
tctgactgaa gtatctaaca tcctcagcag agactggtag ggcttcagcc tcagtatgtc  1768
atcttc                                                             1774

<210> SEQ ID NO 27
<211> LENGTH: 195
<212> TYPE: PRT
<213> ORGANISM: Mus musculus

<400> SEQUENCE: 27

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Ile
145                 150                 155                 160

Pro Asp Asn Ala Gln Met Pro Val Asp Thr Thr Gln Asp Arg Leu Leu
```

```
                     165                 170                 175
Ala Thr Gly Lys Lys Thr Val Lys Met Asn Ala Thr Pro Leu Ala Met
                180                 185                 190

Leu Leu Lys
        195

<210> SEQ ID NO 28
<211> LENGTH: 2275
<212> TYPE: DNA
<213> ORGANISM: Mus musculus
<220> FEATURE:
<221> NAME/KEY: CDS
<222> LOCATION: (201)..(1721)

<400> SEQUENCE: 28
cacagtgcct ccctgggctt cttggcatca cccttgaagt tcaccggaga aagcagtgag        60
gtggaggaat aggtaaactt tccttcctag tggtcttgaa tgtcttttac agtacatcca       120
tcaactgtta gcattttcgt aaagtcacaa aacagatatt aaactactat agttgaatct       180
ttcacaccat tgtcaccaca atg gct tca cag cag gca cca gca aaa gac ctt       233
                       Met Ala Ser Gln Gln Ala Pro Ala Lys Asp Leu
                         1               5                  10 cag acc aac aat tta gag ttt act cca act gat agt tct ggt gtg cag       281
Gln Thr Asn Asn Leu Glu Phe Thr Pro Thr Asp Ser Ser Gly Val Gln
         15                  20                  25 tgg gca gaa gac atc tct aac tca cca agt gct cag cta aac ttt tcc       329
Trp Ala Glu Asp Ile Ser Asn Ser Pro Ser Ala Gln Leu Asn Phe Ser
     30                  35                  40 cca agt aac aat ggc tgc tgg gca act cag gag ctg caa agt ctc tgg       377
Pro Ser Asn Asn Gly Cys Trp Ala Thr Gln Glu Leu Gln Ser Leu Trp
 45                  50                  55 aag atg ttc aac tcc tgg ttg cag cca gaa aag cag act aag gag cag       425
Lys Met Phe Asn Ser Trp Leu Gln Pro Glu Lys Gln Thr Lys Glu Gln
 60                  65                  70                  75 atg att tct caa ctg gtc ttg gag cag ttt ctc ctc act ggg cac tgc       473
Met Ile Ser Gln Leu Val Leu Glu Gln Phe Leu Leu Thr Gly His Cys
             80                  85                  90 aag gac aag tat gct ttg aca gag aag tgg aaa gcc agt ggt agc gat       521
Lys Asp Lys Tyr Ala Leu Thr Glu Lys Trp Lys Ala Ser Gly Ser Asp
         95                 100                 105 atg agg aga ttc atg gag agt ctg act gat gag tgc ttg aag cct cct       569
Met Arg Arg Phe Met Glu Ser Leu Thr Asp Glu Cys Leu Lys Pro Pro
    110                 115                 120 gtc atg gtc cat gtt tca atg caa gga caa gaa gcc ctc ttt tct gaa       617
Val Met Val His Val Ser Met Gln Gly Gln Glu Ala Leu Phe Ser Glu
125                 130                 135 aac atg cca tta aaa gaa gtc atc aag ctt ttg aaa caa cag caa tct       665
Asn Met Pro Leu Lys Glu Val Ile Lys Leu Leu Lys Gln Gln Gln Ser
        140                 145                 150                 155 gca aca agg cca aca cca gat aat gag cag atg cca gta gac acc aca       713
Ala Thr Arg Pro Thr Pro Asp Asn Glu Gln Met Pro Val Asp Thr Thr
            160                 165                 170 caa gat aga tta ttg gcc aca gga caa gaa aac agt gaa aat gaa tgc       761
Gln Asp Arg Leu Leu Ala Thr Gly Gln Glu Asn Ser Glu Asn Glu Cys
        175                 180                 185 aac aac tct tgt aat gct act gaa gca aat gtt ggt gaa agc tgt agt       809
Asn Asn Ser Cys Asn Ala Thr Glu Ala Asn Val Gly Glu Ser Cys Ser
        190                 195                 200 gga aat gaa atg gac tcc ctt ctt att atc cag aaa gaa cag cac cct       857
Gly Asn Glu Met Asp Ser Leu Leu Ile Ile Gln Lys Glu Gln His Pro
```

|  |  |  |  |  |  |  |  |  |  |  |  |  |  |  |  |
|---|---|---|---|---|---|---|---|---|---|---|---|---|---|---|---|
|  |  |  |  | 205 |  |  |  | 210 |  |  |  | 215 |  |  |  |
| gag | cat | gaa | gag | ggg | aat | gtt | gtt | tgt | caa | ttc | cct | cat | ggt | gcc | aga | 905 |
| Glu | His | Glu | Glu | Gly | Asn | Val | Val | Cys | Gln | Phe | Pro | His | Gly | Ala | Arg |  |
| 220 |  |  |  |  | 225 |  |  |  |  | 230 |  |  |  |  | 235 |  |
| aga | gca | agt | caa | ggc | acc | ccc | agt | cat | cat | gta | gac | ttc | ccg | agt | gct | 953 |
| Arg | Ala | Ser | Gln | Gly | Thr | Pro | Ser | His | His | Val | Asp | Phe | Pro | Ser | Ala |  |
|  |  |  | 240 |  |  |  |  | 245 |  |  |  |  | 250 |  |  |  |
| ccg | act | act | gcc | gat | gtc | ccc | atg | gag | gaa | caa | cca | aag | gat | tta | tcc | 1001 |
| Pro | Thr | Thr | Ala | Asp | Val | Pro | Met | Glu | Glu | Gln | Pro | Lys | Asp | Leu | Ser |  |
| 255 |  |  |  |  | 260 |  |  |  |  | 265 |  |  |  |  |  |  |
| aga | gaa | aac | atc | tct | gag | gac | aag | aac | aat | tgc | tat | aac | act | tcc | aga | 1049 |
| Arg | Glu | Asn | Ile | Ser | Glu | Asp | Lys | Asn | Asn | Cys | Tyr | Asn | Thr | Ser | Arg |  |
|  | 270 |  |  |  |  | 275 |  |  |  |  | 280 |  |  |  |  |  |
| aat | gca | gct | act | caa | gta | tat | agt | ggt | gat | aat | att | ccc | agg | aac | aag | 1097 |
| Asn | Ala | Ala | Thr | Gln | Val | Tyr | Ser | Gly | Asp | Asn | Ile | Pro | Arg | Asn | Lys |  |
| 285 |  |  |  |  | 290 |  |  |  |  | 295 |  |  |  |  |  |  |
| tca | gac | tcc | ctt | ttc | att | aac | aag | aga | ata | tat | cat | cct | gag | cct | gag | 1145 |
| Ser | Asp | Ser | Leu | Phe | Ile | Asn | Lys | Arg | Ile | Tyr | His | Pro | Glu | Pro | Glu |  |
| 300 |  |  |  |  | 305 |  |  |  |  | 310 |  |  |  |  | 315 |  |
| gtg | gga | gat | att | cct | tat | gga | gtt | cct | cag | gat | tct | aca | aga | gca | agt | 1193 |
| Val | Gly | Asp | Ile | Pro | Tyr | Gly | Val | Pro | Gln | Asp | Ser | Thr | Arg | Ala | Ser |  |
|  |  |  | 320 |  |  |  |  | 325 |  |  |  |  | 330 |  |  |  |
| caa | gga | aca | tct | aca | tgc | ctg | caa | gag | tca | ctt | ggg | gaa | tgt | ttt | tct | 1241 |
| Gln | Gly | Thr | Ser | Thr | Cys | Leu | Gln | Glu | Ser | Leu | Gly | Glu | Cys | Phe | Ser |  |
|  |  |  | 335 |  |  |  |  | 340 |  |  |  |  | 345 |  |  |  |
| gaa | aac | gac | cca | agg | gag | gta | cca | ggg | ttg | cag | tct | agg | caa | gag | cag | 1289 |
| Glu | Asn | Asp | Pro | Arg | Glu | Val | Pro | Gly | Leu | Gln | Ser | Arg | Gln | Glu | Gln |  |
|  |  | 350 |  |  |  |  | 355 |  |  |  |  | 360 |  |  |  |  |
| cct | atc | tct | gat | cct | gtc | ctt | ctt | ggt | aag | aat | cat | gag | gca | aac | tta | 1337 |
| Pro | Ile | Ser | Asp | Pro | Val | Leu | Leu | Gly | Lys | Asn | His | Glu | Ala | Asn | Leu |  |
| 365 |  |  |  |  | 370 |  |  |  |  | 375 |  |  |  |  |  |  |
| cca | tgt | gaa | agt | cat | caa | aag | aga | ttc | tgt | aga | gat | gcc | aaa | cta | tac | 1385 |
| Pro | Cys | Glu | Ser | His | Gln | Lys | Arg | Phe | Cys | Arg | Asp | Ala | Lys | Leu | Tyr |  |
| 380 |  |  |  |  | 385 |  |  |  |  | 390 |  |  |  |  | 395 |  |
| aag | tgt | gaa | gaa | tgt | tct | agg | atg | ttc | aaa | cat | gcc | agg | agc | ctt | tca | 1433 |
| Lys | Cys | Glu | Glu | Cys | Ser | Arg | Met | Phe | Lys | His | Ala | Arg | Ser | Leu | Ser |  |
|  |  |  |  | 400 |  |  |  |  | 405 |  |  |  |  | 410 |  |  |
| tcc | cac | cag | aga | act | cac | ctg | aat | aag | aag | agt | gaa | ttg | ctt | tgt | gtc | 1481 |
| Ser | His | Gln | Arg | Thr | His | Leu | Asn | Lys | Lys | Ser | Glu | Leu | Leu | Cys | Val |  |
|  |  |  | 415 |  |  |  |  | 420 |  |  |  |  | 425 |  |  |  |
| acc | tgt | cag | aaa | atg | ttc | aaa | cga | gtc | tct | gac | cgc | cga | acc | cat | gag | 1529 |
| Thr | Cys | Gln | Lys | Met | Phe | Lys | Arg | Val | Ser | Asp | Arg | Arg | Thr | His | Glu |  |
|  |  | 430 |  |  |  |  | 435 |  |  |  |  | 440 |  |  |  |  |
| atc | ata | cac | atg | cca | gaa | aag | cct | ttc | aag | tgt | agc | aca | tgt | gaa | aag | 1577 |
| Ile | Ile | His | Met | Pro | Glu | Lys | Pro | Phe | Lys | Cys | Ser | Thr | Cys | Glu | Lys |  |
| 445 |  |  |  |  | 450 |  |  |  |  | 455 |  |  |  |  |  |  |
| tcc | ttc | agc | cac | aag | acc | aac | ctg | aag | tct | cat | gag | atg | att | cac | aca | 1625 |
| Ser | Phe | Ser | His | Lys | Thr | Asn | Leu | Lys | Ser | His | Glu | Met | Ile | His | Thr |  |
| 460 |  |  |  |  | 465 |  |  |  |  | 470 |  |  |  |  | 475 |  |
| gga | gaa | atg | cct | tat | gtc | tgt | tcc | cta | tgt | agc | cgt | cgc | ttt | cgc | caa | 1673 |
| Gly | Glu | Met | Pro | Tyr | Val | Cys | Ser | Leu | Cys | Ser | Arg | Arg | Phe | Arg | Gln |  |
|  |  |  |  | 480 |  |  |  |  | 485 |  |  |  |  | 490 |  |  |
| tca | tcc | act | tac | cat | cgt | cac | ctg | agg | aat | tac | cac | aga | tct | gac | tga | 1721 |
| Ser | Ser | Thr | Tyr | His | Arg | His | Leu | Arg | Asn | Tyr | His | Arg | Ser | Asp |  |  |
|  |  |  | 495 |  |  |  |  | 500 |  |  |  |  | 505 |  |  |  | actatctaac atcctcagca gagactggta gggcttcagc ctcagtatgt catcttcaaa 1781 gagagaagaa tgttgcaagt aaattgtact gtcccaataa tgatataaca tgcttgtgga 1841 ttgccacttt tatgttttgt tttgttttgt twtttatktt gtgtgtgtgt atgtaatttt 1901

```
ttgtctgtat ttccatattt ccacagcata agttattaga atactttgct gttaattctt      1961
gagttgcttc ttgcttttag acagtgtctt tctggttggc agctttatac acctgtcttt      2021
ctggcactag agtttccaaa cattttctga tctccacttt tattttctac agtgttcttg      2081
acagaagcct ggcattccct ctgacatttt ctacatgttg gggttttcat cccaagtctt      2141
agggttgcaa gttaaatgca ttgcctcttc agacatctca tgccatgtct actgcttaca      2201
gttcaagaat atttctctac attactagaa cgacgttcaa gtggaataa taaataaata      2261 aataatcaac aatt                                                        2275
```

<210> SEQ ID NO 29
<211> LENGTH: 506
<212> TYPE: PRT
<213> ORGANISM: Mus musculus

<400> SEQUENCE: 29

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
                20                  25                  30

Ser Asn Ser Pro Ser Ala Gln Leu Asn Phe Ser Pro Ser Asn Asn Gly
            35                  40                  45

Cys Trp Ala Thr Gln Glu Leu Gln Ser Leu Trp Lys Met Phe Asn Ser
        50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300
```

```
Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
            325                 330                 335

Cys Leu Gln Glu Ser Leu Gly Cys Phe Ser Glu Asn Asp Pro Arg
        340                 345                 350

Glu Val Pro Gly Leu Gln Ser Arg Gln Glu Gln Pro Ile Ser Asp Pro
            355                 360                 365

Val Leu Leu Gly Lys Asn His Glu Ala Asn Leu Pro Cys Glu Ser His
370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 30
<211> LENGTH: 2268
<212> TYPE: DNA
<213> ORGANISM: Mus musculus
<220> FEATURE:
<221> NAME/KEY: CDS
<222> LOCATION: (201)..(1721)

<400> SEQUENCE: 30
cacagtgcct ccctgggctt cttggcatca cccttgaagt tcactggaca aagaggtgag    60
gtggaggagt aggtaaactt cccttcctag tggtcgtgaa tgtcttttac agtacatcca   120
tcaactgtta gcattttcat aaagtcacaa aacagatact aaactgctat agttgaatct   180
ttcacaccat tgtcaccaca atg gct tca cag cag gca cca gca aaa gac ctt   233
                      Met Ala Ser Gln Gln Ala Pro Ala Lys Asp Leu
                       1               5                  10 cag acc aac aat tta gag ttt act cca tct cat agt tct ggt gtg cag   281
Gln Thr Asn Asn Leu Glu Phe Thr Pro Ser His Ser Ser Gly Val Gln
            15                  20                  25 tgg gta gaa gac atc tct aac tca cca agt gct cag cta aac ttt tct   329
Trp Val Glu Asp Ile Ser Asn Ser Pro Ser Ala Gln Leu Asn Phe Ser
        30                  35                  40 cca agt aac aat ggc tgc tgg gca act cag gag ctg caa agt ctc tgg   377
Pro Ser Asn Asn Gly Cys Trp Ala Thr Gln Glu Leu Gln Ser Leu Trp
    45                  50                  55 aag atg ttc aac tcc tgg ttg cag cca gaa aag cag act aag gag cag   425
Lys Met Phe Asn Ser Trp Leu Gln Pro Glu Lys Gln Thr Lys Glu Gln
60                  65                  70                  75 atg att tct caa ctg gtc ttg gag cag ttt ctc ctc att ggg cac tgc   473
Met Ile Ser Gln Leu Val Leu Glu Gln Phe Leu Leu Ile Gly His Cys
```

|  |  |  |  |  |  |  |  |  |  |  |  |  |  |  |  |
|---|---|---|---|---|---|---|---|---|---|---|---|---|---|---|---|
|  |  |  | 80 |  |  |  | 85 |  |  |  | 90 |  |  |  |  |
| aag | gac | aag | tat | gct | ttg | aca | gag | aag | tgg | aaa | gcc | agt | ggt | agc | gat | 521 |
| Lys | Asp | Lys | Tyr | Ala | Leu | Thr | Glu | Lys | Trp | Lys | Ala | Ser | Gly | Ser | Asp |
|  |  | 95 |  |  |  |  | 100 |  |  |  |  | 105 |  |  |  |
| atg | agg | aga | ttc | atg | gag | agt | ctg | act | gat | gag | tgc | ttg | aag | cct | cct | 569 |
| Met | Arg | Arg | Phe | Met | Glu | Ser | Leu | Thr | Asp | Glu | Cys | Leu | Lys | Pro | Pro |
|  | 110 |  |  |  |  | 115 |  |  |  |  | 120 |  |  |  |  |
| gtc | atg | gtc | cat | gtt | tca | atg | caa | gga | caa | gaa | gct | ctc | ttt | tct | gaa | 617 |
| Val | Met | Val | His | Val | Ser | Met | Gln | Gly | Gln | Glu | Ala | Leu | Phe | Ser | Glu |
| 125 |  |  |  |  | 130 |  |  |  |  | 135 |  |  |  |  |  |
| aac | atg | cca | tta | aaa | gaa | gtc | atc | aag | ctt | ttg | aaa | caa | cag | caa | tct | 665 |
| Asn | Met | Pro | Leu | Lys | Glu | Val | Ile | Lys | Leu | Leu | Lys | Gln | Gln | Gln | Ser |
| 140 |  |  |  |  | 145 |  |  |  |  | 150 |  |  |  |  | 155 |
| gca | aca | agg | cca | aca | cca | gat | aat | gag | cag | atg | cca | gta | gac | acc | aca | 713 |
| Ala | Thr | Arg | Pro | Thr | Pro | Asp | Asn | Glu | Gln | Met | Pro | Val | Asp | Thr | Thr |
|  |  |  |  | 160 |  |  |  |  | 165 |  |  |  |  | 170 |  |
| caa | gat | aga | tta | ttg | gcc | aca | gga | caa | gaa | aac | agt | gaa | aat | gaa | tgc | 761 |
| Gln | Asp | Arg | Leu | Leu | Ala | Thr | Gly | Gln | Glu | Asn | Ser | Glu | Asn | Glu | Cys |
|  |  |  | 175 |  |  |  |  | 180 |  |  |  |  | 185 |  |  |
| aac | aac | tct | tgt | aat | gct | act | gaa | gca | aat | gtt | ggt | gaa | agc | tgt | agt | 809 |
| Asn | Asn | Ser | Cys | Asn | Ala | Thr | Glu | Ala | Asn | Val | Gly | Glu | Ser | Cys | Ser |
|  |  | 190 |  |  |  |  | 195 |  |  |  |  | 200 |  |  |  |
| gga | aat | gaa | atg | gac | tcc | ctt | ctt | att | atc | cag | aaa | gaa | cag | cac | cct | 857 |
| Gly | Asn | Glu | Met | Asp | Ser | Leu | Leu | Ile | Ile | Gln | Lys | Glu | Gln | His | Pro |
| 205 |  |  |  |  | 210 |  |  |  |  | 215 |  |  |  |  |  |
| gag | cat | gaa | gag | ggg | aat | gtt | gtt | ttt | caa | ttc | cct | ctt | gat | gcc | aga | 905 |
| Glu | His | Glu | Glu | Gly | Asn | Val | Val | Phe | Gln | Phe | Pro | Leu | Asp | Ala | Arg |
| 220 |  |  |  |  | 225 |  |  |  |  | 230 |  |  |  |  | 235 |
| aga | gca | agt | caa | ggc | aac | tcc | agt | cat | cat | gta | gac | ttc | cgg | agt | gct | 953 |
| Arg | Ala | Ser | Gln | Gly | Asn | Ser | Ser | His | His | Val | Asp | Phe | Arg | Ser | Ala |
|  |  |  | 240 |  |  |  |  | 245 |  |  |  |  | 250 |  |  |
| ccg | act | cct | gcg | gat | gtc | ccc | atg | gag | gaa | caa | cca | aag | gat | tta | tcc | 1001 |
| Pro | Thr | Pro | Ala | Asp | Val | Pro | Met | Glu | Glu | Gln | Pro | Lys | Asp | Leu | Ser |
|  |  | 255 |  |  |  |  | 260 |  |  |  |  | 265 |  |  |  |
| aga | gaa | aac | atc | tct | gag | gac | aag | aac | aat | tgc | tat | aac | act | tcc | agg | 1049 |
| Arg | Glu | Asn | Ile | Ser | Glu | Asp | Lys | Asn | Asn | Cys | Tyr | Asn | Thr | Ser | Arg |
|  | 270 |  |  |  |  | 275 |  |  |  |  | 280 |  |  |  |  |
| aat | gca | gct | act | caa | gta | tat | aga | agt | gat | aat | att | ccc | agg | aaa | aag | 1097 |
| Asn | Ala | Ala | Thr | Gln | Val | Tyr | Arg | Ser | Asp | Asn | Ile | Pro | Arg | Lys | Lys |
| 285 |  |  |  |  | 290 |  |  |  |  | 295 |  |  |  |  |  |
| aca | gac | tcc | ctt | tcc | att | aac | aag | aga | ata | tat | cat | tct | gag | cct | gag | 1145 |
| Thr | Asp | Ser | Leu | Ser | Ile | Asn | Lys | Arg | Ile | Tyr | His | Ser | Glu | Pro | Glu |
| 300 |  |  |  |  | 305 |  |  |  |  | 310 |  |  |  |  | 315 |
| gag | gga | gat | att | cct | tat | gga | gtt | cct | cag | gat | tct | aca | aga | gca | agt | 1193 |
| Glu | Gly | Asp | Ile | Pro | Tyr | Gly | Val | Pro | Gln | Asp | Ser | Thr | Arg | Ala | Ser |
|  |  |  | 320 |  |  |  |  | 325 |  |  |  |  | 330 |  |  |
| caa | gga | aca | tct | aca | tgc | ttg | caa | gag | tca | ctt | ggg | gaa | tgt | ttt | tct | 1241 |
| Gln | Gly | Thr | Ser | Thr | Cys | Leu | Gln | Glu | Ser | Leu | Gly | Glu | Cys | Phe | Ser |
|  |  | 335 |  |  |  |  | 340 |  |  |  |  | 345 |  |  |  |
| gaa | aaa | gac | cct | agg | gag | cta | cca | ggg | ttg | gag | tct | agg | caa | gag | gag | 1289 |
| Glu | Lys | Asp | Pro | Arg | Glu | Leu | Pro | Gly | Leu | Glu | Ser | Arg | Gln | Glu | Glu |
|  | 350 |  |  |  |  | 355 |  |  |  |  | 360 |  |  |  |  |
| cct | atc | tct | gat | cct | gtc | ttt | ctt | ggt | aag | gat | cat | gag | gca | aac | tta | 1337 |
| Pro | Ile | Ser | Asp | Pro | Val | Phe | Leu | Gly | Lys | Asp | His | Glu | Ala | Asn | Leu |
| 365 |  |  |  |  | 370 |  |  |  |  | 375 |  |  |  |  |  |
| cca | tgt | gaa | agt | cat | caa | aag | aga | ttc | cgt | aga | gat | gcc | aaa | cta | ttc | 1385 |
| Pro | Cys | Glu | Ser | His | Gln | Lys | Arg | Phe | Arg | Arg | Asp | Ala | Lys | Leu | Phe |
| 380 |  |  |  |  | 385 |  |  |  |  | 390 |  |  |  |  | 395 |
| aag | tgt | gaa | gaa | tgt | tct | agg | atg | ttc | aaa | cat | gcc | agg | agc | ctt | tcg | 1433 |

```
Lys Cys Glu Glu Cys Ser Arg Met Phe Lys His Ala Arg Ser Leu Ser
                400                 405                 410 tcc cac cag aga act cac ctg aat aag aag agt gaa ttg ctt tgt gtc    1481
Ser His Gln Arg Thr His Leu Asn Lys Lys Ser Glu Leu Leu Cys Val
                415                 420                 425 acc tgt cag aaa atg ttc aaa cga gtc tct gac cgc cga acc cat gag    1529
Thr Cys Gln Lys Met Phe Lys Arg Val Ser Asp Arg Arg Thr His Glu
                430                 435                 440 atc ata cac atg cca gaa aag cct ttc aag tgc agc aca tgt gaa aag    1577
Ile Ile His Met Pro Glu Lys Pro Phe Lys Cys Ser Thr Cys Glu Lys
                445                 450                 455 tcc ttc agc cac aag acc aac ctg aag tct cat gag atg att cac aca    1625
Ser Phe Ser His Lys Thr Asn Leu Lys Ser His Glu Met Ile His Thr
460                 465                 470                 475 gga gaa atg cct tat gtc tgt tcc cta tgt agc cgt cgc ttt cgc caa    1673
Gly Glu Met Pro Tyr Val Cys Ser Leu Cys Ser Arg Arg Phe Arg Gln
                480                 485                 490 tca tcc act tac cat cgt cac ctg agg aat tac cac aga tct gac tga   1721
Ser Ser Thr Tyr His Arg His Leu Arg Asn Tyr His Arg Ser Asp
                495                 500                 505 agtatctaac atcctcagca gagactggta gggcttcagc ctcagtatgt catcttcaaa   1781
gagagaagaa tgttgcaagt aaattgtact gtcccaataa tgatataaca tgcttgtgga   1841
ttgccacttt tatgttttgt ttttattgt gtgtgtgtgt gtatgtaatt ttttgtctgt    1901
aatttccata gttccacagc ataagttatt agaatacttt gctgttaatt cttgagttgc   1961
ttcttgcttt tagacagtgt ctttctggtt ggcagcttta tacacctgtc tttctggcac   2021
tagagtttcc aaacattttc tgatctccac ttttattctc tacagtggtc ctgacagagg   2081
cctgccattc cctctgacat tttttaacat gttggggttt catcccaagt cttagggttg   2141
caagttaaat gcattgcctc ttcagacatc tcatgtcatg tctactgctt acagttcaag   2201
aatatttctc tacattacta gaatgacgtt caaagtggaa taataaataa aaaataatc    2261 aacaatt                                                              2268
```

<210> SEQ ID NO 31
<211> LENGTH: 506
<212> TYPE: PRT
<213> ORGANISM: Mus musculus

<400> SEQUENCE: 31

```
Met Ala Ser Gln Gln Ala Pro Ala Lys Asp Leu Gln Thr Asn Asn Leu
1               5                   10                  15

Glu Phe Thr Pro Ser His Ser Ser Gly Val Gln Trp Val Glu Asp Ile
                20                  25                  30

Ser Asn Ser Pro Ser Ala Gln Leu Asn Phe Ser Pro Ser Asn Asn Gly
            35                  40                  45

Cys Trp Ala Thr Gln Glu Leu Gln Ser Leu Trp Lys Met Phe Asn Ser
50                  55                  60

Trp Leu Gln Pro Glu Lys Gln Thr Lys Glu Gln Met Ile Ser Gln Leu
65                  70                  75                  80

Val Leu Glu Gln Phe Leu Leu Ile Gly His Cys Lys Asp Lys Tyr Ala
                85                  90                  95

Leu Thr Glu Lys Trp Lys Ala Ser Gly Ser Asp Met Arg Arg Phe Met
                100                 105                 110

Glu Ser Leu Thr Asp Glu Cys Leu Lys Pro Pro Val Met Val His Val
                115                 120                 125
```

Ser Met Gln Gly Gln Glu Ala Leu Phe Ser Glu Asn Met Pro Leu Lys
130                 135                 140

Glu Val Ile Lys Leu Leu Lys Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
210                 215                 220

Asn Val Val Phe Gln Phe Pro Leu Asp Ala Arg Arg Ala Ser Gln Gly
225                 230                 235                 240

Asn Ser Ser His His Val Asp Phe Arg Ser Ala Pro Thr Pro Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Arg Ser Asp Asn Ile Pro Arg Lys Lys Thr Asp Ser Leu Ser
290                 295                 300

Ile Asn Lys Arg Ile Tyr His Ser Glu Pro Glu Glu Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Leu Pro Gly Leu Glu Ser Arg Gln Glu Glu Pro Ile Ser Asp Pro
        355                 360                 365

Val Phe Leu Gly Lys Asp His Glu Ala Asn Leu Pro Cys Glu Ser His
370                 375                 380

Gln Lys Arg Phe Arg Arg Asp Ala Lys Leu Phe Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Thr His Glu Ile Ile His Met Pro
        435                 440                 445

Glu Lys Pro Phe Lys Cys Ser Thr Cys Glu Lys Ser Phe Ser His Lys
450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505

<210> SEQ ID NO 32
<211> LENGTH: 1774
<212> TYPE: DNA
<213> ORGANISM: Mus musculus
<220> FEATURE:
<221> NAME/KEY: CDS

<222> LOCATION: (201)..(788)

<400> SEQUENCE: 32

| | | |
|---|---|---|
| cacagtgcct ccctgggctt cttggcatca ccattgaagt tcactggaga aagaggtgag | 60 |
| gtggagaagt aggtaaactt ccctttcttg tggtcttgaa tgtcttttac agtacatccg | 120 |
| tcaactgtta gcattttcct aaagtcacaa aacagatact aaactgctat agttgaatct | 180 |

| ttcagaccat tgtcaccaca atg gct tca cag cag gca cca gca aaa gac ctt | | 233 |
|---|---|---|
| Met Ala Ser Gln Gln Ala Pro Ala Lys Asp Leu | | |
| 1 5 10 | | |

| cag acc aac aat tta gag ttt act cca act gat agt tct ggt gtg cag | 281 |
|---|---|
| Gln Thr Asn Asn Leu Glu Phe Thr Pro Thr Asp Ser Ser Gly Val Gln | |
| 15 20 25 | |

| tgg gca gaa gac atc tct aac tca cca agt gct cag cta aac ttt tcc | 329 |
|---|---|
| Trp Ala Glu Asp Ile Ser Asn Ser Pro Ser Ala Gln Leu Asn Phe Ser | |
| 30 35 40 | |

| cca agt aac aat ggc tgc tgg gca act cag gag ctg caa agt ctc tgg | 377 |
|---|---|
| Pro Ser Asn Asn Gly Cys Trp Ala Thr Gln Glu Leu Gln Ser Leu Trp | |
| 45 50 55 | |

| aag atg ttc aac tcc tgg ttg cag cca gaa aag cag act aag gag cag | 425 |
|---|---|
| Lys Met Phe Asn Ser Trp Leu Gln Pro Glu Lys Gln Thr Lys Glu Gln | |
| 60 65 70 75 | |

| atg att tct caa ctg gtc ttg gag cag ttt ctc ctc act ggg cac tgc | 473 |
|---|---|
| Met Ile Ser Gln Leu Val Leu Glu Gln Phe Leu Leu Thr Gly His Cys | |
| 80 85 90 | |

| aag gac aag tat gct ttg aca gag aag tgg aaa gcc agt ggt agc gat | 521 |
|---|---|
| Lys Asp Lys Tyr Ala Leu Thr Glu Lys Trp Lys Ala Ser Gly Ser Asp | |
| 95 100 105 | |

| atg agg aga ttc atg gag agt ctg act gat gag tgc ttg aag cct cct | 569 |
|---|---|
| Met Arg Arg Phe Met Glu Ser Leu Thr Asp Glu Cys Leu Lys Pro Pro | |
| 110 115 120 | |

| gtc atg gtc cat gtt tca atg caa gga caa gaa gcc ctc ttt tct gaa | 617 |
|---|---|
| Val Met Val His Val Ser Met Gln Gly Gln Glu Ala Leu Phe Ser Glu | |
| 125 130 135 | |

| aac atg cca tta aaa gaa gtc atc aag ctt ttg aaa caa cag caa tct | 665 |
|---|---|
| Asn Met Pro Leu Lys Glu Val Ile Lys Leu Leu Lys Gln Gln Gln Ser | |
| 140 145 150 155 | |

| gca aca agg cca ata cca gat aat gag cag atg cca gta gac acc aca | 713 |
|---|---|
| Ala Thr Arg Pro Ile Pro Asp Asn Glu Gln Met Pro Val Asp Thr Thr | |
| 160 165 170 | |

| caa gat aga tta ttg gcc aca ggc aag aaa aca gtg aaa atg aat gca | 761 |
|---|---|
| Gln Asp Arg Leu Leu Ala Thr Gly Lys Lys Thr Val Lys Met Asn Ala | |
| 175 180 185 | |

| aca cct ctt gca atg cta ctg aag taa atgttggtga aagctgtagt | 808 |
|---|---|
| Thr Pro Leu Ala Met Leu Leu Lys | |
| 190 195 | |

| | |
|---|---|
| ggaaatgaaa aggactccct tcttattacc cagaaagaac aaaaccatga gcatgaagag | 868 |
| gggaatgttg tttgtcaatt ccctcgtggt gccagaagag caagtcaaga cacctccagt | 928 |
| catcatgtag acttcccgag tgctctgact cctgcagatg tccccatgga ggaacaacca | 988 |
| atggatttat ccagagaaaa catctctgag gacaagaaca attgctataa cacttccagg | 1048 |
| aatgcagcta ctcaagtata taatggtgat aatattccca ggaacaagac agactccctt | 1108 |
| ttcattaaca agagaatata tcatcctgag cctgaggtgg gagatattcc ttatggagtt | 1168 |
| cctcaggatt ctacaagagc aagtcaagga acatctacat gcctgcaaga gtcacttggg | 1228 |
| gaatgttttt ctgaaaaaga cccaagggag gtaccagggt gcagtctag caagagcag | 1288 |
| cctatctctg atcctgtcct tggtaagaat catgaggcaa acttaccatg tgaaagtcat | 1348 |

```
caaaagagat tccatagaga tgccaaacta tacaagtgtg aagaatgttc taggatgttc     1408
aaacatgcca ggagcctttc atcccaccag agaactcacc tgaataagaa gagtgaattg     1468
ctttgcatca cctgtcagaa aatattcaaa cgagtttctg accttcgaac ccatgagatc     1528
atacacatgt cagaaaagcc tttcaagtgc agcacatgtg aaaagtcctt cagccacaag     1588
accaacctga gtatcatga gatgattcac acaggagaaa tgccttatgt ctgttcccta      1648
tgtagccgtc gctttcgcca atcatccact taccatcgtc acctgaggaa ttaccacaga     1708
tctgactgaa gtatctaaca tcctcagcag agactggtag ggcttcagcc tcagtatgtc     1768
atcttc                                                                1774
```

<210> SEQ ID NO 33
<211> LENGTH: 195
<212> TYPE: PRT
<213> ORGANISM: Mus musculus

<400> SEQUENCE: 33

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Glu Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 34
<211> LENGTH: 2273
<212> TYPE: DNA
<213> ORGANISM: Mus musculus
<220> FEATURE:
<221> NAME/KEY: CDS
<222> LOCATION: (201)..(1721)

<400> SEQUENCE: 34

```
cacagtgcct ccctgggctt cttggcatca cccttgaagt tcactggaga aagaggtgag     60
gtggaggaat aggtaaactt tccttcctag tggtcttgaa tgtctttac agtacatcca      120
```

-continued

```
tcaactgtta gcattttcgt aaagtcacaa aacagatatt aaactactat agttgaatct        180
ttcacaccat tgtcaccaca atg gct tca cag cag gca cca gca aaa gac ctt       233
                      Met Ala Ser Gln Gln Ala Pro Ala Lys Asp Leu
                        1               5                  10 cag acc aac aat tta gag ttt act cca act gat agt tct ggt gtg cag         281
Gln Thr Asn Asn Leu Glu Phe Thr Pro Thr Asp Ser Ser Gly Val Gln
             15                  20                  25 tgg gca gaa gac atc tct aac tca cca agt gct cag cta aac ttt tcc         329
Trp Ala Glu Asp Ile Ser Asn Ser Pro Ser Ala Gln Leu Asn Phe Ser
         30                  35                  40 cca agt aac aat ggc tgc tgg gca act cag gag ctg caa agt ctc tgg         377
Pro Ser Asn Asn Gly Cys Trp Ala Thr Gln Glu Leu Gln Ser Leu Trp
     45                  50                  55 aag atg ttc aac tcc tgg ttg cag cca gaa aag cag act aag gag cag         425
Lys Met Phe Asn Ser Trp Leu Gln Pro Glu Lys Gln Thr Lys Glu Gln
 60                  65                  70                  75 atg att tct caa ctg gtc ttg gag cag ttt ctc ctc act ggg cac tgc         473
Met Ile Ser Gln Leu Val Leu Glu Gln Phe Leu Leu Thr Gly His Cys
                 80                  85                  90 aag gac aag tat gct ttg act gag aag tgg aaa gcc agt ggt agc gat         521
Lys Asp Lys Tyr Ala Leu Thr Glu Lys Trp Lys Ala Ser Gly Ser Asp
             95                 100                 105 atg agg aga ttc atg gag agt ctg act gat gag tgc ttg aag cct cct         569
Met Arg Arg Phe Met Glu Ser Leu Thr Asp Glu Cys Leu Lys Pro Pro
        110                 115                 120 gtc atg gtc cat gtt tca atg caa gga caa gaa gcc ctc ttt tct gaa         617
Val Met Val His Val Ser Met Gln Gly Gln Glu Ala Leu Phe Ser Glu
    125                 130                 135 aac atg cca tta aaa gaa gtc atc aag ctt ttg aaa caa cag caa tct         665
Asn Met Pro Leu Lys Glu Val Ile Lys Leu Leu Lys Gln Gln Gln Ser
140                 145                 150                 155 gca aca agg cca aca cca gat aat gag cag atg cca gta gac acc aca         713
Ala Thr Arg Pro Thr Pro Asp Asn Glu Gln Met Pro Val Asp Thr Thr
                160                 165                 170 caa gat aga tta ttg gcc aca gga caa gaa aac agt gaa aat gaa tgc         761
Gln Asp Arg Leu Leu Ala Thr Gly Gln Glu Asn Ser Glu Asn Glu Cys
            175                 180                 185 aac aac tct tgt aat gct act gaa gca aat gtt ggt gaa agc tgt agt         809
Asn Asn Ser Cys Asn Ala Thr Glu Ala Asn Val Gly Glu Ser Cys Ser
        190                 195                 200 gga aat gaa atg gac tcc ctt ctt att atg cag aaa gaa cag cac cct         857
Gly Asn Glu Met Asp Ser Leu Leu Ile Met Gln Lys Glu Gln His Pro
    205                 210                 215 gag cat gaa gag ggg aat gtt gtt tgt caa ttc cct cat ggt gcc aga         905
Glu His Glu Glu Gly Asn Val Val Cys Gln Phe Pro His Gly Ala Arg
220                 225                 230                 235 aga gca agt caa ggc acc ccc agt cat cat gta gac ttc ccg agt gct         953
Arg Ala Ser Gln Gly Thr Pro Ser His His Val Asp Phe Pro Ser Ala
                240                 245                 250 ccg act act gcc gat gtc ccc atg gag gaa caa cca aag gat tta tcc        1001
Pro Thr Thr Ala Asp Val Pro Met Glu Glu Gln Pro Lys Asp Leu Ser
            255                 260                 265 aga gaa aac atc tct gag gac aag aac aat tgc tat aac act tcc aga        1049
Arg Glu Asn Ile Ser Glu Asp Lys Asn Asn Cys Tyr Asn Thr Ser Arg
        270                 275                 280 aat gca gct act caa gta tat agt ggt gat aat att ccc agg aac aag        1097
Asn Ala Ala Thr Gln Val Tyr Ser Gly Asp Asn Ile Pro Arg Asn Lys
    285                 290                 295 tca gac tcc ctt ttc att aac aag aga ata tat cat cct gag cct gag        1145
```

| | | |
|---|---|---|
| Ser Asp Ser Leu Phe Ile Asn Lys Arg Ile Tyr His Pro Glu Pro Glu<br>300                           305                     310                   315 | |
| gtg gga gat att cct tat gga gtt cct cag gat tct aca aga gca agt<br>Val Gly Asp Ile Pro Tyr Gly Val Pro Gln Asp Ser Thr Arg Ala Ser<br>                   320                     325                     330 | 1193 |
| caa gga aca tct aca tgc ctg caa gag tca ctt ggg gaa tgt ttt tct<br>Gln Gly Thr Ser Thr Cys Leu Gln Glu Ser Leu Gly Glu Cys Phe Ser<br>335                     340                     345 | 1241 |
| gaa aaa gac cct agg gag gta cca ggg ttg cag tct agg caa gag cag<br>Glu Lys Asp Pro Arg Glu Val Pro Gly Leu Gln Ser Arg Gln Glu Gln<br>         350                     355                     360 | 1289 |
| ctt atc tct gat cct gtc ctt ctt ggt aag aat cat gag gca aac tta<br>Leu Ile Ser Asp Pro Val Leu Leu Gly Lys Asn His Glu Ala Asn Leu<br>365                     370                     375 | 1337 |
| cca tgt gaa agt cat caa aag aga ttc tgt aga gat gcc aaa cta tac<br>Pro Cys Glu Ser His Gln Lys Arg Phe Cys Arg Asp Ala Lys Leu Tyr<br>380                     385                     390                     395 | 1385 |
| aag tgt gaa gaa tgt tct agg atg ttc aaa cat gcc agg agc ctt tca<br>Lys Cys Glu Glu Cys Ser Arg Met Phe Lys His Ala Arg Ser Leu Ser<br>                   400                     405                     410 | 1433 |
| tcc cac cag aga act cac ctg aat aag aag agt gaa ttg ctt tgt gtc<br>Ser His Gln Arg Thr His Leu Asn Lys Lys Ser Glu Leu Leu Cys Val<br>               415                     420                     425 | 1481 |
| acc tgt cag aaa atg ttc aaa cga gtc tct gac cgc cga acc cat gag<br>Thr Cys Gln Lys Met Phe Lys Arg Val Ser Asp Arg Arg Thr His Glu<br>         430                     435                     440 | 1529 |
| atc ata cac atg cca gaa aag cct ttc aag tgc agc aca tgt gaa aag<br>Ile Ile His Met Pro Glu Lys Pro Phe Lys Cys Ser Thr Cys Glu Lys<br>445                     450                     455 | 1577 |
| tcc ttc agc cac aag acc aac ctg aag tct cat gag atg att cac aca<br>Ser Phe Ser His Lys Thr Asn Leu Lys Ser His Glu Met Ile His Thr<br>460                     465                     470                     475 | 1625 |
| gga gaa atg cct tat gtc tgt tcc cta tgt agc cgt cgc ttt cgc caa<br>Gly Glu Met Pro Tyr Val Cys Ser Leu Cys Ser Arg Arg Phe Arg Gln<br>                   480                     485                     490 | 1673 |
| tca tcc act tac cat cgt cac ctg agg aat tac cac aga tct gac tga<br>Ser Ser Thr Tyr His Arg His Leu Arg Asn Tyr His Arg Ser Asp<br>               495                     500                     505 | 1721 |
| actatctaac atcctcagca gagactggta gggcttcagc ctcagtatgt catcttcaaa | 1781 |
| gagagaagaa tgttgcaagt aaattgtact gtcccaataa tgatataaca tgcttgtgga | 1841 |
| ttgccacttt tatgttttgt tttgttttt attttgtgtg tgtgtgtatg taatttttg | 1901 |
| tctgtatttc catagttcca cagcataagt tattagaata ctttgctgtt aattcttgag | 1961 |
| ttgcttcttg cttttagaca gtgtctttct ggttgacagc tttataaacc tgtctttctg | 2021 |
| gcactagagt ttccaaacat tttctgatct ccacttttat tctctacagt gttcttgaca | 2081 |
| gaagcctggc attccctctg acatttttct acatgttggg gttttcatcc caagtcttag | 2141 |
| ggttgcaagt taaatgcatt gcctcttcag acatctcatg ccctgtctac tgcttacagt | 2201 |
| tcaagaatat ttctctacat tactagaacg acattcaaag tggaataata aataaataaa | 2261 |
| taatcaacaa tt | 2273 |

<210> SEQ ID NO 35
<211> LENGTH: 506
<212> TYPE: PRT
<213> ORGANISM: Mus musculus

<400> SEQUENCE: 35

-continued

```
Met Ala Ser Gln Gln Ala Pro Ala Lys Asp Leu Gln Thr Asn Asn Leu
1               5                   10                  15
Glu Phe Thr Pro Thr Asp Ser Ser Gly Val Gln Trp Ala Glu Asp Ile
            20                  25                  30
Ser Asn Ser Pro Ser Ala Gln Leu Asn Phe Ser Pro Ser Asn Asn Gly
        35                  40                  45
Cys Trp Ala Thr Gln Glu Leu Gln Ser Leu Trp Lys Met Phe Asn Ser
50                  55                  60
Trp Leu Gln Pro Glu Lys Gln Thr Lys Glu Gln Met Ile Ser Gln Leu
65                  70                  75                  80
Val Leu Glu Gln Phe Leu Leu Thr Gly His Cys Lys Asp Lys Tyr Ala
                85                  90                  95
Leu Thr Glu Lys Trp Lys Ala Ser Gly Ser Asp Met Arg Arg Phe Met
            100                 105                 110
Glu Ser Leu Thr Asp Glu Cys Leu Lys Pro Val Met Val His Val
        115                 120                 125
Ser Met Gln Gly Gln Glu Ala Leu Phe Ser Glu Asn Met Pro Leu Lys
    130                 135                 140
Glu Val Ile Lys Leu Leu Lys Gln Gln Ser Ala Thr Arg Pro Thr
145                 150                 155                 160
Pro Asp Asn Glu Gln Met Pro Val Asp Thr Thr Gln Asp Arg Leu Leu
                165                 170                 175
Ala Thr Gly Gln Glu Asn Ser Glu Asn Glu Cys Asn Asn Ser Cys Asn
            180                 185                 190
Ala Thr Glu Ala Asn Val Gly Val Ser Cys Ser Gly Asn Glu Met Asp
        195                 200                 205
Ser Leu Leu Ile Met Gln Lys Glu Gln His Pro Glu His Glu Glu Gly
    210                 215                 220
Asn Val Val Cys Gln Phe Pro His Gly Ala Arg Arg Ala Ser Gln Gly
225                 230                 235                 240
Thr Pro Ser His His Val Asp Phe Pro Ser Ala Pro Thr Thr Ala Asp
                245                 250                 255
Val Pro Met Glu Glu Gln Pro Lys Asp Leu Ser Arg Glu Asn Ile Ser
            260                 265                 270
Glu Asp Lys Asn Asn Cys Tyr Asn Thr Ser Arg Asn Ala Ala Thr Gln
        275                 280                 285
Val Tyr Ser Gly Asp Asn Ile Pro Arg Asn Lys Ser Asp Ser Leu Phe
    290                 295                 300
Ile Asn Lys Arg Ile Tyr His Pro Glu Pro Glu Val Gly Asp Ile Pro
305                 310                 315                 320
Tyr Gly Val Pro Gln Asp Ser Thr Arg Ala Ser Gln Gly Thr Ser Thr
                325                 330                 335
Cys Leu Gln Glu Ser Leu Gly Glu Cys Phe Ser Glu Lys Asp Pro Arg
            340                 345                 350
Glu Val Pro Gly Leu Gln Ser Arg Gln Glu Gln Leu Ile Ser Asp Pro
        355                 360                 365
Val Leu Leu Gly Lys Asn His Glu Ala Asn Leu Pro Cys Glu Ser His
    370                 375                 380
Gln Lys Arg Phe Cys Arg Asp Ala Lys Leu Tyr Lys Cys Glu Glu Cys
385                 390                 395                 400
Ser Arg Met Phe Lys His Ala Arg Ser Leu Ser Ser His Gln Arg Thr
                405                 410                 415
His Leu Asn Lys Lys Ser Glu Leu Leu Cys Val Thr Cys Gln Lys Met
```

```
                420             425             430
Phe Lys Arg Val Ser Asp Arg Arg Thr His Glu Ile Ile His Met Pro
            435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
                500                 505

<210> SEQ ID NO 36
<211> LENGTH: 2260
<212> TYPE: DNA
<213> ORGANISM: Homo sapiens
<220> FEATURE:
<221> NAME/KEY: CDS
<222> LOCATION: (698)..(1999)

<400> SEQUENCE: 36
ccttgtaatt cataaatctc tgaaaactta aaagtttgag caaaagtttg tcatgtttct      60
atgagtaatt tataataaaa cttgatcaga atttgtgaga ctaacgtttg tctttatatt    120 ttccttttt tttttttttt ttttgagaca cagtctcgct ctgtcgtcca ggctggagtg    180
ccgtggcgta atctcggctc actgcaacct ctgcctcctg gattcaaaca attcttctgc    240
ctcagcctcc tgagtagctg ggattacagg accagtgatg gtatagaaca ctgtattaga    300
gacatggagc tggggctgga tgaagattcc atcagtaatt caatcaacag acaagtgtta    360
tccaatcacg tctttaaatc aatcactgac atggagctgg ggctggatga agattccatc    420
agtaattcaa tcaacagaca gtgttatcc aatcacgtct ttaaatcaat cactgatccc    480
agcccctata aagggagca gccttaggag gcacatcaga taaacccagt gtggaaagct    540
agtcacacat cagctcagtg ttcggcccgg gattacccag tcaaccaagg agcttgcagt    600
tttaaagaat ccaccaactg ttgaaacaaa tccctagaga cacaaggcaa agagactgaat   660 catcaaagta aagtctctct gagaattatt gctaaga atg gct tta gat cta aga    715
                                            Met Ala Leu Asp Leu Arg
                                            1               5 acc ata ttt cag tgt gaa cca tcc gag aat aat ctt gga tca gaa aat    763
Thr Ile Phe Gln Cys Glu Pro Ser Glu Asn Asn Leu Gly Ser Glu Asn
        10                  15                  20 tca gcg ttt caa caa agc caa gga cct gct gtt cag aga gaa gaa ggg    811
Ser Ala Phe Gln Gln Ser Gln Gly Pro Ala Val Gln Arg Glu Glu Gly
    25                  30                  35 att tct gag ttc tca aga atg gtg ctc aat tca ttt caa gac agc aat    859
Ile Ser Glu Phe Ser Arg Met Val Leu Asn Ser Phe Gln Asp Ser Asn
40                  45                  50 aat tca tat gca agg cag gaa ttg caa aga ctt tat agg atc ttt cac    907
Asn Ser Tyr Ala Arg Gln Glu Leu Gln Arg Leu Tyr Arg Ile Phe His
55                  60                  65                  70 tca tgg ctg caa cca gaa aag cac agc aag gat gaa att att tct cta    955
Ser Trp Leu Gln Pro Glu Lys His Ser Lys Asp Glu Ile Ile Ser Leu
            75                  80                  85 tta gtc ctg gag cag ttt atg att ggt ggc cac tgc aat gac aaa gcc   1003
Leu Val Leu Glu Gln Phe Met Ile Gly Gly His Cys Asn Asp Lys Ala
        90                  95                  100 agt gtg aaa gag aaa tgg aaa tca agt ggc aaa aac ttg gag aga ttc   1051
```

```
Ser Val Lys Glu Lys Trp Lys Ser Gly Lys Asn Leu Glu Arg Phe
        105                 110                 115 ata gaa gac ctg act gat gac agc ata aat cca cct gcc tta gtc cac    1099
Ile Glu Asp Leu Thr Asp Asp Ser Ile Asn Pro Pro Ala Leu Val His
120                 125                 130 gtc cac atg cag gga cag gaa gct ctc ttt tct gag gat atg ccc tta    1147
Val His Met Gln Gly Gln Glu Ala Leu Phe Ser Glu Asp Met Pro Leu
135                 140                 145                 150 aga gat gtc att gtt cat ctc aca aaa caa gtg aat gcc caa acc aca    1195
Arg Asp Val Ile Val His Leu Thr Lys Gln Val Asn Ala Gln Thr Thr
        155                 160                 165 aga gaa gca aac atg ggg aca ccc tcc cag act tcc caa gat act tcc    1243
Arg Glu Ala Asn Met Gly Thr Pro Ser Gln Thr Ser Gln Asp Thr Ser
        170                 175                 180 tta gaa aca gga caa gga tat gaa gat gaa caa gat ggc tgg aac agt    1291
Leu Glu Thr Gly Gln Gly Tyr Glu Asp Glu Gln Asp Gly Trp Asn Ser
        185                 190                 195 tct tcg aaa act act cga gta aat gaa aat att act aat caa ggc aat    1339
Ser Ser Lys Thr Thr Arg Val Asn Glu Asn Ile Thr Asn Gln Gly Asn
200                 205                 210 caa ata gtt tcc cta atc atc atc cag gaa gag aac ggt cct agg cct    1387
Gln Ile Val Ser Leu Ile Ile Ile Gln Glu Glu Asn Gly Pro Arg Pro
215                 220                 225                 230 gaa gag gga ggt gtt tct tct gac aac cca tac aac tca aaa aga gca    1435
Glu Glu Gly Gly Val Ser Ser Asp Asn Pro Tyr Asn Ser Lys Arg Ala
                235                 240                 245 gag cta gtc act gct aga tct cag gaa ggg tcc ata aat gga atc act    1483
Glu Leu Val Thr Ala Arg Ser Gln Glu Gly Ser Ile Asn Gly Ile Thr
        250                 255                 260 ttc caa ggt gtc cct atg gtg atg gga gca ggg tgt atc tct caa cca    1531
Phe Gln Gly Val Pro Met Val Met Gly Ala Gly Cys Ile Ser Gln Pro
        265                 270                 275 gag cag tcc tcc cct gag tct gcc ctt acc cac cag agc aat gag gga    1579
Glu Gln Ser Ser Pro Glu Ser Ala Leu Thr His Gln Ser Asn Glu Gly
            280                 285                 290 aat tcc aca tgt gag gta cat cag aaa gga tcc cat gga gtc caa aaa    1627
Asn Ser Thr Cys Glu Val His Gln Lys Gly Ser His Gly Val Gln Lys
295                 300                 305                 310 tca tac aaa tgt gaa gaa tgc ccc aag gtc ttt aag tat ctc tgt cac    1675
Ser Tyr Lys Cys Glu Glu Cys Pro Lys Val Phe Lys Tyr Leu Cys His
                315                 320                 325 tta tta gct cac cag aga aga cac agg aat gag agg cca ttt gtt tgt    1723
Leu Leu Ala His Gln Arg Arg His Arg Asn Glu Arg Pro Phe Val Cys
        330                 335                 340 ccc gag tgt caa aaa ggc ttc ttc cag ata tca gac cta cgg gtg cat    1771
Pro Glu Cys Gln Lys Gly Phe Phe Gln Ile Ser Asp Leu Arg Val His
        345                 350                 355 cag ata att cac aca gga aag aag cct ttc aca tgc agc atg tgt aaa    1819
Gln Ile Ile His Thr Gly Lys Lys Pro Phe Thr Cys Ser Met Cys Lys
360                 365                 370 aag tcc ttc agc cac aaa acc aac ctg cgg tct cat gag aga atc cac    1867
Lys Ser Phe Ser His Lys Thr Asn Leu Arg Ser His Glu Arg Ile His
375                 380                 385                 390 aca gga gaa aag cct tat aca tgt ccc ttt tgt aag aca agc tac cgc    1915
Thr Gly Glu Lys Pro Tyr Thr Cys Pro Phe Cys Lys Thr Ser Tyr Arg
                395                 400                 405 cag tca tcc aca tac cac cgc cat atg agg act cat gag aaa att acc    1963
Gln Ser Ser Thr Tyr His Arg His Met Arg Thr His Glu Lys Ile Thr
        410                 415                 420
```

|  |  |  |  |  |  |  |  | | |
|---|---|---|---|---|---|---|---|---|---|
| ctg | cca | agt | gtt | ccc | tcc | aca | cca | gaa gct tcc taa gctgctggtc | 2009 |
| Leu | Pro | Ser | Val | Pro | Ser | Thr | Pro | Glu Ala Ser | |
|     |     | 425 |     |     |     |     | 430 |     | | tgataatgtg tataaatatg tatgcaagta tgtatattcc tatagtattt atctacttag     2069 gatataagat ataatctcct gattatgctt tcaatttatt gtcttgcttc attaaaatgt     2129 aaggctaagg agagcatgga atttgtcagt tttgttcact aaagtattcc aagtggttgg     2189 gaaagtggaa catttccaag aaccaataaa tttctgttga ataaatgaat gaatccaaaa     2249 aaaaaaaaaa a     2260

<210> SEQ ID NO 37
<211> LENGTH: 433
<212> TYPE: PRT
<213> ORGANISM: Homo sapiens

<400> SEQUENCE: 37

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Ser Val Lys Glu Lys Trp Lys Ser Ser Gly
            100                 105                 110

Lys Asn Leu Glu Arg Phe Ile Glu Asp Leu Thr Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Lys Thr Thr Arg Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Pro Glu Glu Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

```
Ser His Gly Val Gln Lys Ser Tyr Lys Cys Glu Cys Pro Lys Val
305                 310                 315                 320

Phe Lys Tyr Leu Cys His Leu Leu Ala His Gln Arg Arg His Arg Asn
            325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
            355                 360                 365

Thr Cys Ser Met Cys Lys Lys Ser Phe Ser His Lys Thr Asn Leu Arg
        370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
            405                 410                 415

Thr His Glu Lys Ile Thr Leu Pro Ser Val Pro Ser Thr Pro Glu Ala
            420                 425                 430

Ser

<210> SEQ ID NO 38
<211> LENGTH: 9396
<212> TYPE: DNA
<213> ORGANISM: Artificial Sequence
<220> FEATURE:
<223> OTHER INFORMATION: Zscan4-Emerald expression vector

<400> SEQUENCE: 38
cgcatagtta agccagtatc tgctccctgc ttgtgtgttg aggtcgctg  agtagtgcgc      60 gagcaaaatt taagctacaa caaggcaagg cttgaccgac aattgcatga agaatctgct    120
tagggttagg cgttttgcgc tgcttcgcga tgtacgggcc agatatacgc gttgacattg    180
attattgact agttattaat agtaatcaat tacgggtca ttagttcata gcccatatat     240
ggagttccgc gttacataac ttacggtaaa tggcccgcct ggctgaccgc ccaacgaccc    300
ccgcccattg acgtcaataa tgacgtatgt tcccatagta acgccaatag ggactttcca    360
ttgacgtcaa tgggtggagt atttacggta aactgcccac ttggcagtac atcaagtgta    420
tcatatgcca agtacgcccc ctattgacgt caatgacggt aaatggcccg cctggcatta    480
tgcccagtac atgaccttat gggactttcc tacttggcag tacatctacg tattagtcat    540
cgctattacc atggtgatgc ggttttggca gtacatcaat gggcgtggat agcggtttga    600
ctcacgggga tttccaagtc tccaccccat tgacgtcaat gggagtttgt tttggcacca    660
aaatcaacgg gactttccaa aatgtcgtaa caactccgcc ccattgacgc aaatgggcgg    720
taggcgtgta cggtgggagg tctatataag cagagctctc tggctaacta gagaacccac    780
tgcttactgg cttatcgaaa ttaatacgac tcactatagg gagacccaag ctggctagtt    840
aagctgagca tcaacaagtt tgtacaaaaa agcaggctcc gaattcgccc ttgacgcgcg    900
acgcgtgtcc tgctattctg tgcattgaaa catgtcatgt ctgtgtccct gatgttttac    960
ttgaagaata tggcatacaa gttccttctt ctttgcttta tagaatatat tttaaattat   1020
aataatttcc tctctaaaat aatgtttttg ttaagaccta ttaatttgtt ataaattttg   1080
ttgggattac aaatactttt ctgagaaaag tttgcatgtt gtacaaactc tattcatata   1140 aaatacctt  tcatacaaaa gaagaattgc tgttttatcc ccattctaac tcttagtata   1200
aataaaataa tgcagtgggt tgttctgatg ctgcttatat tatcatgcta aatattggct   1260
tcttaatctg tggtcgtcca caaagtacag agccacacat ccaccaaatg atgttatttg   1320
```

```
aatattgtcc cgaaatacaa ctggttaaaa aaaaaaaaaa aaaaaaaagc aacttgctat   1380
gactggtcat ctaagggaga aaggtggaat ttgaggatta agtgaagaga ttgctggtag   1440
aggaagagaa agaagaaaga agacttaagc ggagatggtt gccatgggaa gagatgaaat   1500
ataaattctt ggaacagaga aatagcaagt ataagggact tgatcgttgg ggaataagct   1560
gaaatagctg taaatctgcc ttatttaggc ttgagtttgt aaataaaata gctagattgt   1620
gttttttttt atatggacaa gctagcatta tggatcccct ccaacagcaa caaccaataa   1680
atgatttaaa agcatggctt ctaccttcct agtagtagcg gttccaggac aaccttactt   1740
ctatcatctt tttcttcttc ttcttcttga tgcttttgtg cttttttttt tttttttttt   1800
tttttttttt ttttttttt ttttggtgac accttctgtt catgcaagcc tggctatgtt   1860
tgagctctat ttgaaatcca gacttgcctc aaagtgatag agatgcttct gcatctgttt   1920
tctgatctag gattaagtgt gtagcaggga ttaaaggcac taacctcctt caagtaatct   1980
aattgctaaa ttgaattgtg cccttgaaat tcactttcag gaagaaaata gtgaacaaca   2040
gtaaagtgtt tattgttctc atgaaaaaac actttcatct gaatgtttct tcttgttagt   2100
attgcattaa ttcattaata tactgaacat catcaatagc aaaaaaaaaa caaatgatac   2160 attttttacat ggtgagtcaa tcattgttgt aacaaatggc taattcattt gaagaatttg   2220
tagtgctttc tttgtcatgt ggcattttt ttccataaa gggaagggca gctttaggtt   2280
taagcattca aaatttatgg ttttgtgaat gtaaaaaatt ttagaagttg taaatcactg   2340
attttccatc ctatttgggg taagggaaaa taaggttcta tgttttggac tgaagtttag   2400
cacaatctca gtgtttgaag ataaaacatc aacatgtgaa tttaggggtc acaattgaac   2460
ctatcaatta gcatgattgg acaaagcaat tcacaaaggc aaccacgttt aaatccacca   2520
ctctggaatt aatggcaagg atgtgtcaac ctgatccaca ctgtagggct attatgtcta   2580
ggcatacaag ggaaaaaaat tgtctctaga tgaagtaaaa gaaaacagag acagaaaaac   2640 aaaaggatg tgtgaagtag tgaggtcact ctgggatgtc agcactgagg agttaaaagt   2700
tatatgattg tagtgcaaga tcattctgaa caagttagtg agattgtgag cagactagga   2760
taccatatag acacttgtaa aaaaacaaac aaaacaaaaa acaaatgaac aaaccaaaca   2820
tgagagagag atggaaagat agagaaaaca agagagaaca acaaagacca ccacattttg   2880
ccacaaattt taatctctcc ctagaataca gtcctcatat gatgtccatg ttttcgcaat   2940
aggcaatgca cattcctctc taccaaaaga tacaagttcc cttcagcctc catctttact   3000
atattgtgct acagacacct tatggattct tcctgcccta tctgatccca ctatcaagga   3060
ttctacagag ttcactgaag cacttagggt ccaatctctc tagaaaccag gaaattttaa   3120
caagttttca ttgactacta tgtgagaaca caggatcaga ggtcatagaa gataaatgcc   3180
aatcttggaa ttcctcttca gtgtggtact atttccattc actacagtga cttacaacac   3240
ttgactagga gatgatcttc ttccaaagaa gagtcaatca ttgcattaga gatgcaaaac   3300
tagagctgag ttaggattcc ttatgtgatt caatcagcag gaaaaaatgt ctttccttat   3360
tttgtttgct tgcttgtatt tgattccccc ttttggcatt atctgttcct ctgggtcaga   3420
ctgaccttgg atctctgggc ttaataggca gtgctgggga ctactgactc tcctgattca   3480
atttctatta ctttgagtac tatggataaa atggtaatct gccccaccca ggaacaggag   3540
ttttgataga atcactgtgt gaatttaatc gtcatcagta actgactaac ggaagccagg   3600
cgctataaaa gggaaccaat cctaatagaa cctcagatga agcagagcca aggcagagac   3660
```

```
acacagtgcc tccctgggct tcttggcatc acccttgaag ttcaccggag aaagcagtga    3720
ggtggaggaa taggtaaact ttccttccta gtggtcttga atgtgtaagt atatgtgtat    3780
ttatgtgtgt gtatgtgtgt ttatttgtgg acttgtgaga agattcatca caattatggg    3840
gagatctcag tagttcaata ttgccttttg gaagctttcc tgatcaagag gttgatttt    3900
ctaaactcta agaaaactc tgagttggta atcattcagg tatgtgcgtg gatatttgtt    3960
tgcctctctg tgaatttaat attcctgatt attcatttta aatattttct tatgaaagta    4020
ttattctctg gtgctttaga atgagacaga agggtgaaac ttaaaatttg aggaacagca    4080
gaataactcc catcttttcc aaaggggaa cagacaacat tgctgtgttc ttaagatctc    4140
atgacagatc taagcaccct agatacagga cttttctggtt attgagtcaa tttttttttct    4200
acttttcagt tgttttgccc atttccaatt ccatgcaagc agattgaaag gactatagtg    4260
aaacatttac tgtcaggaac ccataaaacc atctgtgaca caaatctcat ttggttttgt    4320
gtttgttttg ttaacattaa ttatgtgttt cttccttttt taaattcaca gcttttacag    4380
tacatccatc aactgttagc attttcgtaa agtcacaaaa cagatattaa actactatag    4440
ttgaatcttt cacaccattg tcaccacagt taacaagggc gaattcgacc cagctttctt    4500
gtacaaagtg gttgatgctg ttaacatggt gagcaagggc gaggagctgt tcaccggggt    4560
ggtgcccatc ctggtcgagc tggacggcga cgtaaacggc cacaagttca gcgtgtccgg    4620
cgagggcgag ggcgatgcca cctacggcaa gctgaccctg aagttcatct gcaccaccgg    4680
caagctgccc gtgccctggc ccaccctcgt gaccaccttc acctacggcg tgcagtgctt    4740
cgcccgctac cccgaccaca tgaagcagca cgacttcttc aagtccgcca tgcccgaagg    4800
ctacgtccag gagcgcacca tcttcttcaa ggacgacggc aactacaaga cccgcgccga    4860
ggtgaagttc gagggcgaca ccctggtgaa ccgcatcgag ctgaagggca tcgacttcaa    4920
ggaggacggc aacatcctgg ggcacaagct ggagtacaac tacaacagcc acaaggtcta    4980
tatcaccgcc gacaagcaga agaacggcat caaggtgaac ttcaagaccc gccacaacat    5040
cgaggacggc agcgtgcagc tcgccgacca ctaccagcag aacacccca tcggcgacgg    5100
ccccgtgctg ctgcccgaca accactacct gagcacccag tccgccctga gcaaagaccc    5160
caacgagaag cgcgatcaca tggtcctgct ggagttcgtg accgccgccg ggatcactct    5220
cggcatggac gagctgtaca gtaatgata agtttaaacg ggggaggcta actgaaacac    5280
ggaaggagac aataccggaa ggaacccgcg ctatgacggc aataaaaaga cagaataaaa    5340
cgcacggtg ttgggtcgtt tgttcataaa cgcggggttc ggtcccaggg ctggcactct    5400
gtcgataccc caccgagacc ccattgggc caatacgccc gcgtttcttc cttttcccca    5460
ccccacccc caagttcggg tgaaggccca gggctcgcag ccaacgtcgg ggcggcaggc    5520
cctgccatag cagatctgcg cagctggggc tctaggggggt atccccacgc gccctgtagc    5580
ggcgcattaa gcgcggcggg tgtggtggtt acgcgcagcg tgaccgctac acttgccagc    5640
gccctagcgc ccgctccttt cgctttcttc ccttcctttc tcgccacgtt cgccggcttt    5700
ccccgtcaag ctctaaatcg ggggctccct ttagggttcc gatttagtgc tttacggcac    5760
ctcgacccca aaaaacttga ttagggtgat ggttcacgta gtgggccatc gccctgatag    5820
acggttttc gccctttgac gttggagtcc acgttcttta atagtggact cttgttccaa    5880
actggaacaa cactcaaccc tatctcggtc tattcttttg atttataagg gattttgccg    5940
atttcggcct attggttaaa aaatgagctg atttaacaaa aatttaacgc gaattaattc    6000
tgtggaatgt gtgtcagtta gggtgtggaa agtccccagg ctccccagca ggcagaagta    6060
```

```
tgcaaagcat gcatctcaat tagtcagcaa ccaggtgtgg aaagtcccca ggctccccag   6120
caggcagaag tatgcaaagc atgcatctca attagtcagc aaccatagtc ccgcccctaa   6180
ctccgcccat cccgccccta actccgccca gttccgccca ttctccgccc catggctgac   6240 taatttttt tatttatgca gaggccgagg ccgcctctgc ctctgagcta ttccagaagt    6300
agtgaggagg cttttttgga ggcctaggct tttgcaaaaa gctcccggga gcttgtatat   6360
ccattttcgg atctgatcag cacgtgttga caattaatca tcggcatagt atatcggcat   6420
agtataatac gacaaggtga ggaactaaac catggccaag cctttgtctc aagaagaatc   6480
caccctcatt gaaagagcaa cggctacaat caacagcatc cccatctctg aagactacag   6540
cgtcgccagc gcagctctct ctagcgacgg ccgcatcttc actggtgtca atgtatatca   6600
ttttactggg ggaccttgtg cagaactcgt ggtgctgggc actgctgctg ctgcggcagc   6660
tggcaacctg acttgtatcg tcgcgatcgg aaatgagaac aggggcatct tgagcccctg   6720
cggacggtgc cgacaggtgc ttctcgatct gcatcctggg atcaaagcca tagtgaagga   6780
cagtgatgga cagccgacgg cagttgggat tcgtgaattg ctgccctctg gttatgtgtg   6840
ggagggctaa gcacttcgtg gccgaggagc aggactgaca cgtgctacga gatttcgatt   6900
ccaccgccgc cttctatgaa aggttgggct tcggaatcgt tttccgggac gccggctgga   6960
tgatcctcca gcgcggggat ctcatgctgg agttcttcgc ccaccccaac ttgtttattg   7020
cagcttataa tggttacaaa taaagcaata gcatcacaaa tttcacaaat aaagcatttt   7080
tttcactgca ttctagttgt ggtttgtcca aactcatcaa tgtatcttat catgtctgta   7140
taccgtcgac ctctagctag agcttggcgt aatcatggtc atagctgttt cctgtgtgaa   7200
attgttatcc gctcacaatt ccacacaaca tacgagccgg aagcataaag tgtaaagcct   7260
ggggtgccta atgagtgagc taactcacat taattgcgtt gcgctcactg cccgctttcc   7320
agtcgggaaa cctgtcgtgc cagctgcatt aatgaatcgg ccaacgcgcg gggagaggcg   7380
gtttgcgtat tgggcgctct tccgcttcct cgctcactga ctcgctgcgc tcggtcgttc   7440
ggctgcggcg agcggtatca gctcactcaa aggcggtaat acggttatcc acagaatcag   7500
gggataacgc aggaaagaac atgtgagcaa aaggccagca aaaggccagg aaccgtaaaa   7560
aggccgcgtt gctggcgttt ttccataggc tccgcccccc tgacgagcat cacaaaaatc   7620
gacgctcaag tcagaggtgg cgaaacccga caggactata agataccagg cgtttccccc   7680
ctggaagctc cctcgtgcgc tctcctgttc cgaccctgcc gcttaccgga tacctgtccg   7740
cctttctccc ttcgggaagc gtggcgcttt ctcatagctc acgctgtagg tatctcagtt   7800
cggtgtaggt cgttcgctcc aagctgggct gtgtgcacga accccccgtt cagcccgacc   7860
gctgcgcctt atccggtaac tatcgtcttg agtccaaccc ggtaagacac gacttatcgc   7920
cactggcagc agccactggt aacaggatta gcagagcgag gtatgtaggc ggtgctacag   7980
agttcttgaa gtggtggcct aactacggct acactagaag aacagtattt ggtatctgcg   8040
ctctgctgaa gccagttacc ttcggaaaaa gagttggtag ctcttgatcc ggcaaacaaa   8100
ccaccgctgg tagcggtggt ttttttgttt gcaagcagca gattacgcgc agaaaaaaag   8160
gatctcaaga agatcctttg atcttttcta cggggtctga cgctcagtgg aacgaaaact   8220
cacgttaagg gattttggtc atgagattat caaaaaggat cttcacctag atccttttaa   8280
attaaaaatg aagttttaaa tcaatctaaa gtatatatga gtaaacttgg tctgacagtt   8340
accaatgctt aatcagtgag gcacctatct cagcgatctg tctatttcgt tcatccatag   8400
```

```
ttgcctgact ccccgtcgtg tagataacta cgatacggga gggcttacca tctggcccca    8460
gtgctgcaat gataccgcga gacccacgct caccggctcc agatttatca gcaataaacc    8520
agccagccgg aagggccgag cgcagaagtg gtcctgcaac tttatccgcc tccatccagt    8580
ctattaattg ttgccgggaa gctagagtaa gtagttcgcc agttaatagt ttgcgcaacg    8640
ttgttgccat tgctacaggc atcgtggtgt cacgctcgtc gtttggtatg gcttcattca    8700
gctccggttc ccaacgatca aggcgagtta catgatcccc catgttgtgc aaaaaagcgg    8760
ttagctcctt cggtcctccg atcgttgtca gaagtaagtt ggccgcagtg ttatcactca    8820
tggttatggc agcactgcat aattctctta ctgtcatgcc atccgtaaga tgcttttctg    8880
tgactggtga gtactcaacc aagtcattct gagaatagtg tatgcggcga ccgagttgct    8940 cttgccggc gtcaatacgg gataataccg cgccacatag cagaacttta aaagtgctca    9000
tcattggaaa acgttcttcg gggcgaaaac tctcaaggat cttaccgctg ttgagatcca    9060
gttcgatgta acccactcgt gcacccaact gatcttcagc atctttact ttcaccagcg    9120 tttctgggtg agcaaaaaca ggaaggcaaa atgccgcaaa aaagggaata agggcgacac    9180
ggaaatgttg aatactcata ctcttccttt ttcaatatta ttgaagcatt tatcagggtt    9240
attgtctcat gagcggatac atatttgaat gtatttagaa aaataaacaa atagggggttc   9300 cgcgcacatt tccccgaaaa gtgccacctg acgtcgacgg atcgggagat ctcccgatcc    9360
cctatggtgc actctcagta caatctgctc tgatgc                              9396
```

<210> SEQ ID NO 39
<211> LENGTH: 15
<212> TYPE: PRT
<213> ORGANISM: Homo sapiens

<400> SEQUENCE: 39

```
Leu Gln Thr Asn Asn Leu Glu Phe Thr Pro Thr Asp Ser Ser Cys
1               5                   10                  15
```

METHODS FOR ENHANCING GENOME STABILITY AND TELOMERE ELONGATION IN EMBRYONIC STEM CELLS

CROSS REFERENCE TO RELATED APPLICATIONS

This is a continuation of U.S. application Ser. No. 13/393,456, filed Feb. 29, 2012, issued as U.S. Pat. No. 8,741,649 on Jun. 3, 2014, which is the U.S. National Stage of International Application No. PCT/US2010/047644, filed Sep. 2, 2010, published in English under PCT Article 21(2), which claims the benefit of U.S. Provisional Application No. 61/275,983, filed Sep. 4, 2009. The above-listed applications are herein incorporated by reference in their entirety.

FIELD

This disclosure relates to embryonic stem (ES) cells and induced pluripotent stem (iPS) cells and the role of Zscan4 expression in promoting genome stability and telomere elongation in ES and iPS cells.

BACKGROUND

Mouse embryonic stem (ES) cells are derived from the inner cell mass (ICM) of blastocysts and share similar gene expression patterns with the ICM. The defining features of ES cells are pluripotency and self-renewal, both of which have been the focus of intensive research for many years. Another hallmark of mouse ES cells is their ability to defy cellular senescence and to proliferate more than 250 doublings without crisis or transformation (Suda et al., *J Cell Physiol* 133:197-201, 1987). Although the fraction of euploid cells tends to decrease in long-term culture (Rebuzzini et al., *Cytotechnology* 58:17-23, 2008), the genome integrity of mouse ES cells is more strictly maintained than any other cultured cells. For example, ES cells maintain their ability to form chimeric animals with germline competency even after many passages (Longo et al., *Transgenic Res* 6:321-328, 1997; Nagy et al., *Proc Natl Acad Sci USA* 90:8424-8428, 1993; Sugawara et al., *Comp Med* 56:31-34, 2006). The mutation frequency in ES cells is also much lower (>100-fold) than those in mouse embryonic fibroblast cells and other somatic cells (Cervantes et al., *Proc Natl Acad Sci USA* 99:3586-3590, 2002). The unique feature of mouse ES cells can be further highlighted by a lower frequency of chromosomal abnormalities compared to embryonal carcinoma cells, which share similar characteristics to ES cells (Blelloch et al., *Proc Natl Acad Sci USA* 101:13985-13990, 2004), as well as some human ES cells (Brimble et al., *Stem Cells Dev* 13:585-597, 2004). However, the mechanism by which mouse ES cells maintain genomic stability is currently poorly understood.

Telomeres are repetitive DNA sequences accompanied by proteins that cap and protect the end of each chromosome from continuous degradation in each cell cycle, thereby securing and protecting chromosomal integrity. Telomere shortening may lead to cancer by contributing to genomic instability (Raynaud et al., *Crit. Rev Oncol Hematol* 66:99-117, 2008), and has been associated with aging and cellular senescence (Yang, *Cytogenet Genome Res* 122:211-218, 2008). Telomerase has been identified as the major enzyme known to be involved in telomere elongation maintenance. Although telomerase is active in ES cells (Thomson et al., *Science* 282:1145-1147, 1998), telomerase knockout ES cells (Terc$^{-/-}$) show a marked reduction in telomere length only after 400 cell doublings, reaching a dramatic senescence event 10-30 doublings later, followed by establishment of a telomerase-independent population with no marked short telomeres (Niida et al., *Nat Genet.* 19:203-206, 1998; Niida et al., *Mol Cell Biol* 20:4115-4127, 2000). Hence, a telomerase-independent mechanism for telomere maintenance, named alternative lengthening of telomeres (ALT) (Bryan et al., *EMBO J.* 14:4240-4248, 1995), has been suggested for Terc$^{-/-}$ ES cells. Apparently, telomere recombination, or telomere sister chromatid exchange (T-SCE) can compensate for the lack of telomerase activity. Indeed, an increased frequency of T-SCE events has been demonstrated in long-term cultures of Terc$^{-/-}$ ES cells (Bailey et al., *Nucleic Acids Res* 32:3743-3751, 2004; Wang et al., *Proc Natl Acad Sci USA* 102:10256-10260, 2005).

Additionally, telomere recombination appears to be a normal mechanism in preimplantation embryos. Even though enzymatic activity of telomerase cannot be detected in preimplantation embryos from the unfertilized oocyte stage to the blastocyst stage (Wright et al., *Dev Genet.* 18:173-179, 1996), telomere length is rapidly increased during this period. In just one cell cycle, the average telomere length of 2-cell stage mouse embryos is doubled compared to that of unfertilized eggs (Liu et al., *Nat Cell Biol* 9:1436-1441, 2007). Although T-SCE events have been demonstrated in several studies, genes involved in this important process remain to be identified.

SUMMARY

The present disclosure provides methods for increasing genome stability of an embryonic stem (ES) cell or induced pluripotent stem (iPS) cell, or increasing telomere length in an ES or iPS cell, or both. For example, such methods can enhance the presence of a normal karyotype, reduce chromosome fusions and fragmentations, reduce genomic sister chromosome exchange, increase telomere recombination, or combinations thereof, in a cell. In particular examples, methods include contacting an ES or iPS cell with an agent (for example introducing the agent into an ES or iPS cells) that increases expression of Zscan4 in the ES or iPS cell relative to expression of Zscan4 in a cell in the absence of the agent. Exemplary agents that increase Zscan4 expression include but are not limited to Zscan4-encoding nucleic acid molecules, retinoic acids and agents that induce oxidative stress.

Methods for increasing the genome stability in a population of ES or iPS cells, increasing telomere length in a population of ES or iPS cells, or both, are provided. In particular examples, methods include selecting Zscan4$^+$ ES or iPS cells from the population of ES or iPS cells (which may include both Zscan4$^+$ and Zscan4$^-$ ES or iPS cells). For example, a population of ES or iPS cells can be transfected with an expression vector that includes a Zscan4 promoter operably linked to a reporter gene, wherein expression of the reporter gene indicates Zscan4 is expressed in the subpopulation of ES or iPS cells. Cells expressing the reporter gene can be detected (e.g., by detecting a signal produced by the protein encoded by the reporter gene) and then isolated. For example, if the reporter gene is green fluorescent protein (GFP) or a related fluorescent protein (such as Emerald), Zscan4-positive cells can be recognized based on the fluorescence and can be sorted by a fluorescence-activated cell sorter (FACS). If the reporter gene is a cell surface marker, Zscan4-positive cells can be sorted by FACS or by magnetic beads that can bind to the cell surface marker.

ES or iPS cells expressing Zscan4 can be used therapeutically. For example, a subject in need of ES cell therapy can be selected and administered a therapeutically effective amount of a subpopulation of undifferentiated ES or iPS cells that are Zscan4+. For example, cells fully differentiated from Zscan4+ ES or iPS cells can also be used for therapeutic administration. Examples of subjects that can benefit from such therapy include a subject having cancer, an autoimmune disease, a neurologic injury or a neurodegenerative disorder, as well as other disorders that can benefit from regenerative therapies.

Also provided herein is a method of treating a subject with cancer by administering to the subject an agent that increases expression of Zscan4.

Further provided is a method of inducing differentiation of isolated ES cells or isolated iPS cells into germ cells. In some embodiments, the method includes contacting the ES or iPS cells with an agent that increases expression of Zscan4 in the ES or iPS cells, thereby inducing differentiation of the ES or iPS cells into germ cells.

A method of inducing meiosis, meiosis-specific recombination and/or DNA repair in an isolated ES cell or an isolated iPS cell is also provided. In some embodiments, the method includes contacting the ES or iPS cell with an agent that increases expression of Zscan4 in the ES or iPS cell, thereby inducing meiosis, meiosis-specific recombination and/or DNA repair in the ES or iPS cell.

A method of protecting a cell from a DNA-damaging agent by contacting the cell with an agent that increases expression of Zscan4 is also provided.

The foregoing and other objects and features of the disclosure will become more apparent from the following detailed description, which proceeds with reference to the accompanying figures.

BRIEF DESCRIPTION OF THE FIGURES

FIG. 1J is a table of the top 20 differentially expressed genes in Em+ cells.

FIG. 3B is a set of digital images of RNA-FISH for Zscan4 and immunostaining for Cre-recombinase, which shows co-staining of Zscan4 RNA and Cre-recombinase in a small population of cells after short exposure of pZscan4-CreERT2 ES cells to tamoxifen. FIG. 3C is a set of digital images showing co-immunostaining analysis of Pou5f1 and LacZ after long-term exposure of pZscan4-CreERT2 ES cells to tamoxifen. All nuclei were labeled with DAPI.

FIG. 4G is a table showing karyotype analysis of Zscan4 knockdown and rescue cells compared to shRNA controls. Results from passage 3 (left panel) show multiple karyotype abnormalities, such as fusions and fragmentations, which are partially prevented by Zscan4 rescue. Results from passage 10 after cell crisis (right panel) show further deterioration of karyotype (only 30% normal), which are partially prevented by Zscan4 rescue.

FIG. 6C is a set of images showing co-localization of ZSCAN4C-FLAG in sister chromatids in metaphase spreads. Chromosomes are stained by DAPI. Arrows mark chromosomes with intense staining at the telomere regions. FIG. 6D is a set of images showing increased incidence of T-SCE in Zscan4-overexpressing cells. Representative images of telomere recombination are visualized by chromosome orientation FISH(CO-FISH) assay. Chromosomes are stained by DAPI. A Cy3-conjugated telomere probe marks telomeres. Left panel: tet-Zscan4c cells (Dox+) with no telomere recombination in most nuclei. Middle and Right panels: test-Zscan4c cells (Dox−) with increased telomere recombination events (arrowheads). Images are representative of three independent experiments. FIG. 6E is a table showing a more than 10-fold increase in T-SCE frequency by Zscan4 over-expression in tet-Zscan4c cells. The table shows the total T-SCE events observed in >20 nuclei per sample. As negative controls, tet-Zscan4c cells in the Dox+ condition and tet-Empty cells for a possible doxycycline effect on T-SCE, were used.

FIGS. 12A and 12B are graphs showing survival of control ES cells (A) and tet-Zscan4 ES cells (B) after treatment with mitomycin C (MMC). Control ES cells contained a control plasmid (tet-Empty). Cells were cultured in standard ES medium (LIF+) and passaged into two groups: (1) in the absence of doxycycline (Dox) or (2) in the presence of Dox at a final concentration of 0.2 μg/ml. The Dox+ and Dox− media were changed every day. On the fourth day, the cells were cultured for 6 hours in the presence of MMC at a final concentration ranging from 0 to 600 ng/ml. MMC was removed from the culture by changing the media and cells were then incubated for 3 more days in the Dox+ medium, with the medium changed every day. Cells were harvested and the number of live cells was counted.

SEQUENCE LISTING

Figure 1B:
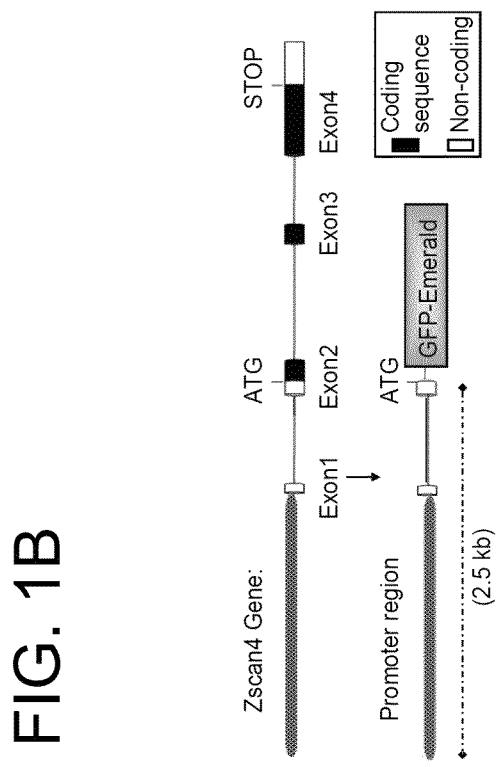
FIG. 1B is a schematic diagram of the Zscan4-promoter Emerald-reporter vector.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file, created on Apr. 11, 2014, 88.4 KB, which is incorporated by reference herein.

In the accompanying sequence listing:

SEQ ID NOs: 1 and 2 are the nucleotide sequences of the forward and reverse primers, respectively, used for amplification of the Zscan4 promoter.

SEQ ID NOs: 3-20 are the nucleotide sequences of qPCR primers.

SEQ ID NOs: 21 and 22 are primer sequences used to amplify Zscan4 shRNAs.

SEQ ID NO: 23 is the sequence of a nucleotide repeat used for CO-FISH analysis.

SEQ ID NOs: 24 and 25 are nucleotide and amino acid sequences of Zscan4a.

SEQ ID NOs: 26 and 27 are nucleotide and amino acid sequences of Zscan4b.

SEQ ID NOs: 28 and 29 are nucleotide and amino acid sequences of Zscan4c.

SEQ ID NOs: 30 and 31 are nucleotide and amino acid sequences of Zscan4d.

SEQ ID NOs: 32 and 33 are nucleotide and amino acid sequences of Zscan4e.

SEQ ID NOs: 34 and 35 are nucleotide and amino acid sequences of Zscan4f.

SEQ ID NOs: 36 and 37 are nucleotide and amino acid sequences of human ZSCAN4, deposited under Genbank Accession No. NM_152677 as of Sep. 4, 2009.

SEQ ID NO: 38 is the nucleotide sequence of the Zscan4-Emerald expression vector (9396 bp). The starting nucleotide of the Zscan4c promoter sequence is 906 and the ending nucleotide is 4468.

SEQ ID NO: 39 is an N-terminal epitope of Zscan4 used to generate antibodies.

DETAILED DESCRIPTION

I. Introduction

The Zscan4 gene was previously identified using expression profiling of all preimplantation stages of mouse embryos using a large-scale cDNA sequencing project (Ko et al., *Development* 127:1737-1749, 2000; Sharov et al., *PLoS Biol* 1:E74, 2003; WO 2008/118957) and DNA microarray analysis (Hamatani et al., *Dev Cell* 6:117-131, 2004). Zscan4 consists of 6 paralog genes (Zscan4a to Zscan4f) and 3 pseudogenes (Zscan4-ps1 to Zscan4-ps3) clustered on an approximately 850 kb region of chromosome 7. Among the six paralogs, the open reading frames of Zscan4c, Zscan4d, and Zscan4f encode a SCAN domain as well as all four zinc finger domains, suggesting their potential role as transcription factors. A high expression peak of Zscan4 marks the late 2-cell stage of mouse embryos. Zscan4 expression, normally below detection threshold in blastocysts, is reactivated in vitro in a small fraction of ES cells in culture. Although all six Zscan4 paralogs are expressed in ES cells, Zscan4c is the predominant paralog, whereas Zscan4d is the predominant paralog in 2-cell embryos (Falco et al., *Dev Biol* 307:539-550, 2007).

Disclosed herein is the finding that Zscan4 is associated with a unique transient state in undifferentiated ES cells, in which other 2-cell embryo-specific genes are activated. Furthermore, Zscan4 was determined to be essential for long-term maintenance of genomic integrity and to mediate a regulated telomere recombination in normal undifferentiated ES cells, therefore making it indispensable for proper long-term self-renewal in ES cells. Also disclosed herein is the finding that Zscan4 is involved in the induction and recruitment of the meiosis-specific homologous recombination machinery to telomeres. The inventors have further determined that Zscan4 expression can be induced by retinoids or oxidative stress and expression of Zscan4 protects cells against DNA-damaging agents.

II. Abbreviations

ALT alternative lengthening of telomeres
atRA all-trans retinoid acid
bp base pair
BrdU bromodeoxyuridine
BSA bovine serum albumin
cDNA complementary DNA
CO-FISH chromatid orientation FISH
DNA deoxyribonucleic acid
Dox doxycycline
DSB double strand DNA break
EB embryoid bodies
EC embryonal carcinoma
EG embryonic germ
Em(+) emerald-positive
Em(−) emerald-negative
ES embryonic stem
ES* zscan4$^+$ ES cells
FACS fluorescence activated cell sorting
FBS fetal bovine serum
FISH fluorescence in situ hybridization
GS germline stem
GFP green fluorescent protein
hCG human chorionic gonadotropin
ICM inner cell mass
iPS cells induced pluripotent stem cells
IRES internal ribosomal entry site
IU international unit
LIF leukemia inhibitory factor
maGSC multipotent adult germline stem cell
MAPC multipotent adult progenitor cell
ORF open reading frame
PCR polymerase chain reaction
PFA paraformaldehyde
PMSG pregnant mare's serum gonadotropin Q-FISH quantitative FISH
qPCR quantitative polymerase chain reaction
qRT-PCR quantitative reverse-transcriptase polymerase chain reaction
RA retinoic acid
RNA ribonucleic acid
SEM standard error of the mean
shRNA short hairpin RNA
SSC saline-sodium citrate
SCE sister chromatid exchange
Tet tetracycline
TFU telomere fluorescence unit
TRAP telomeric repeat amplification protocol
TS trophoblast stem
T-SCE telomere sister chromatid exchange
USSC unrestricted somatic stem cell
UTR untranslated region
UV ultraviolet WISH whole-mount in situ hybridization II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of specific terms are provided:

Administration: To provide or give a subject an agent, such as an ES cell or population of ES cells that express Zscan4, by any effective route. An exemplary route of administration includes, but is not limited to, injection (such as subcutaneous, intramuscular, intradermal, intraperitoneal, intravenous or intra-arterial).

Adult stem cell: Undifferentiated cells, found throughout the body after embryonic development, that multiply by cell division to replenish dying cells and regenerate damaged tissues. Also known as somatic stem cells.

Agent: Any protein, nucleic acid molecule, compound, small molecule, organic compound, inorganic compound, or other molecule of interest. In some embodiments, the "agent" is any agent that increases expression of Zscan4. In particular example, the agent is a nucleic acid molecule encoding Zscan4, a retinoid or an agent that induces oxidative stress.

Autoimmune disease: A disease resulting from an aberrant immune response, such as the production of antibodies or cytotoxic T cells specific for a self antigen or a subject's own cells or tissues.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Contacting: Placement in direct physical association; includes both in solid and liquid form. As used herein, "contacting" is used interchangeably with "exposed."

Degenerate variant: A polynucleotide encoding a polypeptide, such as a Zscan4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Differentiation: Refers to the process by which a cell develops into a specific type of cell (for example, muscle cell, skin cell etc.). In the context of the present disclosure, differentiation of embryonic stem cells refers to the development of the cells toward a specific cell lineage. As a cell becomes more differentiated, the cell loses potency, or the ability to become multiple different cell types. As used herein, inhibiting differentiation means preventing or slowing the development of a cell into a specific lineage.

DNA repair: Refers to a collection of processes by which a cell identifies and corrects damage to the DNA molecules that encode its genome.

Embryonal carcinoma (EC) cells: Pluripotent stem cells derived from teratocarcinomas, which are considered the malignant counterparts of embryonic stem (ES) cells.

Embryonic stem (ES) cells: Pluripotent cells isolated from the inner cell mass of the developing blastocyst. ES cells can be derived from any organism, such as a mammal. In one embodiment, ES cells are produced from mice, rats, rabbits, guinea pigs, goats, pigs, cows, monkeys and humans. Human and murine derived ES cells are exemplary. ES cells are pluripotent cells, meaning that they can generate all of the cells present in the body (bone, muscle, brain cells, etc.). Methods for producing murine ES cells can be found, for example, in U.S. Pat. No. 5,670,372. Methods for producing human ES cells can be found, for example, in U.S. Pat. No. 6,090,622, PCT Publication No. WO 00/70021 and PCT Publication No. WO 00/27995. A number of human ES cell lines are known in the art and are publically available. For example, the National Institutes of Health (NIH) Human Embryonic Stem Cell Registry provides a list of a number of human ES cell lines that have been developed (a list can be found online at the NIH Office of Extramural Research web site at http://grants.nih.gov/stem_cells/registry/current.htm).

Encapsulated: As used herein, a molecule "encapsulated" in a nanoparticle refers to a molecule (such as Zscan4 protein) that is either contained within the nanoparticle or attached to the surface of the nanoparticle, or a combination thereof.

ES cell therapy: A treatment that includes administration of ES cells to a subject. In particular examples, the ES cells are Zscan4$^+$, wherein the Zscan4 is endogenous or exogenous to the ES cells.

Fluorescent protein: A genetically-encoded protein that exhibits fluorescence when exposed to a particular wavelength of light. A broad range of fluorescent protein genetic variants have been developed that feature fluorescence emission spectral profiles spanning almost the entire visible light spectrum. Examples include anthozoan fluorescent proteins, green fluorescent protein (GFP) (which exhibits green fluorescence when exposed to blue light), as well as mutants thereof such as EGFP, blue fluorescent protein (EBFP, EBFP2, Azurite, mKalama1, which except for mKalama1 contain a Y66H substitution.), cyan fluorescent protein (ECFP, Cerulean, CyPet, which include a Y66W substitution), and yellow fluorescent protein derivatives (YFP, Citrine, Venus, YPet, which include a T203Y substitution). Other particular examples include Emerald Green Fluorescent Protein (EmGFP) and Strawberry. For overview, see for example Shaner et al., *Nat. Methods* 2(12):905-909, 2005.

Genome stability: The ability of a cell to faithfully replicate DNA and maintain integrity of the DNA replication machinery. An ES cell with a stable genome generally defies cellular senescence, can proliferate more than 250 doublings without undergoing crisis or transformation, has a low mutation frequency and a low frequency of chromosomal abnormalities (e.g., relative to embryonal carcinoma cells), and maintains genomic integrity. Long telomeres are thought to provide a buffer against cellular senescence and be generally indicative of genome stability and overall cell health. Chromosome stability (e.g., few mutations, no chromosomal rearrangements or change in number) is also associated with genome stability. A loss of genome stability is associated with cancer, neurological disorders and premature aging. Signs of genome instability include elevated mutation rates, gross chromosomal rearrangements, alterations in chromosome number, and shortening of telomeres.

Germ cell: The cells that give rise to the gametes (i.e., eggs and sperm) of organisms that reproduce sexually.

Heterologous: A heterologous polypeptide or polynucleotide refers to a polypeptide or polynucleotide derived from a different source or species. For example, a mouse Zscan4 peptide expressed in a human ES cell is heterologous to that ES cell.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Induced pluripotent stem (iPS) cells: A type of pluripotent stem cell artificially derived from a non-pluripotent cell, typically an adult somatic cell, by inducing a "forced" expression of certain genes. iPS cells can be derived from any organism, such as a mammal. In one embodiment, iPS cells are produced from mice, rats, rabbits, guinea pigs, goats, pigs, cows, monkeys and humans. Human and murine derived iPS cells are exemplary. In particular examples, iPS cells are used in place of (or in addition to) the ES cells described herein. For example iPS cells that are Zscan4$^+$ can be used in place of (or in addition to) the Zscan4$^+$ ES cells.

iPS cells are similar to ES cells in many respects, such as the expression of certain stem cell genes and proteins, chromatin methylation patterns, doubling time, embryoid body formation, teratoma formation, viable chimera formation, and potency and differentiability. Methods for producing iPS cells are known in the art. For example, iPS cells are typically derived by transfection of certain stem cell-associated genes (such as Oct-3/4 (Pouf51) and Sox2) into non-pluripotent cells, such as adult fibroblasts. Transfection can be achieved through viral vectors, such as retroviruses, lentiviruses, or adenoviruses. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. In one example, iPS from adult human cells are generated by the method of Yu et al. (*Science* 318(5854):1224, 2007) or Takahashi et al. (Cell 131(5):861-72, 2007).

Isolated: An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, "isolated" proteins have been substantially separated or purified from other proteins of the cells of an organism in which the protein naturally occurs, and encompasses proteins prepared by recombination expression in a host cell as well as chemically synthesized proteins. Similarly, "isolated" cells, such as those expressing Zscan4, have been substantially separated away from other cell types (such as cells that don't express Zscan4).

Meiosis: The process of reductional division in which the number of chromosomes per cell is cut in half. In animals, meiosis always results in the formation of gametes, while in other organisms it can give rise to spores. As with mitosis, before meiosis begins, the DNA in the original cell is replicated during S-phase of the cell cycle. Two cell divisions separate the replicated chromosomes into four haploid gametes or spores. Meiosis is essential for sexual reproduction and therefore occurs in all eukaryotes (including single-celled organisms) that reproduce sexually. During meiosis, the genome of a diploid germ cell, which is composed of long segments of DNA packaged into chromosomes, undergoes DNA replication followed by two rounds of division, resulting in four haploid cells. Each of these cells contains one complete set of chromosomes, or half of the genetic content of the original cell.

Multipotent cell: Refers to a cell that can form multiple cell lineages, but not all cell lineages.

Nanoparticle: A particle less than about 1000 nanometers (nm) in diameter. Exemplary nanoparticles for use with the methods provided herein are made of biocompatible and biodegradable polymeric materials. In some embodiments, the nanoparticles are PLGA nanoparticles. As used herein, a "polymeric nanoparticle" is a nanoparticle made up of repeating subunits of a particular substance or substances. "Poly (lactic acid) nanoparticles" are nanoparticles having repeated lactic acid subunits. Similarly, "poly(glycolic acid) nanoparticles" are nanoparticles having repeated glycolic acid subunits.

Neurologic injury: A trauma to the nervous system (such as to the brain or spinal cord or particular neurons), which adversely affects the movement and/or memory of the injured patient. For example, such patients may suffer from dysarthria (a motor speech disorder), hemiparesis or hemiplegia.

Neurodegenerative disorder: A condition in which cells of the brain and spinal cord are lost. Neurodegenerative diseases result from deterioration of neurons or their myelin sheath which over time lead to dysfunction and disabilities. Conditions that result can cause problems with movement (such as ataxia) and with memory (such as dementia).

Non-human animal: Includes all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one example, the non-human animal is a transgenic animal, such as a transgenic mouse, cow, sheep, or goat. In one specific, non-limiting example, the transgenic non-human animal is a mouse.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked nucleic acid sequences are contiguous and where necessary to join two protein coding regions, in the same reading frame.

Oxidative stress: An imbalance between the production of reactive oxygen species and a biological system's ability to readily detoxify the reactive intermediates or to repair the resulting damage. Disturbances in the normal redox state of tissues can cause toxic effects through the production of peroxides and free radicals that damage all components of the cell, including proteins, lipids, and DNA. In some embodiments of the disclosed methods, the agent that induces oxidative stress is hydrogen peroxide ($H_2O_2$).

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the Zscan4 proteins, Zscan4 nucleic acid molecules, or cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pharmaceutical agent: A chemical compound, small molecule, or other composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pluripotent cell: Refers to a cell that can form all of an organism's cell lineages (endoderm, mesoderm and ectoderm), including germ cells, but cannot form an entire organisms autonomously.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide, such as a Zscan4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An "epitope" is a region of a polypeptide capable of binding an immunoglobulin generated in response to contact with an antigen. Thus, smaller peptides containing the biological activity of Zscan4, or conservative variants of Zscan4, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a Zscan4 polypeptide, or other polypeptides disclosed herein, includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may be, for example, at least 80%, 90% or even 95% or 98% identical to the native amino acid sequence (such as a native Zscan4 sequence).

Promoter: Nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Reporter gene: A gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell. Exemplary reporter genes include fluorescent and luminescent proteins (such as green fluorescent protein (GFP) and the red fluorescent protein from the gene dsRed), the enzyme luciferase (which catalyzes a reaction with luciferin to produce light), the lacZ gene (which encodes the protein β-galactosidase, which causes cells expressing the gene to appear blue when grown on a medium that contains the substrate analog X-gal), and the chloramphenicol acetyltransferase (CAT) gene (which confers resistance to the antibiotic chloramphenicol). In one embodiment, the reporter gene encodes the fluorescent protein Emerald. In another embodiment, the reporter gene encodes the fluorescent protein Strawberry. Additional examples are provided below.

Retinoids: A class of chemical compounds that are related chemically to vitamin A. Retinoids are used in medicine, primarily due to the way they regulate epithelial cell growth. Retinoids have many important and diverse functions throughout the body including roles in vision, regulation of cell proliferation and differentiation, growth of bone tissue, immune function, and activation of tumor suppressor genes. Examples of retinoids include, but are not limited to, all-trans retinoic acid (atRA), 9-cis retinoic acid (9-cis RA), 13-cis RA and vitamin A (retinol).

Senescence: The inability of a cell to divide further. A senescent cell is still viable, but does not divide.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs may use SEG. In addition, a manual alignment can be performed.

When aligning short peptides (fewer than around 30 amino acids), the alignment is be performed using the Blast 2 sequences function, employing the PAM30 matrix set to default parameters (open gap 9, extension gap 1 penalties). When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, ES cells, EG cells, GS cells, MAPCs, maGSCs, USSCs and adult stem cells. In one embodiment, stem cells can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation.

Subpopulation: An identifiable portion of a population. As used herein, a "subpopulation" of ES cells expressing Zscan4 is the portion of ES cells in a given population that has been identified as expressing Zscan4. In one embodiment, the subpopulation is identified using an expression vector comprising a Zscan4 promoter and a reporter gene, wherein detection of expression of the reporter gene in a cell indicates the cell expresses Zscan4 and is part of the subpopulation.

Telomere: Refers to the end of a eukaryotic chromosome, a specialized structure involved in the replication and stability of the chromosome. Telomeres consist of many repeats of a short DNA sequence in a specific orientation. Telomere functions include protecting the ends of the chromosome so that chromosomes do not end up joined together, and allowing replication of the extreme ends of the chromosomes (by telomerase). The number of repeats of telomeric DNA at the end of a chromosome decreases with age.

Therapeutic amount: An amount of a therapeutic agent sufficient to achieve the intended purpose. For example, a therapeutic amount of Zscan4$^+$ ES cells is an amount sufficient to reduce a disorder or symptoms of a disorder that can benefit from ES cell therapy. A therapeutic amount may in some example not treat the disorder or symptoms 100%. However, a decrease in any known feature or symptom of a disorder that can benefit from ES cell therapy (such as Zscan4$^+$ ES cells), such as a decrease of at least 10%, at least 15%, at least 25%, at least 30%, at least 50%, at least 60%, at least 70%, at least 75%, at least 85%, at least 95%, or greater, can be therapeutic. The therapeutic amount of a given therapeutic agent will vary with factors such as the nature of the agent, the route of administration, the size and species of the animal to receive the therapeutic agent, and the purpose of the administration. The therapeutic amount in each individual case can be determined empirically without undue experimentation by a skilled artisan according to established methods in the art.

Totipotent cell: Refers to a cell that can form an entire organism autonomously. Only a fertilized egg (oocyte) possesses this ability (stem cells do not).

Transfecting or transfection: Refers to the process of introducing nucleic acid into a cell or tissue. Transfection can be achieved by any one of a number of methods, such as, but not limited to, liposomal-mediated transfection, electroporation and injection.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors include, for example, virus vectors and plasmid vectors.

Zscan4: A group of genes identified as exhibiting 2-cell-specific expression and ES cell-specific expression. In the mouse, the term "Zscan4" refers to a collection of genes including three pseudogenes (Zscan1-ps1, Zscan4-ps2 and Zscan4-ps3) and six expressed genes (Zscan4a, Zscan4b, Zscan4c, Zscan4d, Zscan4e and Zscan4f). As used herein, Zscan4 also includes human ZSCAN4. Zscan4 refers to Zscan4 polypeptides and Zscan4 polynucleotides encoding the Zscan4 polypeptides.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, GenBank Accession numbers and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Exceptional genomic stability is one of the hallmarks of mouse embryonic stem (ES) cells. However, the genes contributing to this stability remain unidentified. It is shown herein that Zscan4 is involved in telomere maintenance and long-term-genomic stability in ES cells. In the standard ES cell culture condition that maintains the undifferentiated state of ES cells (e.g., including LIF), only about 5% of ES cells express Zscan4 at a given time, but nearly all ES cells experience the Zscan4$^+$ state within nine passages. The transient Zscan4-positive state is associated with rapid telomere extension by telomere recombination and upregulation of meiosis-specific homologous recombination genes, which encode proteins that are colocalized with ZSCAN4 on telomeres. Furthermore, Zscan4 knockdown gradually shortens telomeres, increases karyotype abnormalities and spontaneous sister chromatid exchange, and slows down cell proliferation until reaching crisis by eight passages.

A Zscan4 gene cluster includes 6 transcribed paralogous genes (Zscan4a-Zscan4f), which share high sequence similarities and are thus collectively called Zscan4. A sharp expression peak of Zscan4 marks the late 2-cell stage of mouse embryos and is essential for embryo implantation and blastocyst outgrowth in tissue culture. Zscan4d is transcribed predominantly in 2-cell embryos, whereas Zscan4c is transcribed predominantly in ES cells and is associated with self renewal. Both Zscan4c and Zscan4d encode a SCAN domain, predicted to mediate protein-protein interactions, and four DNA binding Zinc-finger domains. It is shown herein that Zscan4 is involved in long-term maintenance of karyotype integrity and mediation of regulated telomere recombination in normal undifferentiated ES cells.

Figure 7A:
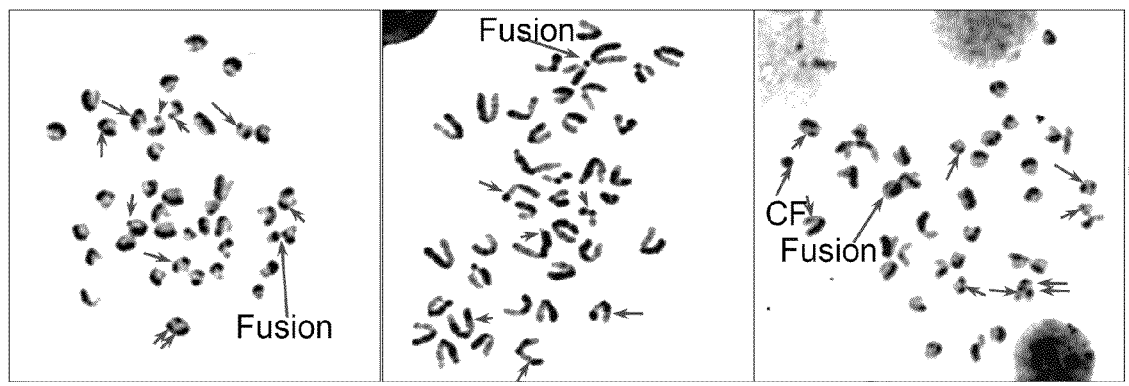
FIG. 7A is a set of images showing the increased rate of sister chromatid exchange (SCE) in Zscan4-knockdown cells. Representative images of SCE assay performed in Zscan4-knockdown cells are shown. Arrows mark SCE events.
Figure 7B:
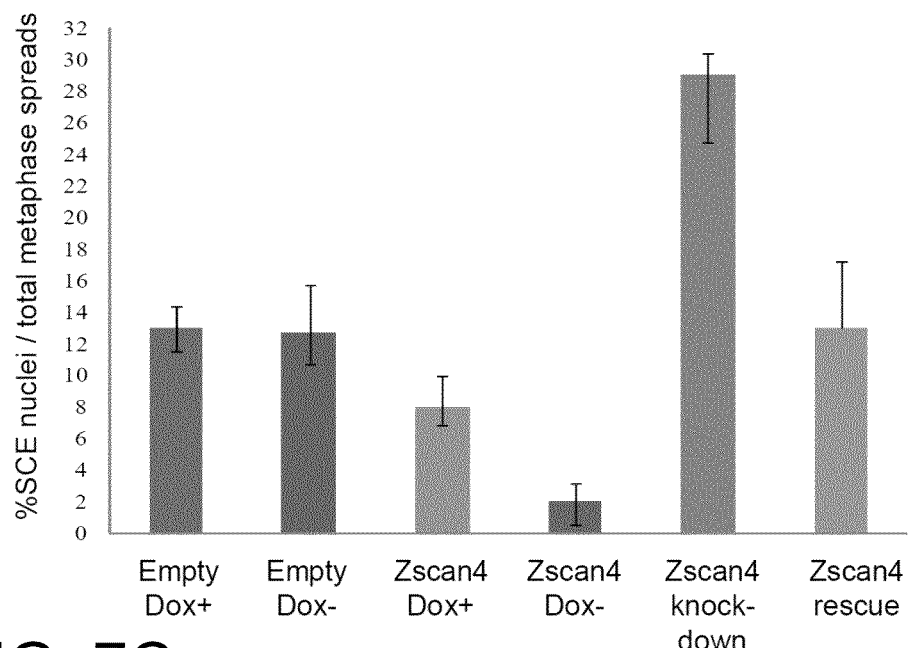
FIG. 7B is a graph showing SCE assay results, which demonstrate a 2.5-fold increase in the percentage of cells presenting SCE and genomic instability in Zscan4 knockdown cells. The SCE experiment was done in 3 independent experiments with the analysis of 50 metaphases for each experiment (n=50, total n=150). Error bars indicate S.E.M.
Figure 7C:
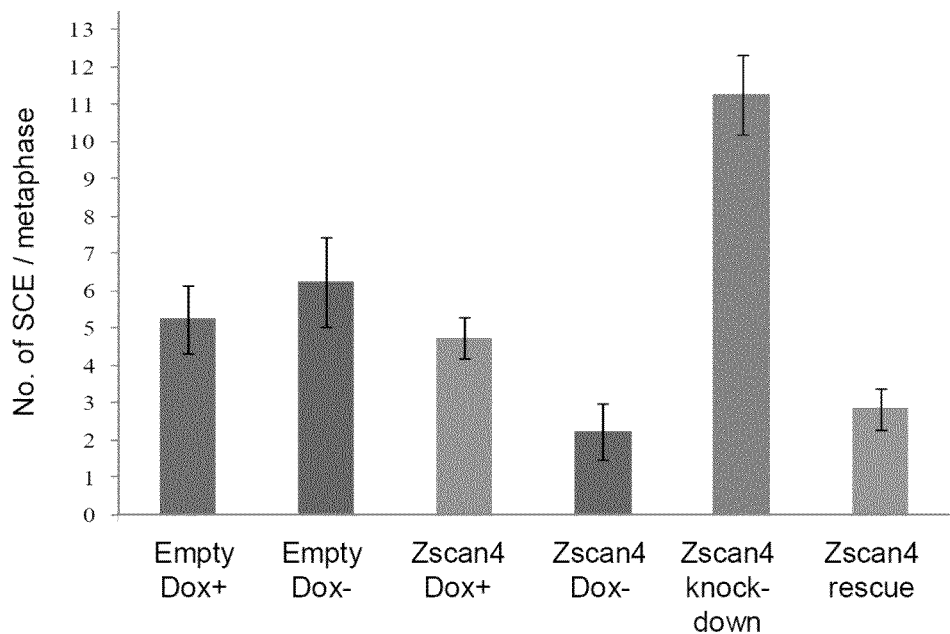
FIG. 7C is a graph showing that the number of SCE events per affected metaphases was also significantly elevated. Error bars indicate S.E.M.
Figure 7D:
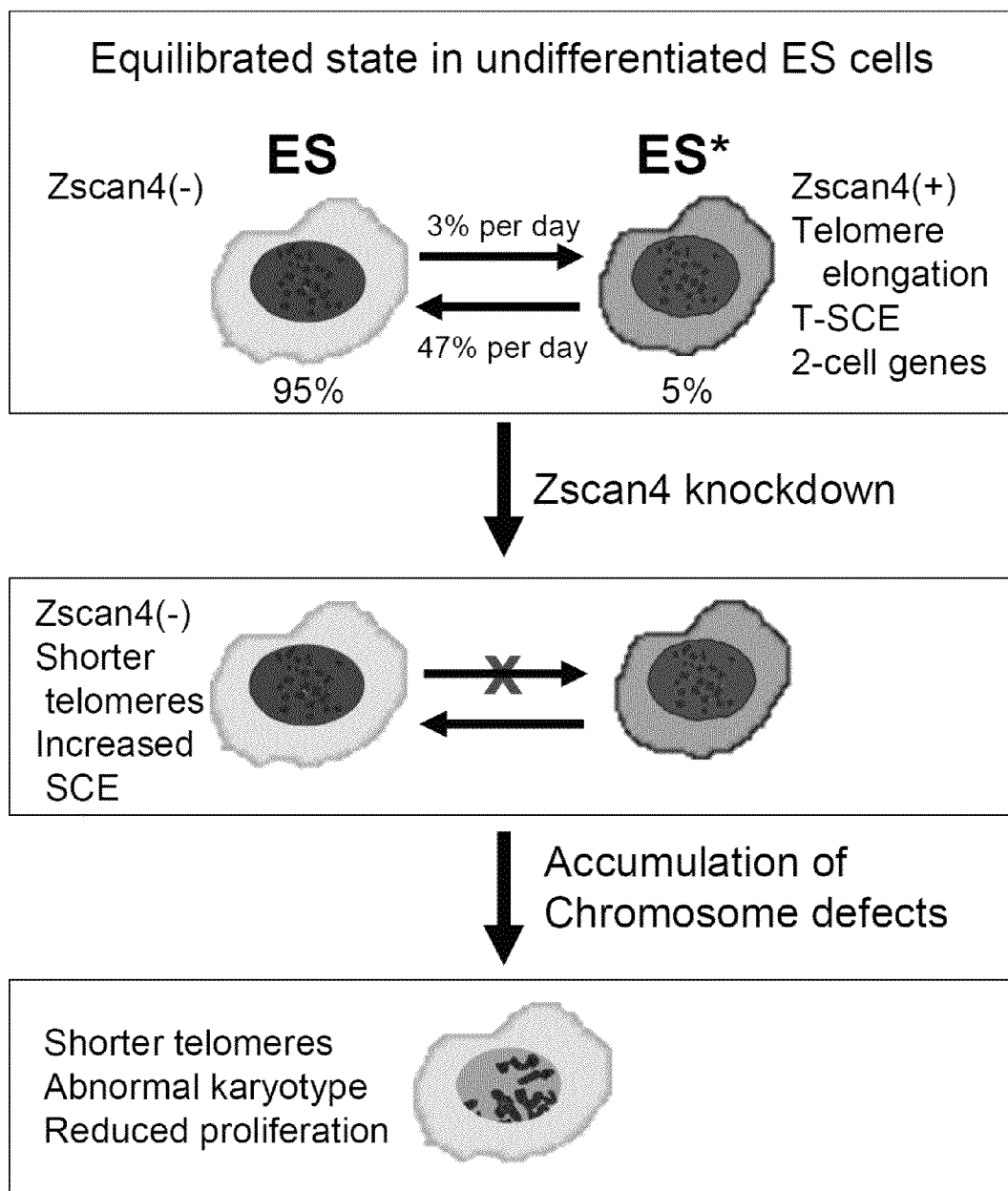
FIG. 7D is a schematic diagram showing the feature of ES* state and the effect of Zscan4 knockdown on ES cells.

It is also shown herein that Zscan4 has a unique function as an activator of spontaneous telomere sister chromatic exchange (T-SCE) in undifferentiated ES cells and is involved in the regulation of telomere length and karyotype stability (FIG. 7D). As Zscan4 knockdown eventually leads to karyotype deterioration and the reduction of cell proliferation, these results indicate that Zscan4 is important for long-term self-renewal of ES cells. Furthermore, the data indicate that karyotype deterioration is due to telomere degradation as well as an increase in spontaneous non-telomeric SCE. Thus, this disclosure provides a first link to a novel mechanism employed by ES cells to sustain long-term genomic stability and telomere maintenance.

Regulation of telomeres by Zscan4 in mouse ES cells is distinctive from those previously reported. First, it is shown herein that Zscan4 is expressed transiently in ES cells, and thus, at any given time only ~5% of the undifferentiated ES cells are Zscan4 positive, whereas other heterogeneously expressed genes in ES cells (Tanaka, *Reprod. Fertil. Dev.* 21: 67-75, 2009; Carter et al., *Gene Expr. Patterns* 8:181-198, 2008) often mark specific cell lineages (Toyooka et al., *Development* 135:909-18, 2008; Hayashi et al., *Cell Stem Cell* 3:391-401, 2008). Constitutive Zscan4 expression may lead to abnormally long telomeres, which may explain why this gene is not ubiquitously expressed. Indeed, the results herein show that ZSCAN4 protein is able to form foci on telomeres along with meiosis-specific homologous recombination mediators indicating ES cells are able to utilize a novel mechanism for T-SCE. Second, telomere elongation by T-SCE has previously been observed in cells with little or no telomerase activity, for example, in long-term cultures of telomerase knockout Terc−/− ES cells (Wang et al., *Proc. Natl. Acad. Sci. USA* 102:10256-60, 2005; Niida, et al., *Mol. Cell. Biol.* 20:4115-27, 2000; Bailey et al., *Nucleic Acids Res* 32:3743-51, 2004). Similarly, T-SCE usually occurs in tumor cells that show no reactivation of telomerase. By contrast, it is shown herein that telomerase is active in normal undifferentiated ES cells expressing Zscan4. Third, most genes previously identified for telomere regulation are inhibitors of T-SCE, as downregulation of these genes increases T-SCE and/or telomere length (De Boeck et al., *J. Pathol.* 217:327-44, 2009), such as DNA methyltransferase DNMT1 and DNMT3 (Gonzalo et al., *Nat. Cell Biol.* 8:416-424, 2006) and Werner syndrome protein (WRN) (Laud et al., *Genes Dev.* 19:2560-70, 2005). An exception is the Rtel gene, as Rtel−/− ES cells show telomere shortening after induction of differentiation (Ding et al., *Cell* 117:873-86, 2004), but unlike Rtel, Zscan4 exhibits this phenotype in undifferentiated ES cells. Fourth, telomere elongation through T-SCE usually results from general chromosomal instability, along with increased SCE in non-telomeric sequences (Wang et al., *Proc. Natl. Acad. Sci. USA* 102:10256-60, 2005). By contrast, T-SCE mediated by Zscan4 is not associated with an increase of general SCE, and normal karyotype remains stable with lower spontaneous SCE rate.

The expression level of Zscan4 is varied among different pluripotent stem cells, which may be correlated to their difference in genomic stability. For example, consistent with the inferior ability of embryonal carcinoma (EC) cells to maintain genomic integrity (Blelloch et al., *Proc. Natl. Acad. Sci. USA* 101:13985-90, 2004), the expression of Zscan4 is much lower in EC cells than in ES cells (Aiba et al., *DNA Res.* 16:73-80, 2009). The expression level of Zscan4 in iPS cells (Takahashi & Yamanaka, *Cell* 126:663-76, 2006) is comparable to ES cells (Aiba et al., *DNA Res.* 16:73-80, 2009), indicating that iPS may have regained the ability of ES-like genome maintenance. By selecting cells able to activate Zscan4, cultures enriched for cells more suitable for future therapeutic purposes can be generated. Moreover, inducing and controlling Zscan4 expression provides a means to increase the genomic stability in other cell types, such as stem cells or cancer cells.

Based on these results, provided herein are methods of increasing genome stability of an isolated ES cell or iPS cell, increasing telomere length in an ES or iPS cell, or both. In particular examples, such methods include contacting the ES or iPS cell with an agent that increases expression of Zscan4 in the ES or iPS cell relative to expression of Zscan4 in an ES or iPS cell in the absence of the agent. For example, the ES or iPS cell can be incubated with the agent under conditions that permit the agent to enter the ES or iPS cell an increase Zscan4 expression.

Further provided is a method of inducing differentiation of isolated ES cells or isolated iPS cells into germ cells. In some embodiments, the method includes contacting the ES or iPS cells with an agent that increases expression of Zscan4 in the ES or iPS cells, thereby inducing differentiation of the ES or iPS cells into germ cells. In some embodiments, the agent is a nucleic acid molecule encoding Zscan4, or a Zscan4 protein or functional fragment thereof. In other embodiments, the agent is a retinoid, such as, but not limited to, atRA, 9-cis RA, 13-cis RA and vitamin A. In other embodiments, the agent induces oxidative stress.

A method of inducing meiosis, meiosis-specific recombination and/or DNA repair in an isolated ES cell or an isolated iPS cell is also provided. In some embodiments, the method includes contacting the ES or iPS cell with an agent that increases expression of Zscan4 in the ES or iPS cell, thereby inducing meiosis, meiosis-specific recombination and/or DNA repair in the ES or iPS cell. In some embodiments, the agent is a nucleic acid molecule encoding Zscan4, or a Zscan4 protein or functional fragment thereof. In other embodiments, the agent is a retinoid, such as, but not limited to, atRA, 9-cis RA, 13-cis RA and vitamin A. In other embodiments, the agent induces oxidative stress.

A method of protecting a cell from a DNA-damaging agent, comprising contacting the cell with an agent that increases expression of Zscan4 and exposing the cell to a DNA-damaging agent, wherein an increase in survival of the cell relative to a control indicates the agent protects the cell from the DNA-damaging agent. In some embodiments, the control is a cell exposed to the DNA-damaging agent that has not been induced to express Zscan4. In some embodiments, the cell is contacted with the agent prior to being exposed to the DNA-damaging agent. In other embodiments, the cell is contacted with the agent while simultaneously exposed to the DNA-damaging agent. In yet other embodiments, the cell is contacted with the agent after being exposed to the DNA-damaging agent. In some embodiments, the agent is a nucleic acid molecule encoding Zscan4, or a Zscan4 protein or functional fragment thereof. In some embodiments, the agent is a retinoid, such as, but not limited to, atRA, 9-cis RA, 13-cis RA and vitamin A. In some embodiments, the agent induces oxidative stress. In some embodiments, the DNA-damaging agent is a chemotherapeutic drug. In particular examples, the DNA-damaging agent is mitomycin C or cisplatin.

It is noted that although ES cells are described throughout the application, one skilled in the art will appreciate that iPS cells can be used instead of the ES cells in the disclosed compositions and methods. Thus, for example, methods of increasing genome stability of an iPS cell, increasing telomere length in an iPS cell, or both, are provided, as are methods of using such cells to treat patients in need of ES cell therapy. iPS cells are very similar to ES cells, but can be made from human fibroblast and other differentiated cells without going through the nuclear transplantation (cloning) procedure. Zscan4 is expressed at the same level in iPS cells as in the ES cells, and the inventors have shown that Zscan4 is also expressed only a small fraction (5%) of iPS cells in culture. Thus, human or other mammalian iPS cells can be used in place of (or in addition to) ES cells in the methods provided herein, such as iPS cells expressing Zscan4 (Zscan4$^+$ iPS cells).

Moreover, it is further noted that the disclosed compositions and methods can be useful for the treatment of cancer (described in further detail below). Thus, although ES cells are described throughout the application, one skilled in the art will appreciate that cancer cells can be used instead of the ES cells in the disclosed compositions and methods. For example, methods of increasing genome stability of a cancer cell, increasing telomere length in a cancer cell, or both, are provided, as are methods of treating a subject with cancer by administering a Zscan4 polypeptide or polynucleotide, such as administration directly to cancer cells.

Exemplary agents that can increase Zscan4 expression in a cell include isolated nucleic acid molecules encoding Zscan4. Zscan4 protein and coding sequences are well-known in the art as discussed in detail below. Any of the molecules described in section IV below can be used in the methods provided herein. One skilled in the art will appreciate that any Zscan4 coding sequence can be used, such as a mouse Zscan4c- or human ZSCAN4-encoding nucleic acid sequence. For example, ES or iPS cells can be transfected with a Zscan4-encoding isolated nucleic acid molecule under conditions sufficient to allow for expression of Zscan4 in the ES or iPS cell. In some examples, the isolated nucleic acid molecules encoding Zscan4 are part of a vector, such as a viral or plasmid vector. In one example, the isolated nucleic acid molecule encoding Zscan4 can be operably linked to a promoter that drives expression of Zcsan4. Constitutive and inducible promoters can be used.

In some embodiments, the agent that induces Zscan4 expression is a retinoid. Exemplary retinoids include, but are not limited to atRA, 9-cis RA, 13-cis RA and vitamin A. In other embodiments, the agent that induces Zscan4 expression is an agent that induces oxidative stress, for example hydrogen peroxide.

Also provided are methods for increasing genome stability in a population of ES or iPS cells, increasing telomere length in a population of ES or iPS cells, or both. In particular examples, the method includes selecting Zscan4$^+$ ES or iPS cells from the population of ES or iPS cells. That is, a population of ES or iPS cells containing ES or iPS cells expressing Zscan4 and ES or iPS cells not expressing Zscan4 can be enriched for the Zscan4-expressing ES or iPS cells for example by eliminating the non-Zscan4-expressing cells or selecting for the Zscan4-expressing cells. In one example, Zscan4$^+$ cells are selected by transfecting the population of cells with an expression vector that includes at least a Zscan4 promoter and a reporter gene, wherein expression of the reporter gene indicates Zscan4 is expressed in the subpopulation of ES or iPS cells. The cells in which Zscan4 expression is detected can be selected, for example by FACS. In one example, the expression vector is the nucleic acid sequence set forth as SEQ ID NO: 38, or a sequence having at least 80%, at least 90%, at least 95%, or at least 98% sequence identity to SEQ ID NO: 38. In another example, the reporter gene is a drug (e.g., antibiotic)-selectable marker, wherein the non-Zscan4-expressing cells are killed by adding the appropriate drug (e.g., hygromycin, neomycin, etc).

Methods are also provided for treating a subject in need of ES cell therapy. In some examples, the method includes selecting a subject in need of treatment and administering to the selected subject a subpopulation of undifferentiated ES (or iPS) cells that are Zscan4$^+$. Examples of subjects that can benefit from ES cell therapy include but are not limited to subjects having cancer, an autoimmune disease, neurologic injury or a neurodegenerative disorder, as well as other disorders where cellular regeneration is desired (such as wound healing, muscle repair (including cardiac), cartilage replacement (e.g., to treat arthritis), tooth regeneration, blindness, deafness, bone marrow transplant, and Crohn's disease). In some examples, the method includes selecting Zscan4$^+$ ES or iPS cells from a population of ES or iPS cells, and the Zscan4$^+$ ES or iPS cells are administered to the subject. For example, Zscan4$^+$ ES or iPS cells can be selected by transfecting the population of ES or iPS cells with an expression vector that includes a Zscan4 promoter (such as a Zscan4c promoter) and a reporter gene, wherein expression of the reporter gene indicates Zscan4 is expressed in the subpopulation of ES or iPS cells.

Also provided herein is a method of treating a subject with cancer by administering to the subject a Zscan4 polypeptide or polynucleotide. In some embodiments, the method further includes selecting a patient in need of such therapy. In some embodiments, the method includes administering the Zscan4 polypeptide or polynucleotide directly to tumor cells to tumor tissue, such as by injection. In particular examples, the subject is administered a vector comprising a Zscan4 polynucleotide. In other embodiments, the Zscan4 polypeptide is encapsulated by a nanoparticle.

Further provided is a method of enhancing chemoresponsiveness of a tumor in a subject, comprising administering to the subject an agent that inhibits expression of Zscan4. In some examples, the agent is administered directly to the tumor cells. A method of increasing the efficacy of a chemotherapeutic agent in an isolated cell by contacting the cell with an agent that inhibits expression of Zscan 4 is also provided.

IV. Zscan4 Polynucleotide and Polypeptide Sequences

Zscan4 nucleic acid and amino acid sequences have been previously described in the art (see, for example, WO 2008/118957, the disclosure of which is herein incorporated by reference; Falco et al., *Dev. Biol.* 307(2):539-550, 2007; and Carter et al., *Gene Expr. Patterns.* 8(3):181-198, 2008). As used herein, the term "Zscan4" includes any one of a group of mouse genes exhibiting 2-cell embryonic stage- or ES cell-specific expression (including Zscan4a, Zscan4b, Zscan4c, Zscan4d, Zscan4e and Zscan4f), the human ortholog ZSCAN4, or any other species ortholog of ZSCAN4. In a specific example, Zscan4 is mouse Zscan4c or human ZSCAN4.

Exemplary Zscan4 amino acid sequences are set forth in the Sequence Listing as SEQ ID NO: 25 (Zscan4a), SEQ ID NO: 27 (Zscan4b), SEQ ID NO: 29 (Zscan4c), SEQ ID NO: 31 (Zscan4d), SEQ ID NO: 33 (Zscan4e), SEQ ID NO: 35 (Zscan4f) and SEQ ID NO: 37 (human ZSCAN4). One skilled in the art will appreciate that sequences having at least 80%, at least 90%, at least 95%, or at least 98% sequence identity to these sequences and retain Zscan4 activity (such as the ability to enhance genome stability and increase telomere length in a ES cell) can be used in the methods provided herein.

ZSCAN4 amino acid sequences from other species are publically available, including dog ZSCAN4 (GenBank Accession Nos. XP_541370.2 and XP_853650.1); cow ZSCAN4 (GenBank Accession No. XP_001789302.1); and horse ZSCAN4 (GenBank Accession No. XP_001493994.1). Each of the above-listed GenBank Accession numbers is herein incorporated by references as it appears in the GenBank database on Sep. 4, 2009.

Specific, non-limiting examples of Zscan4 polypeptides that can be expressed in ES cells using the methods provided herein include polypeptides including an amino acid sequence at least 80%, at least 85%, at least 90%, at least 95%, at least 96%, at least 97%, at least 98% or at least 99% homologous to the amino acid sequence set forth in SEQ ID NO: 25, 27, 29, 31, 33, 35 or 37. In a further embodiment, a Zscan4 polypeptide is a conservative variant of SEQ ID NO: 25, 27, 29, 31, 33, 35 or 37, such that it includes no more than fifty conservative amino acid substitutions, such as no more than two, no more than five, no more than ten, no more than twenty, or no more than fifty conservative amino acid substitutions in SEQ ID NO: 25, 27, 29, 31, 33, 35 or 37. In another embodiment, a Zscan4 polypeptide has an amino acid sequence comprising the amino acid sequence set forth in SEQ ID NO: 25, 27, 29, 31, 33, 35 or 37. In another embodiment, a Zscan4 polypeptide has an amino acid sequence consisting of the amino acid sequence set forth in SEQ ID NO: 25, 27, 29, 31, 33, 35 or 37.

Fragments and variants of a Zscan4 polypeptide can readily be prepared by one of skill in the art using molecular techniques. In one embodiment, a fragment of a Zscan4 polypeptide includes at least 50, at least 100, at least 150, at least 200, at least 250, at least 300, at least 350, at least 400, at least 450 or at least 500 consecutive amino acids of the Zscan4 polypeptide. In a further embodiment, a fragment of Zscan4 is a fragment that confers a function of Zscan4 when transferred into a cell of interest, such as, but not limited to, enhancing genome stability and/or increasing telomere length.

Minor modifications of the Zscan4 polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

One of skill in the art can readily produce fusion proteins including a Zscan4 polypeptide and a second polypeptide of interest. Optionally, a linker can be included between the Zscan4 polypeptide and the second polypeptide of interest. Fusion proteins include, but are not limited to, a polypeptide including a Zscan4 polypeptide and a marker protein. In one embodiment, the marker protein can be used to identify or purify a Zscan4 polypeptide. Exemplary fusion proteins include, but are not limited to, green fluorescent protein, six histidine residues, or myc and a Zscan4 polypeptide.

One skilled in the art will appreciate that such variants, fragments, and fusions of Zscan4 useful for the disclosed methods are those that retain Zscan4 activity (such as the ability to enhance genome stability and increase telomere length or both in an ES cell).

Nucleic acid molecules encoding a Zscan4 polypeptide are termed Zscan4 polynucleotides or nucleic acid molecules. These polynucleotides include DNA, cDNA and RNA sequences which encode a Zscan4. It is understood that all polynucleotides encoding a Zscan4 polypeptide are also included herein, as long as they encode a polypeptide with a recognized Zscan4 activity, such as the ability to modulate genome stability or telomere length. The polynucleotides include sequences that are degenerate as a result of the genetic code. There are 20 natural amino acids, most of which are specified by more than one codon. Therefore, all degenerate nucleotide sequences are included as long as the amino acid sequence of the Zscan4 polypeptide encoded by the nucleotide sequence is functionally unchanged. A Zscan4 polynucleotide encodes a Zscan4 polypeptide, as disclosed herein. Exemplary polynucleotide sequences encoding Zscan4 that can be expressed in ES or iPS cells using the methods provided herein are set forth in the Sequence Listing as SEQ ID NO: 24 (Zscan4a), SEQ ID NO: 26 (Zscan4b), SEQ ID NO: 28 (Zscan4c), SEQ ID NO: 30 (Zscan4d), SEQ ID NO: 32 (Zscan4e), SEQ ID NO: 34 (Zscan4f) and SEQ ID NO: 36 (human ZSCAN4).

ZSCAN4 nucleic acid sequences from other species are publically available, including dog ZSCAN4 (GenBank Accession Nos. XM_541370.2 and XM_848557.1); cow ZSCAN4 (GenBank Accession No. XM_001789250.1); and horse ZSCAN4 (GenBank Accession No. XM_001493944.1). Each of the above-listed GenBank Accession numbers is herein incorporated by references as it appears in the GenBank database on Aug. 11, 2009.

In some embodiments, the Zscan4 polynucleotide sequence expressed in an ES or iPS cell using the methods provided herein is at least 80%, at least 85%, at least 90%, at least 95%, at least 96%, at least 97%, at least 98% or at least 99% identical to SEQ ID NO: 24, 26, 28, 30, 32, 34 or 36. In some embodiments, the Zscan4 polynucleotide sequence comprises the nucleic acid sequence set forth in SEQ ID NO: 24, 26, 28, 30, 32, 34 or 36. In some embodiments, the Zscan4 polynucleotide sequence consists of the nucleic acid sequence set forth in SEQ ID NO: 24, 26, 28, 30, 32, 34 or 36. In particular examples, the Zscan4 polynucleotide sequence expressed in an ES or iPS cell is exogenous to the cell. For example, the Zscan4 polynucleotide sequence can be a recombinant or non-native sequence to the ES or iPS cell.

Fragments and variants of Zscan4 polynucleotides can readily be prepared by one of skill in the art using molecular techniques. In one embodiment, a fragment of a Zscan4 polynucleotide includes at least 250, at least 500, at least 750, at least 1000, at least 1500, or at least 2000 consecutive nucleic acids of the Zscan4 polynucleotide. In a further embodiment, a fragment of Zscan4 is a fragment that confers a function of Zscan4 when expressed in a cell of interest, such as, but not limited to, enhancing genome stability and/or increasing telomere length.

Minor modifications of the Zscan4 polynucleotide sequences may result in expression of peptides which have substantially equivalent activity as compared to the unmodified counterpart polynucleotides described herein. Such modifications may be deliberate, as by site-directed mutagenesis, or may be spontaneous. All of the polynucleotides produced by these modifications are included herein.

Zscan4 polynucleotides include recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

With the provision of several Zscan4 nucleic acid and protein sequences described above, the expression of any Zscan4 protein (e.g., a heterologous Zscan4 protein) in an ES or iPS cell using standard laboratory techniques is now enabled. In some examples, the Zscan4 nucleic acid sequence is under the control of a promoter. In some examples, a vector system is used to express Zscan4, such as plasmids, bacteriophages, cosmids, animal viruses and yeast artificial chromosomes (YACs). These vectors may then be introduced into ES or iPS cells, which are rendered recombinant by the introduction of the heterologous Zscan4 cDNA.

A Zscan4 coding sequence may be operably linked to a heterologous promoter, to direct transcription of the Zscan4 coding nucleic acid sequence. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In one example, the promoter is a constitutive promoter, such as the CAG-promoter (Niwa et al., *Gene* 108(2):193-9, 1991), or the phosphoglycerate kinase (PGK)-promoter. In another example, the promoter is an inducible promoter such as a tetracycline-inducible promoter (Masui et al., *Nucleic Acids Res.* 33:e43, 2005). Other exemplary promoters that can be used to drive Zscan4 expression include but are not limited to: lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, and the promoter of the yeast alpha-mating factors. In some examples, a native Zscan4 promoter is used.

A vector system can used to express Zscan4. Exemplary vectors that can be used to express Zscan4 in ES cells include but are not limited to plasmids and viral vectors. In one example, vectors containing the promoter and enhancer regions of the SV40 or long terminal repeat (LTR) of the Rous Sarcoma virus and polyadenylation and splicing signal from SV40 (Mulligan and Berg, 1981, *Proc. Natl. Acad. Sci. USA* 78:2072-6; Gorman et al., 1982, *Proc. Natl. Acad. Sci. USA* 78:6777-81) are used. In one example, the vector is a viral vector, such as an adenoviral vector, an adeno-associated virus (AAV), such as described in U.S. Pat. No. 4,797,368 (Carter et al.) and in McLaughlin et al. (*J. Virol.* 62:1963-73, 1988) and AAV type 4 (Chiorini et al. *J. Virol.* 71:6823-33, 1997) and AAV type 5 (Chiorini et al. *J. Virol.* 73:1309-19, 1999), or retroviral vector (such as the Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus). Other viral transfection systems may also be utilized, including Vaccinia virus (Moss et al., 1987, *Annu. Rev. Immunol.* 5:305-24), Bovine Papilloma virus (Rasmussen et al., 1987, *Methods Enzymol.* 139:642-54) or members of the herpes virus group such as Epstein-Barr virus (Margolskee et al., 1988, *Mol. Cell. Biol.* 8:2837-47). In addition, vectors may contain antibiotic selectable markers (such as neomycin, hygromycin or mycophoenolic acid) to permit selection of transfected cells that exhibit stable, long-term expression of the vectors (and therefore the Zscan4 nucleic acid).

The vectors can be maintained in the cells as episomal, freely replicating entities by using regulatory elements of viruses such as papilloma (Sarver et al., 1981, *Mol. Cell. Biol.* 1:486) or Epstein-Barr (Sugden et al., 1985, *Mol. Cell. Biol.* 5:410). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product.

The transfer of DNA into human or other mammalian cells is a conventional technique. For example, an isolated Zscan4 nucleic acid sequence (for example as a naked DNA or as part of an expression vector) can be introduced into the recipient cells for example by precipitation with calcium phosphate (Graham and vander Eb, 1973, *Virology* 52:466) or strontium phosphate (Brash et al., 1987, *Mol. Cell. Biol.* 7:2013), electroporation (Neumann et al., 1982, *EMBO J.* 1:841), lipofection (Felgner et al., 1987, *Proc. Natl. Acad. Sci. USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the Zscan4 nucleic acid sequence can be part of a viral vector, which is introduced into the ES cells by infection. Systems are developed that use, for example, retroviruses (Bernstein et al., 1985, *Gen. Engrg.* 7:235), adenoviruses (Ahmad et al., 1986, *J. Virol.* 57:267), or Herpes virus (Spaete et al., 1982, *Cell* 30:295).

V. Measuring Genome Stability

Methods are provided for increasing genome stability and/or increasing telomere length in ES cells or a population of ES cells (such as Zscan4$^+$ ES cells). In particular examples, genome stability is increased in an ES cell by at least 20%, at least 40%, at least 50%, at least 60%, at least 75%, at least 80%, at least 90%, at least 95%, or at least 98%, for example relative to an ES cell not expressing Zscan4 (or value or range of values expected in a Zscan4$^-$ ES cell) or relative to mouse embryo fibroblast (MEF) cells or skin fibroblast cells. Methods of measuring genome stability and telomere length are routine in the art, and the disclosure is not limited to particular methods. The particular examples provided herein are exemplary.

In some examples, genome stability in an ES cell, such as a Zscan4$^+$ ES cell, is measured by detecting cell proliferation. Genome stability is increased if cell proliferation is increased, for example relative to Zscan4$^-$ ES cells. For example, ES cell proliferation can be detected by growing ES cells in culture and measuring the doubling time of the cells after each passage. In one example, genome stability is increased if crisis (e.g., cell death) does not occur at passage 8 or earlier.

In some examples, genome stability in an ES cell, such as a Zscan4$^+$ ES cell, is measured by performing karyotype analysis. Genome stability is increased if the presence of karyotype abnormalities (such as chromosome fusions and fragmentations) is decreased or even absent, for example relative to Zscan4⁻ ES cells. For example, karyotype analysis can be performed in an ES cell by inducing metaphase arrests, then preparing metaphase chromosome spreads.

In some examples, genome stability in an ES cell, such as a Zscan4⁺ ES cell, is measured by measuring telomere sister chromatid exchange (T-SCE). Genome stability is increased if the presence of T-SCE is increased, for example relative to Zscan4⁻ ES cells. For example, T-SCE can be measured in an ES cell by using telomere chromosome-orientation FISH (CO-FISH).

In some examples, genome stability in an ES cell, such as a Zscan4⁺ ES cell, is measured by measuring sister chromatid exchange (SCE). Genome stability is increased if the presence of SCE is decreased, for example relative to Zscan4⁻ ES cells. For example, SCE can be measured in an ES cell by detecting SCE in a metaphase spread.

In some examples, telomere length is measured in an ES cell, such as a Zscan4⁺ ES cell. In some examples, telomere length is increased in an ES cell if the length of the telomeres is greater, for example relative to telomere length in Zscan4⁻ ES cells. For example, telomere length can be detected in an ES cell by fluorescence in situ hybridization (FISH), quantitative FISH (Q-FISH), or telomere qPCR.

VI. Zscan4 Promoter Sequences and Expression Vectors

In particular examples, genome stability and/or telomere length in a population of ES cells is increased by selecting Zscan4⁺ ES cells from the population of ES cells. For example, an expression vector comprising a Zsan4 promoter sequence operably linked to a nucleic acid sequence encoding a heterologous polypeptide (such as a reporter gene) can be used to identify cells that express Zscan4. Methods of detecting expression of the reporter gene, and thus the Zscan4+ ES cells, vary depending upon the type of reporter gene and are well known in the art. For example, when a fluorescent reporter is used, detection of expression can be achieved by FACS or fluorescence microscopy. Identification of a subpopulation of stem cells expressing Zscan4 can be achieved with alternative methods, including, but not limited to, using antibodies specific for Zscan4 or by in situ hybridization.

In some examples a heterologous nucleic acid sequence (such as a reporter molecule) is expressed under the control of a Zscan4 promoter (for example in a vector). In some embodiments, the Zscan4 promoter is a Zscan4c promoter. For example, the Zscan4c promoter can include the nucleic acid sequence set forth as nucleotides 906-4468 of SEQ ID NO: 38. In some examples, the Zscan4c promoter comprises Zscan4c exon and/or intron sequence. Other expression control sequences, including appropriate enhancers, transcription terminators, a start codon (i.e., ATG) in front of a protein-encoding gene, splicing signals for introns, and stop codons can be included with the Zscan4 promoter in an expression vector. Generally the promoter includes at least a minimal sequence sufficient to direct transcription of a heterologous nucleic acid sequence. In several examples, the heterologous nucleic acid sequence encodes a reporter molecule.

In other examples, a heterologous nucleic acid sequence (such as a reporter molecule) is incorporated into a subject's genomic DNA, such as by homologous recombination. For example, the coding sequence for GFP could be inserted into the coding region of ZSCAN4, or could replace the coding region of ZSCAN4, ushc that GFP is expressed in the same manner as endogenous Zscan4. Gene "knock-in" methods by homologous recombination are well known in the art.

The heterologous protein encoded by the heterologous nucleic acid sequence is typically a reporter molecule, such as a marker, an enzyme, a fluorescent protein, a polypeptide that confers antibiotic resistance to the cell or an antigen that can be identified using conventional molecular biology procedures. Reporter molecules can be used to identify a cell, or a population of cells, of interest, such as Zscan4⁺ ES cells. In one embodiment, the heterologous protein is a fluorescent marker (such as a green fluorescent protein, or a variant thereof, e.g. Emerald (Invitrogen, Carlsbad, Calif.)) an antigenic marker (such as human growth hormone, human insulin, human HLA antigens); a cell-surface marker (such as CD4, or any cell surface receptor); or an enzymatic marker (such as lacZ, alkaline phosphatase). Expression of the reporter gene indicates the cell expresses Zscan4. Methods of detecting expression of the reporter gene vary depending upon the type of reporter gene and are well known in the art. For example, when a fluorescent reporter is used, detection of expression can be achieved by FACS or fluorescence microscopy.

Expression vectors typically contain an origin of replication as well as specific genes which allow phenotypic selection of the transformed cells, such as an antibiotic resistance gene. Vectors suitable for use are well known in the art, including viral vectors and plasmid vectors (such as those described in Section IV above). In one example, an enhancer is located upstream of the Zscan4 promoter, but enhancer elements can generally be located anywhere on the vector and still have an enhancing effect. However, the amount of increased activity will generally diminish with distance. Additionally, two or more copies of an enhancer sequence can be operably linked one after the other to produce an even greater increase in promoter activity.

Expression vectors including a Zscan4 promoter can be used to transform host cells, such as, but not limited to ES cells. Biologically functional viral and plasmid DNA vectors capable of expression and replication in a host are known in the art, and can be used to transfect any cell of interest.

A "transfected cell" is a host cell into which (or into an ancestor of which) has been introduced a nucleic acid molecule (e.g., DNA molecule), such as a DNA molecule including a Zscan4 promoter element. Transfection of a host cell with a recombinant nucleic acid molecule may be carried out by conventional techniques as are well known to those skilled in the art. As used herein, transfection includes liposomal-mediated transfection, electroporation, injection or any other suitable technique for introducing a nucleic acid molecule into a cell.

VII. Isolation of Embryonic Stem Cells

Mammalian ES cells, such as murine, primate or human ES cells, can be utilized with the methods disclosed herein. ES cells can proliferate indefinitely in an undifferentiated state. Furthermore, ES cells are pluripotent cells, meaning that they can generate all of the cells present in the body (bone, muscle, brain cells, etc.). ES cells have been isolated from the inner cell mass (ICM) of the developing murine blastocyst (Evans et al., *Nature* 292:154-156, 1981; Martin et al., *Proc. Natl. Acad. Sci.* 78:7634-7636, 1981; Robertson et al., *Nature* 323: 445-448, 1986). Additionally, human cells with ES properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human and non-human primate embryonic stem cells have been produced (see U.S. Pat. No. 6,200,806).

As disclosed in U.S. Pat. No. 6,200,806, ES cells can be produced from human and non-human primates. In one embodiment, primate ES cells are cells that express SSEA-3; SSEA-4, TRA-1-60, and TRA-1-81 (see U.S. Pat. No. 6,200,806). ES cells can be isolated, for example, using ES medium, which consists of 80% Dulbecco's modified Eagle's medium (DMEM; no pyruvate, high glucose formulation, Gibco BRL), with 20% fetal bovine serum (FBS; Hyclone), 0.1 mM B-mercaptoethanol (Sigma), 1% non-essential amino acid stock (Gibco BRL). Generally, primate ES cells are isolated on a confluent layer of murine embryonic fibroblast in the presence of ES cell medium. In one example, embryonic fibroblasts are obtained from 12 day old fetuses from outbred mice (such as CF1, available from SASCO), but other strains may be used as an alternative. Tissue culture dishes treated with 0.1% gelatin (type I; Sigma) can be utilized. Distinguishing features of ES cells, as compared to the committed "multipotential" stem cells present in adults, include the capacity of ES cells to maintain an undifferentiated state indefinitely in culture, and the potential that ES cells have to develop into every different cell types. Unlike mouse ES cells, human ES (hES) cells do not express the stage-specific embryonic antigen SSEA-1, but express SSEA-4, which is another glycolipid cell surface antigen recognized by a specific monoclonal antibody (see, e.g., Amit et al., *Devel. Biol.* 227:271-278, 2000).

For rhesus monkey embryos, adult female rhesus monkeys (greater than four years old) demonstrating normal ovarian cycles are observed daily for evidence of menstrual bleeding (day 1 of cycle=the day of onset of menses). Blood samples are drawn daily during the follicular phase starting from day 8 of the menstrual cycle, and serum concentrations of luteinizing hormone are determined by radioimmunoassay. The female is paired with a male rhesus monkey of proven fertility from day 9 of the menstrual cycle until 48 hours after the luteinizing hormone surge; ovulation is taken as the day following the leutinizing hormone surge. Expanded blastocysts are collected by non-surgical uterine flushing at six days after ovulation. This procedure generally results in the recovery of an average 0.4 to 0.6 viable embryos per rhesus monkey per month (Seshagiri et al., *Am J. Primatol.* 29:81-91, 1993).

For marmoset embryos, adult female marmosets (greater than two years of age) demonstrating regular ovarian cycles are maintained in family groups, with a fertile male and up to five progeny. Ovarian cycles are controlled by intramuscular injection of 0.75 g of the prostaglandin PGF2a analog cloprostenol (Estrumate, Mobay Corp, Shawnee, Kans.) during the middle to late luteal phase. Blood samples are drawn on day 0 (immediately before cloprostenol injection), and on days 3, 7, 9, 11, and 13. Plasma progesterone concentrations are determined by ELISA. The day of ovulation is taken as the day preceding a plasma progesterone concentration of 10 ng/ml or more. At eight days after ovulation, expanded blastocysts are recovered by a non-surgical uterine flush procedure (Thomson et al., *J Med. Primatol.* 23:333-336, 1994). This procedure results in the average production of one viable embryo per marmoset per month.

The zona pellucida is removed from blastocysts, such as by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes. After two further washes in DMEM, lysed trophoectoderm cells are removed from the intact inner cell mass (ICM) by gentle pipetting, and the ICM plated on mouse inactivated (3000 rads gamma irradiation) embryonic fibroblasts.

After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are re-plated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (PBS, without calcium or magnesium and with 2 mM EDTA) every 1-2 weeks as the cultures become dense. Early passage cells are also frozen and stored in liquid nitrogen.

Cell lines may be karyotyped with a standard G-banding technique (such as by the Cytogenetics Laboratory of the University of Wisconsin State Hygiene Laboratory, which provides routine karyotyping services) and compared to published karyotypes for the primate species.

Isolation of ES cell lines from other primate species would follow a similar procedure, except that the rate of development to blastocyst can vary by a few days between species, and the rate of development of the cultured ICMs will vary between species. For example, six days after ovulation, rhesus monkey embryos are at the expanded blastocyst stage, whereas marmoset embryos do not reach the same stage until 7-8 days after ovulation. The rhesus ES cell lines can be obtained by splitting the ICM-derived cells for the first time at 7-16 days after immunosurgery; whereas the marmoset ES cells were derived with the initial split at 7-10 days after immunosurgery. Because other primates also vary in their developmental rate, the timing of embryo collection, and the timing of the initial ICM split, varies between primate species, but the same techniques and culture conditions will allow ES cell isolation (see U.S. Pat. No. 6,200,806 for a complete discussion of primate ES cells and their production).

Human ES cell lines exist and can be used in the methods disclosed herein. Human ES cells can also be derived from preimplantation embryos from in vitro fertilized (IVF) embryos. Only high quality embryos are suitable for ES isolation. Present defined culture conditions for culturing the one cell human embryo to the expanded blastocyst have been described (see Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells with the same procedures described above for non-human primates (see U.S. Pat. No. 6,200,806).

VIII. Therapeutic Use of Zscan4+ ES Cells

Methods are provided for treating subjects in need of ES cell therapy. These methods include the use of ES cells and/or iPS cells. In particular examples, the method includes selecting a subject in need of treatment, and administering to the subject a therapeutic amount of a subpopulation of undifferentiated ES cells, wherein the subpopulation of undifferentiated ES cells are Zscan4+. In other examples, the method includes administration of more mature cells (e.g., mature neuron, muscle cells, cells of a particular organ, etc.) differentiated in vitro from the undifferentiated ES cells (particularly a Zscan4+ subpopulation.). Cells differentiated from the Zscan4+ ES or iPS cells will have better genome stability than Zscan4− cells. Administration of the Zscan4+ ES cells (either undifferentiated or more mature cells) thereby treats a disease in the subject. Methods of selecting or generating undifferentiated ES cells that express (Zscan4+) are described above.

Methods of differentiating undifferentiated ES cells in vitro are known. Differentiation of undifferentiated ES cells results in the formation of cells expressing markers known to be associated with cells that are more specialized and closer to becoming terminally differentiated cells incapable of further division or differentiation. The pathway along which cells progress from a less committed cell, to a cell that is increasingly committed to a particular cell type, and eventually to a terminally differentiated cell is referred to as progressive differentiation or progressive commitment. Cells which are more specialized (e.g., have begun to progress along a path of progressive differentiation) but not yet terminally differentiated are referred to as partially differentiated. For example US Patent Application No. 2006/0194321 describes differentiation of ES cells into endodermal cells (e.g., pancreatic), US Patent Application No. 2004/0014209 describes differentiation of ES cells into cardiac cells and US Patent Application No. 2008/0194023 describes differentiation of ES cells into vascular smooth muscle cells.

Subjects that can be treated using the methods provided herein include mammalian subjects, such as a veterinary or human subject. Subjects include a fetus, newborns, infants, children, and/or adults. In particular examples, the subject to be treated is selected, such as selecting a subject that would benefit from ES cell therapy, particularly therapy that includes administration of Zscan4+ ES cells.

Examples of disorders or diseases that can benefit from administration of ES cells, such as Zscan4+ ES cells include, cancer, autoimmune diseases, and diseases in which cell regeneration is beneficial, such as neurologic injuries or a neurodegenerative disorders, as well as blindness, deafness, tooth loss, arthritis, myocardial infarctions, bone marrow transplants, baldness, Crohn's disease, diabetes, and muscular dystrophy. In particular examples, a subject having one or more of these disorders is selected for the treatments herein disclosed.

Cancers include malignant tumors that are characterized by abnormal or uncontrolled cell growth. Patients treated with the ES cells disclosed herein may have cancer, or have had a cancer treated in the past (e.g., treated with surgical resection, chemotherapy, radiation therapy). For example, Zscan4+ES or iPS cells can be used in patients who have had a tumor removed, wherein specific cells differentiated from Zscan4+ES or iPS cells are used to reconstruct the removed tissues/organs. In addition, as genome instability is often associated with cancers, agents that can induce or enhance Zscan4 expression (e.g., expression of an exogenous Zscan4 nucleic acid molecule in the cancer cell) or activate Zscan4 pathways can be administered to prevent cancer cells from becoming more aggressive due to genome instability.

Exemplary cancers that can benefit from the Zscan4+ ES or iPS cells provided herein include but are not limited to cancers of the heart (e.g., sarcoma (angiosarcoma, fibrosarcoma, rhabdomyosarcoma, liposarcoma), myxoma, rhabdomyoma, fibroma, lipoma and teratoma), lung (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract (e.g., esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), genitourinary tract (e.g., kidney (adenocarcinoma, Wilm's tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), liver (e.g., hepatoma (hepatocellular carcinoma), cholangiocarcinoma, hepatoblastom, angiosarcoma, hepatocellular adenoma, hemangioma), bone (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors), nervous system (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma >pinealoma!, glioblastoma multiforme, oligodendroglioma, schwannoma, retinoblastoma, congenital tumors), spinal cord (neurofibroma, meningioma, glioma, sarcoma)), gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)), hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)), skin (e.g., malignant melanoma, basal cell carcinoma, squamous cell carcinoma, Karposi's sarcoma, moles, dysplastic nevi, lipoma, angioma, dermatofibroma, keloids, psoriasis), and adrenal glands (e.g., neuroblastoma).

In one example, a patient with an autoimmune disease is selected for treatment. Autoimmune diseases can result from an overactive immune response of the body against substances and tissues normally present in the body. In some examples, the autoimmune disease is be restricted to certain organs (e.g., in thyroiditis) or can involve a particular tissue in different places (e.g., Goodpasture's disease which may affect the basement membrane in both the lung and the kidney). Patients treated with the Zscan4+ ES cells disclosed herein may have an autoimmune disease. Exemplary autoimmune diseases that can benefit from the Zscan4+ ES cells provided herein include but are not limited to, rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, and pernicious anemia.

In some examples, the subject selected is one who has suffered a neurologic injury or suffers from a neurodegenerative disorder. Neurologic injuries can result from a trauma to the nervous system (such as to the brain or spinal cord or particular neurons), which adversely affects the movement and/or memory of the injured patient. Such traumas may be caused by an infectious agent (e.g., a bacterium or virus), a toxin, an injury due to a fall or other type of accident, or genetic disorder, or for other unknown reasons. Patients treated with the ES cells disclosed herein may have suffered a neurologic injury, such as a brain or spinal cord injury resulting from an accident, such as an automobile or diving accident, or from a stroke.

A neurodegenerative disease is a condition in which cells of the brain and spinal cord are lost. Patients treated with the ES cells disclosed herein may have a neurodegenerative disease. Exemplary neurodegenerative diseases that can be treated with the Zscan4+ ES cells provided herein include but are not limited to: adrenoleukodystrophy (ALD), alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjögren-Batten disease), bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjogren-Batten disease (also known as Batten disease), spinocerebellar ataxia, spinal muscular atrophy, Steele-Richardson-Olszewski disease, Tabes dorsalis, toxic encephalopathy.

Zscan4+ ES or iPS cells can be obtained or generated using the methods described herein. Methods of administering ES or iPS cells to mammalian subjects are known in the art. For example, Zscan4+ ES cells or iPS can be administered to a subject in need of such therapy via injection, such as subcutaneous, intramuscular, intradermal, intraperitoneal, intravenous or intra-arterial administration. In some examples, Zscan4+ ES or iPS cells are administered directly to the area in need of treatment, such as to a cancerous organ or tissue, or to the brain or spinal cord. In some examples, Zscan4+ ES or iPS cells are administered alone, in the presence of a pharmaceutically acceptable carrier (such as encapsulated in a suitable polymer) or in the presence of other therapeutic agents. In some embodiments, a subject is administered at least 20,000 Zscan4+ ES cells, such as at least 50,000, at least 100,000, at least 500,000, at least 1,000,000, or at least 2,000,000 Zscan4+ ES cells.

In one example, Zscan4+ ES or iPS cells are encapsulated into a semipermeable polymer membrane and the polymer membrane transplanted into a tissue site of a host subject. Such method may achieve local, long-term chronic delivery of a therapeutic substance with the capability of regulating release of the substance. See U.S. Pat. No. 5,573,528 for description of encapsulation of compounds and cells. In one embodiment, Zscan4+ ES cells are encapsulated within a polymer membrane. The encapsulated polymer membrane is then transplanted into a tissue site of a host subject. In one example, the tissue site is central nervous system, such as brain or spinal cord.

The semipermeable polymer membrane can be synthetic or natural. Examples of polymer that can be used include polyethersulfone (PES), polyacrylonitrile-co-vinyl chloride (P[AN/VC], poly(lactic acid), poly(lactic-co-glycolic acid), methylcellulose, hyaluronic acid, collagen, and the like. Delivery of encapsulated Zscan4+ ES cells within a polymer membrane can avoid host rejection and immune response to cells, and problems associated with rejection and inflammation. In addition, cells contained within the polymer membrane are shielded by the wall of the polymer (i.e., the walls of the individual fibers, fibrils, films, sprays, droplets, particles, etc.) from immune surveillance while still maintaining cell viability and allowing transport of molecules, nutrients and metabolic products through the polymer walls. The grafting of polymer-encapsulated cells has been developed by Aebischer et al., 1991, *Transplant*, 111:269-275, and has been successfully used with both non-human primates and humans (Aebischer et al., 1994, *Transplant*, 58:1275-1277). See also U.S. Pat. No. 6,110,902.

In one example, Zscan4+ ES or iPS cells are encapsulated by first embedding them into a matrix of either collagen, agarose or PVA (polyvinylalcohol). Subsequently, the embedded cells are injected into hollow fibers made of polypropylene of a 60:40 copolymer of polyacrylnitrile:polyvinylchloride. The fibers are cut into pieces and end-sealed for implantation. In one example, the encapsulated cells have about 20,000 to about 2,000,000 Zscan4+ ES cells.

In some examples, the Zscan4+ ES or iPS cells are of exogenous origin. By the term "exogenous" is meant cells obtained from sources other than the subject in which they are implanted for treatment. Exogenous cells can be from other organisms of the same species (such as human-derived cells for use in a human patient). Exogenous cells can also be from heterologous sources, i.e., from a species distinct from the subject to be therapeutically treated (such as mouse cells for use in a human). Zscan4+ ES or iPS cells can also be taken from an isogenic source, i.e., from the subject who is to receive the cells. After harvesting the cells from the subject, the cells can be genetically modified (e.g., a nucleic acid encoding Zscan4 is introduced) or selected/enriched for Zscan4+ ES or iPS cells, then reimplanted back to the subject. Since the cells are isogeneic, no immune response is expected.

In one aspect, the Zscan4+ ES or iPS cells are immortalized. For example and not by way of limitation, cells can be conditionally immortalized (such that the cells grow well in tissue culture at reduced temperatures, yet discontinue division once implanted into a patient and maintained at 37° C.) or constitutively immortalized (e.g., transfection with constructs expressing large T antigen, or immortalization by Epstein Barr virus) by methods well known in the art.

Another method of delivering Zscan4+ ES or iPS cells into a host subject is to directly transplant the cells into the target area of a tissue site. Once transplanted, these cells survive, migrate and integrate seamlessly into the host tissue. In one example, the Zscan4+ ES or iPS cells are directly transplanted into the nervous system of the host subject, such as a developing nervous system or a nervous system that has suffered a trauma or in a subject having a neurological disorder. When transplanted into a developing nervous system, the Zscan4+ ES cells will participate in processes of normal development and will respond to the host's developmental cues. The transplanted neural precursor cells will migrate along established migratory pathways, will spread widely into disseminated areas of the nervous system and will differentiate in a temporally and regionally appropriate manner into progeny from both the neuronal and glial lineages in concert with the host developmental program. The transplanted Zscan4+ ES or iPS cell is capable of non-disruptive intermingling with the host neural precursor cells as well as differentiated cells. The transplanted cells can replace specific deficient neuronal or glial cell populations, restore defective functions and can express foreign genes in a wide distribution.

The Zscan4+ ES or iPS cells can also be transplanted into a developed nervous system. The transplanted neural precursor cells can form a stable graft, migrate within the host nervous system, intermingle and interact with the host neural progenitors and differentiated cells. They can replace specific deficient neuronal or glial cell populations, restore deficient functions and activate regenerative and healing processes in the host's nervous system. In one example, the stable graft is a graft established in the central nervous system or the peripheral nervous system.

Similar methods can be used to directly transplant Zscan4+ ES or iPS cells into any region in need of ES cell therapy. Such cells may be undifferentiated or differentiated into the desired cell type in vitro (then administered to a subject in need thereof). For example, where organ regeneration is desired, for example for replacement of organs or tissues removed to treat cancer or lost for other reasons (e.g., teeth, hair, cells of the ear or eyes, skin or muscle). In one example, Zscan4+ ES or iPS cells are directly transplanted into the heart, for example to regenerate cardiac tissue or cells lost to myocardial infarction. In one example, Zscan4+ ES or iPS cells are directly transplanted into the pancreas, for example to regenerate cells in a subject with diabetes. In one example, Zscan4+ ES or iPS cells are directly transplanted into the bone or administered systemically, for example to regenerate bone marrow cells in a subject having cancer.

The therapeutic dose and regimen most appropriate for patient treatment will vary with diseases or conditions to be treated, and according to the patient's weight and other parameters. An effective dosage and treatment protocol can be determined by conventional means, starting with a low dose in laboratory animals and then increasing the dosage while monitoring the effects, and systematically varying the dosage regimen. Numerous factors can be taken into consideration by a clinician when determining an optimal dosage for a given subject. Factors include the size of the patient, the age of the patient, the general condition of the patient, the particular disease being treated, the severity of the disease, the presence of other drugs in the patient, and the like. The trial dosages would be chosen after consideration of the results of animal studies and the clinical literature.

Accordingly, Zscan4+ ES or iPS cells are administered to subjects so as to reduce or ameliorate symptoms associated with a particular disorder. Therapeutic endpoints for the treatment of cancer can include a reduction in the size or volume of a tumor, reduction in angiogenesis to the tumor, or reduction in metastasis of the tumor. If the tumor has been removed, another therapeutic endpoint can be regeneration of the tissue or organ removed. Effectiveness of cancer treatment can be measured using methods in the art, for example imaging of the tumor or detecting tumor markers or other indicators of the presence of the cancer. Therapeutic endpoints for the treatment of autoimmune diseases can include a reduction in the autoimmune response. Effectiveness of autoimmune disease treatment can be measured using methods in the art, for example measuring of autoimmune antibodies, wherein a reduction in such antibodies in the treated subject indicates that the therapy is successful. Therapeutic endpoints for the treatment of neurodegenerative disorders can include a reduction in neurodegenerative-related deficits, e.g., an increase in motor, memory or behavioral deficits. Effectiveness of treating neurodegenerative disorders can be measured using methods in the art, for example by measuring cognitive impairment, wherein a reduction in such impairment in the treated subject indicates that the therapy is successful. Therapeutic endpoints for the treatment of neurologic injuries can include a reduction in injury-related deficits, e.g., an increase in motor, memory or behavioral deficits. Effectiveness of treating neurologic injuries can be measured using methods in the art, for example by measuring mobility and flexibility, wherein an increase in such in the treated subject indicates that the therapy is successful. Treatment does not require 100% effectiveness. A reduction in the disease (or symptoms thereof) of at least about 10%, about 15%, about 25%, about 40%, about 50%, or greater, for example relative to the absence of treatment with Zscan4+ ES or iPS cells, is considered effective.

In some examples, Zscan4+ ES or iPS cells are administered at a dose from about $1 \times 10^4$ cells to about $1 \times 10^7$ cells in a mouse or other small mammal, or a dose from about $1 \times 10^4$ cells to about $1 \times 10^{10}$ cells in a human or other large mammal. In one specific, non-limiting example, a therapeutically effective amount is about $1 \times 10^6$ cells. Other therapeutic agents (for example, chemical compounds, small molecules, or peptides) can be administered in a therapeutically effective dose in combination with the Zscan4+ ES cells (for example shortly before or after, or simultaneously) in order to achieve a desired effect in a subject being treated. An effective amount of Zscan4+ ES cells may be administered in a single dose, or in several doses, for example daily, during a course of treatment. However, one skilled in the art will appreciate that the effective amount of Zscan4+ ES cells will be dependent on the agent applied, the subject being treated, the severity and type of the affliction, and the manner of administration of the agent.

IX. Use of Zscan4 Polypeptides and Polynucleotides

It is disclosed herein that expression of Zscan4 increases genome stability, protects cells against DNA damage and enhances DNA repair. Thus, provided herein is a method of treating a subject with cancer by administering to the subject a Zscan4 polypeptide or polynucleotide. In some embodiments, the method further includes selecting a patient in need of such therapy, such as a subject that has been diagnosed with cancer.

In some embodiments of the methods disclosed herein, the subject is administered a Zscan4 polynucleotide. In some examples, the subject is administered a vector comprising a Zscan4 polynucleotide. Methods of generating and using Zscan4-expressing vectors are described in other sections of the application. In some cases, the Zscan polynucleotide (or vector comprising the Zscan4 polynucleotide) is administered directly to tumor cells to tumor tissue, such as by injection.

In other embodiments, subject is administered a Zscan4 polypeptide. In some examples, the Zscan4 polypeptide is encapsulated by a nanoparticle to aid in delivery of the Zscan4 polypeptide to tumor cells. Suitable nanoparticles for use with the disclosed methods are known in the art and are described below.

Nanoparticles are submicron (less than about 1000 nm) sized drug delivery vehicles that can carry encapsulated drugs such as synthetic small molecules, proteins, peptides and nucleic acid based biotherapeutics for either rapid or controlled release. A variety of molecules (e.g., proteins, peptides and nucleic acid molecules) can be efficiently encapsulated in nanoparticles using processes well known in the art.

The nanoparticles for use with the compositions and methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles comprising poly(lactic acid) or poly (glycolic acid), or both poly(lactic acid) and poly(glycolic acid). In particular embodiments, the nanoparticles are poly (D,L-lactic-co-glycolic acid) (PLGA) nanoparticles.

PLGA is a FDA-approved biomaterial that has been used as resorbable sutures and biodegradable implants. PLGA nanoparticles have also been used in drug delivery systems for a variety of drugs via numerous routes of administration including, but not limited to, subcutaneous, intravenous, ocular, oral and intramuscular. PLGA degrades into its monomer constituents, lactic and glycolic acid, which are natural byproducts of metabolism, making the material highly biocompatible. In addition, PLGA is commercially available as a clinical-grade material for synthesis of nanoparticles.

Other biodegradable polymeric materials are contemplated for use with the compositions and methods described herein, such as poly(lactic acid) (PLA) and polyglycolide (PGA). Additional useful nanoparticles include biodegradable poly (alkylcyanoacrylate) nanoparticles (Vauthier et al., *Adv. Drug Del. Rev.* 55: 519-48, 2003). Oral adsorption also may be enhanced using poly(lactide-glycolide) nanoparticles coated with chitosan, which is a mucoadhesive cationic polymer. The manufacture of such nanoparticles is described, for example, by Takeuchi et al. (*Adv. Drug Del. Rev.* 47: 39-54, 2001).

Among the biodegradable polymers currently being used for human applications, PLA, PGA, and PLGA are known to be generally safe because they undergo in vivo hydrolysis to harmless lactic acid and glycolic acid. These polymers have been used in making sutures when post-surgical removal is not required, and in formulating encapsulated leuprolide acetate, which has been approved by the FDA for human use (Langer and Mose, *Science* 249:1527, 1990); Gilding and Reed, *Polymer* 20:1459, 1979; Morris, et al., *Vaccine* 12:5, 1994). The degradation rates of these polymers vary with the glycolide/lactide ratio and molecular weight thereof. Therefore, the release of the encapsulated molecule (such as a protein or peptide) can be sustained over several months by adjusting the molecular weight and glycolide/lactide ratio of the polymer, as well as the particle size and coating thickness of the capsule formulation (Holland, et al., *J. Control. Rel.* 4:155, 1986).

In some embodiments, the nanoparticles for use with the compositions and methods described herein range in size from about 50 nm to about 1000 nm in diameter. In some cases, the nanoparticles are less than about 600 nm. In some embodiments, the nanoparticles are about 100 to about 600 nm in diameter. In some embodiments, the nanoparticles are about 200 to about 500 nm in diameter. In some embodiments, the nanoparticles are about 300 to about 450 nm in diameter. One skilled in the art would readily recognize that the size of the nanoparticle may vary depending upon the method of preparation, clinical application, and imaging substance used.

Various types of biodegradable and biocompatible nanoparticles, methods of making such nanoparticles, including PLGA nanoparticles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

The following examples are provided to illustrate certain particular features and/or embodiments. These examples should not be construed to limit the disclosure to the particular features or embodiments described.

EXAMPLES

Example 1

Experimental Procedures

ES Cell Culture

MC1 ES cells, derived from 129S6/SvEvTac (Olson et al., *Cancer Res* 63, 6602-6606, 2003), were purchased from the Transgenic Core Laboratory of the Johns Hopkins University School of Medicine, Baltimore, Md., USA. R26R3ES cells (Soriano et al., *Nat. Genet.* 21:70-71, 1999) were used as the parental line to generate pZscan4-CreERT2 cells for lineage tracking experiments. In general, all ES cell lines were cultured for 2 passages on gelatin-coated feeder-free plates before further experiments and were subsequently maintained in gelatin-coated 6-well plates in complete ES medium: DMEM (Gibco), 15% FBS (Atlanta Biologicals); 1000 U/ml leukemia inhibitory factor (LIF) (ESGRO, Chemicon); 1 mM sodium pyruvate; 0.1 mM non-essential amino acids; 2 mM GlutaMAX™; 0.1 mM beta-mercaptoethanol; and penicillin/streptomycin (50 U/50 µg/ml). For all cell lines, medium was changed daily and cells were routinely passaged every 2 to 3 days.

pZscan4-Emerald Vector Construction

A genomic region spanning 3563 bp upstream to the Zscan4c start methionine was selected as the putative-Zscan4 promoter. This DNA region was amplified from BAC RP23-6311 with high fidelity TITANIUM™ Taq (Clontech), using a forward primer (GGCAACCTTACTACTTCTATC; SEQ ID NO: 1) modified with a MluI cutting sequence at the 5' end, and a reverse primer (AGCATCAACCACTTTGGTAC; SEQ ID NO: 2). Subsequently, the PCR product was cloned into the pcDNA6.2/C-EmGFP TOPO™ vector (Invitrogen). Sequence-verified plasmid DNA was linearized by MluI digestion (to also remove the cytomegalovirus promoter) prior to cloning of the Zscan4 promoter region. The nucleotide sequence of the resulting vector is set forth as SEQ ID NO: 38.

Generation of pZscan4-Emerald ES and pZscan4-CreERT2 Cells

MC1 ES cells (for pZscan4-Emerald transfection) and R26R6 ES cells (for pZscan4-Cre ERT2 transfection) were grown on gelatin in 6-well plates, $5 \times 10^5$ cells in suspension were transfected with 1 µg of linearized pZscan4-Emerald vector or pZscan4-CreERT2 vector using Effectene™ (QIAGEN) according to manufacturer's protocol, and plated in gelatin-coated 100 mm dishes. Cells were selected with 5 μg/ml blasticidin, colonies were picked on the 8th day, expanded and frozen for further analysis.

Sorting pZscan4-Emerald ES Cells

Cells were fed at least 2 hours before harvesting by Accutase™ (Chemicon) and resuspended in Iscove's Modified Dulbecco's Medium (IMDM) containing 25 mM HEPES buffer (Chemicon) with 1% FBS and 1000 U/ml LIF. Cells were FACS-sorted according to Emerald intensity. The same gating was used for all experiments. The cells were sorted into IMDM with 35% serum, 1 mM sodium pyruvate, 2 mM GlutaMAX™, 100 μM β-mercaptoethanol, 100 U/ml Penicillin, 100 μg/ml streptomycin, 0.1 mM non-essential amino acids and 1000 U/ml LIF. For microarray experiments, RNA was collected immediately after sorting by TRIZOL™ (Invitrogen) following the manufacturer's protocol.

Double-Fluorescence RNA In Situ Hybridization

Digoxigenin (DIG)- and Biotin (BIO)-labeled RNA probes were transcribed from the PCR product templates using RNA Labeling Mix (Roche). Ethanol-precipitated probes were resuspended in water and quantified by RNA 6000 Nano Assay on a 2100 Bioanalyzer™ (Agilent Technologies). Cells ($10^5$ cells/well) were seeded in glass chamber slides, cultured for three days, fixed with paraformaldehyde (PFA), and permeabilized with 0.5% Triton X-100. Cells were washed and incubated with 1 μg/ml DIG and BIO probes for 12 hours at 60° C. in hybridization solution. Probes were detected by mouse anti-DIG antibody and by sheep anti-BIO antibody, and visualized by fluorophore-conjugated secondary antibodies. Nuclei were stained with DAPI (blue).

pZscan4-CreERT2 a Zscan4 Lineage-Tracing Vector Construction

A pCre-ERT2 ORF was subcloned into the EcoRI site of pBluescriptIISK(+) plasmid (Feil et al., *Biochem. Biophys. Res. Commun.* 237:752-7, 1997). Subsequently, the PCR fragment of the Zscan4c promoter was subcloned between EcoRV and EcoRI, located at the 5'-end of the Cre-ERT2 ORF, by blunt-end ligation. A SalI-NotI fragment containing the Zscan4c promoter-Cre-ERT2 was then subcloned into the HindIII-PmeI fragment of pEF6/V5-His-TOPO™ by blunt-end ligation.

Tracking Zscan4 Expressing Cell-Fate Using pZscan4-Cre ERT2 System pZscan4-Cre ERT2 ES cells were grown in standard ES medium containing 100 nM tamoxifen. Biological triplicates at passages 1, 2, 3, 4 and 9 were stained for beta-galactosidase using a commercial kit (Chemicon) according to the manufacturer's protocol. In addition, cells maintained for a longer period in the presence of tamoxifen were harvested at passages 1, 2, 3 and 4, stained for beta-galactosidase with DetectaGene™ Green CMFDG LacZ Gene Expression kit (Invitrogen) and analyzed using Guava EasyCyte Mini flow cytometry system with the CytoSoft4.1 software (Guava Technologies).

Zscan4 Lineage Tracing Via Differentiation of Embryoid Bodies

For lineage tracing in embryoid bodies (EB) formation assay (Doetschman et al., *J. Embryol. Exp. Morphol.* 87:27-45, 1985), pZscan4-Cre ERT2 ES cells were grown on gelatin for 3 days in complete medium containing 100 nM tamoxifen, harvested and $4 \times 10^6$ ES were plated on 100 mm bacteriological Ultra-Low Culture Dish (Corning) in LIF-free medium without tamoxifen to form floating EB. On the 7th day, floating EB were collected and plated in gelatin coated 6-well plates in LIF-free medium without tamoxifen to allow attachment. On the $11^{th}$ day, beating areas were scored and subsequently cells were fixed in 4% PFA for LacZ staining and immunohistochemistry.

Quantitative Reverse Transcriptase Polymerase Chain Reaction (qRT-PCR)

RNA was isolated from cells by TRIZOL™ (Invitrogen) in biological triplicate.

Total RNA (1 μg) was reverse transcribed by Superscript III following the manufacturer's protocol, using 100 ng of oligo dT primer (Promega) per reaction. For qPCR, SYBR green master mix (Applied Biosystems) was used following the manufacturer's protocol, with 96-well optical plates, a 25 μl total reaction volume and 10 ng cDNA per well. Plates were run on 7900HT or 7500 system (Applied Biosystems). Fold induction was calculated by the ΔΔCt method (Livak and Schmittgen, *Method. Methods* 25:402-8, 2001) using H2A as normalizer, unless otherwise noted.

RNA Isolation, cDNA Preparation and qPCR Analysis in Mouse Preimplantation Embryos Four to six week-old B6D2F1 female mice were superovulated with 5 IU of pregnant mare's serum gonadotropin (PMSG; Sigma) and 5 IU of human chorionic gonadotropin (hCG; Sigma). Eggs or embryos for qRT-PCR experiments were collected after 20, 23, 30, 43, 55, 66, 80 and 102 hours post-hCG injection for MII, 1-cell, early and late-2 cell, 4-cell, 8-cell, morula and blastocyst embryos, respectively. Three sets of 10 synchronized eggs or embryos were stored in liquid nitrogen and mechanically ruptured by a freeze/thaw step for the cDNA preparation template. Oligo-dT primers and Super Script III Reverse Transcriptase (Invitrogen) were used according to the manufacturer's instructions. Analysis was performed on the ABI 7500 Fast Real Time PCR system (Applied Biosystems). A list of qPCR primer sequences are shown below in Table 1. Data was normalized by Chuk with the ΔΔCt method (Falco et al., *Reprod. Biomed. Online* 13:394-403, 2006; Livak and Schmittgen, *Method. Methods* 25:402-8, 2001).

TABLE 1 qPCR Primer Sequences

| Primer | | Sequence | SEQ ID NO: |
|---|---|---|---|
| AF067063 | (forward) | tcagaggggccacaagtgttc | 3 |
| AF067063 | (reverse) | cagaccaacccttgccaagctt | 4 |
| BC061212 | (forward) | ccatgcaaggtgtccactttctcac | 5 |
| BC061212 | (reverse) | ggggtccctctccatcactcacta | 6 |
| Eif1 a | (forward) | tgctcgtccggctgtgacgg | 7 |
| Eif1 a | (reverse) | gctctcagaagccaggactctgca | 8 |

TABLE 1-continued qPCR Primer Sequences

| Primer | | Sequence | SEQ ID NO: |
|---|---|---|---|
| Gm428 | (forward) | tgtacgagatcttgggccaccc | 9 |
| Gm428 | (reverse) | cacggtaacccaccagcttcctat | 10 |
| Tho4 | (forward) | atggacacttggaggcagccag | 11 |
| Tho4 | (reverse) | gacgcccagctggatgcttatc | 12 |
| Arginase II | (forward) | agaccacagcctggcaatag | 13 |
| Arginase II | (reverse) | aaggtaccacaactgccagg | 14 |
| Tcstv3_v1 | (forward) | tctccagctgttgtggaataagttcaac | 15 |
| Tcstv3_v1 | (reverse) | cttcttggctttatccatggatccctgaaggtaaatc | 16 |
| Zscan4 | (forward) | cctccctgggcttcttggcat | 17 |
| Zscan4 | (reverse) | agctgccaaccagaaagacactgt | 18 |
| Chuk | (forward) | caggaccgtgttctcaaggagctg | 19 |
| Chuk | (reverse) | gctctggtcctcatttgcttcacg | 20 |

Primers were designed with the Vector NTI software (Invitrogen, Carlsbad, CA) and tested using ovarian cDNA mixtures with Syber Green PCR Master Mix (Applied Biosystem, Foster City, CA) as previously described (Falco et al., Reprod. Biomed. Online 13:394-403, 2006).

Generation of ROSA/Empty Knock-in Parental-Cell Clones

MC1 ES cells were grown on feeders and harvested on day 3. Cells ($10^7$) were electroporated with 26 µg of linearized pMWRosaTcH vector using Gene Pulser Xcell™ electroporation system (BioRad). Subsequently, cells were plated on gelatin-coated feeder-free plates. Cells were selected for 10 days with 100 µg/ml of hygromycin. Seventeen resistant colonies were picked and knock-in was confirmed by Southern blot using random primed $^{32}$P-labeled external and internal probes (Masui et al., *Nucleic Acids Res.* 33:e43, 2005).

Construction of ROSA/Tet-Off Zscan4-Flag Targeting Vector and Generation of Tet-Zscan4c Cells and Tet-Empty Cells The backbone pZhcSfi plasmid (Masui et al., *Nucleic Acids Res.* 33:e43, 2005) was modified, and the Zeocin-resistance gene was replaced by the puromycin-resistance gene. PGKpA was replaced by SV40pA derived from pIRESpuro3 (Clontech) and inserted into the multiple cloning site. Zscan4c ORF fragments were amplified by PCR and subcloned into the modified pZhcSfi. A 6×His-FLAG epitope tag sequence was inserted into the 5' end of LoxPV to flank Zscan4c-fused C-terminal epitope tag. The ORF of Zscan4c was verified by sequencing. MC1 Rosa26 knock-in parental ES cells were co-transfected with the modified pZhcSfi carrying Zscan4c ORF and pCAGGS-Cre plasmid using Effectene™ (QIAGEN) according to manufacturer's instruction and selected by puromycin in the presence of doxycycline (0.2 µg/ml). Clones were isolated and thereafter named tet-Zscan4c cells. Modified pZhcSfi without the ORF was used to establish tet-Empty control cells.

RNA In Situ Hybridization

In situ hybridization was carried out as previously described (Carter et al., *Gene Expr. Patterns* 8:181-198, 2008). Briefly, tet-Zscan4c cells in triplicate, grown in the presence or absence of doxycycline for 3 days, were fixed in 4% PFA at 4° C. overnight. After digestion with proteinase K, cells were hybridized with 1 µg/ml digoxigenin-labeled riboprobe at 62° C. overnight. Cells were then washed, blocked, incubated with alkaline phosphatase-conjugated anti-digoxigenin antibody, and incubated with NBT/BCIP detection buffer for 30 minutes.

Zscan4 Knockdown Vector Construction

For Zscan4 knockdown experiments, four different 19-mer sequences from the Zscan4 gene were designed as shRNA for Zscan4 with a 19-mer sense oligo, a hairpin loop and an anti-sense of the same sequence. The most efficient sequence was:

Primer forward:
(SEQ ID NO: 21)
CATAACCTGAAAAAACAGAAGCCTGGCATTCCCTAAGCTTAGGGAATGCC
AGGCTTCTGCGCGTCCTTTCCACAAGATATATA, Primer reverse:
(SEQ ID NO: 22)
CATAACCTGAAAAAACAGAAGCCTGGCATTCCCTTTCGAAAGGGAATGCC
AGGCTTCTGCGCGTCCTTTCCACAAGATATATA.

shRNAs were amplified with GeneSilencer U6-GFP PCR kit (Gelantis) according to the manufacturer protocol. The shRNAs were intended to target a common sequence in the 3'-UTR of Zscan4c and Zscan4d paralogs to allow rescue by exogenous Zscan4 expression. Initially, tet-Zscan4c cells were transiently transfected by Effectene™ (QIAGEN) according to manufacturer's protocol; GFP was used as a reported gene for transfection efficiency. Cells were selected with hygromycin and clones were isolated to establish Zscan4 knockdown and rescue cells. To achieve rescue cells were incubated with complete ES medium without Dox for 3 days.

RNA was isolated; cDNA was made as described and tested by qPCR to measure Zscan4 expression.

Microarray Analysis

DNA microarray analysis of pZscan4-Emerald cells was carried out as described (Aiba et al., *DNA Res.* 16:73-80, 2009). In brief, universal mouse reference RNA (Stratagene) was labeled with Cy5-dye, mixed with Cy3-labeled samples, and used for hybridization on the NIA Mouse 44K Microarray v2.2 (Carter et al., *Genome Biol.* 6:R61, 2005) (manufactured by Agilent Technologies #014117). The intensity of each gene feature was extracted from scanned microarray images using Feature Extraction 9.5.1.1 software (Agilent Technologies). Microarray data analyses were carried out by using an application developed to perform ANOVA and other analyses (NIA Array Analysis software; see lgsun.grc.nia.nih.gov/ANOVA/) (Sharov et al., *Bioinformatics* 21:2548-9, 2005). All the DNA microarray data have been deposited in the NCBI Gene Expression Omnibus (GEO, http://www.ncbi.nlm.nih.gov/geo/) and are accessible through GEO Series accession number (GSE#15604) and the NIA Array Analysis software website (lgsun.grc.nia.nih.gov/ANOVA/) (Sharov et al., *Bioinformatics* 21:2548-9, 2005).

Generation of Zscan4 Antibodies

Polyclonal Rabbit anti-Zscan4 antibodies (Genescript), were generated according to the manufacturer's protocol, against the N-terminal epitope of Zscan4:

(SEQ ID NO: 39)
LQTNNLEFTPTDSSC.

Telomere Quantitative-Fluorescence In-Situ Hybridization (Q-FISH)

All cells were maintained in complete ES medium containing doxycycline. For Zscan4 induction, doxycycline was removed from the medium for a total of 3 days. Medium was replaced every day. On the $3^{rd}$ day, medium was supplemented with colcemid 0.1 µg/ml (Invitrogen) and incubated for 4 hours to arrest the cells in metaphase. Hypotonic 0.075 M KCl buffer was added to samples and then cells were fixed in cold methanol:acetic acid at a ratio of 3:1. Metaphase spreads were prepared. Telomere FISH was performed by Telomere peptide nucleic acid (PNA) FISH Kit/Cy3 (Dako-Cytomation) according to the manufacturer's protocol. Chromosomes were stained with 0.5 µg ml DAPI. Chromosomes and telomeres were digitally imaged on a Zeiss microscope with Cy3-DAPI filter sets. For quantitative measurement of telomere length, telomere size and fluorescence intensity was evaluated by TFL-TELO software (Poon et al., *Cytometry* 36:267-278, 1999).

Telomere Chromosome-Orientation FISH(CO-FISH)

Chromatid orientation (CO)-FISH analysis was performed as previously described (Bailey et al., *Mutagenesis* 11:139-44, 1996; Goodwin and Meyne, *Cytogenet. Cell. Genet.* 63:126-7, 1993) with several minor modifications. Briefly, ES cells were grown in either Dox+ or Dox− conditions for 3 days induction. Medium was changed every day. On the third day, 5'-bromo-2'-deoxyuridine (BrdU) was added for 12 hours to allow BrdU incorporation for one cell cycle. Colcemid 0.1 µg/ml was added for the final 4 hours. Metaphase spreads were prepared. Slides were stained with 0.5 µg/ml of Hoechst 33258 (Sigma), washed in 2× saline-sodium citrate (SSC) buffer for 20 minutes at room temperature, mounted with McIlvaine's buffer (at pH 8.0), and exposed to 365-nm ultraviolet (UV) light (Stratelinker 1800 UV irradiator) for 30 minutes. The BrdU-substituted DNA was digested with 3 units/µl of Exonuclease III (Promega) for 10 minutes at room temperature. The leading strand telomeres were revealed by 3'-Cy3-conjugated $(TTAGGG)_7$ (SEQ ID NO: 23), without a denaturation step and incubated overnight at 37° C. Chromosomes were counterstained with 1 µg/ml DAPI (Vector Laboratories).

Telomere Measurement by Quantitative Real-Time PCR

Genomic DNA was extracted from $10^6$ cells and quantified by Nanodrop. Average telomere length ratio was measured from total genomic DNA using a real-time PCR assay, as previously described (Callicott and Womack, *Comp. Med.* 56:17-22, 2006). PCR reactions were performed on the Prism 7500 Sequence Detection System (Applied Biosystems), using telomeric primers, control single-copy gene Rplp0 and PCR settings as previously described (Id.). A standard curve was made for the reference gene by serial dilutions of known amounts of DNA from 100 ng to 3.125 ng. The telomere signal was normalized to Rplp0 to generate a T/S ratio indicative of relative telomere length.

Telomerase Activity Measurement

Cells were cultured in triplicate on gelatin-coated dishes for 3 days in complete ES medium in the presence (Dox+) or absence of doxycycline (Dox−). Cell lysates were prepared from $10^6$ cells per replica. Telomerase activity was measured by telomeric repeat amplification protocol (TRAP) assay using a TRAPEZE™ Telomerase Detection Kit (Millipore) according to the manufacturer's instruction.

Karyotype Analysis

ES cell cultures were treated with 0.1 µg/ml colcemid (Invitrogen) for 2 hours to induce metaphase arrest. Metaphase chromosome spreads were prepared and stained with 0.3% Giemsa reagent for 20 minutes, and chromosomes were counted for n≥40 metaphases per sample. Results for knockdown and control cells were also verified by DAPI-staining in telomere FISH analyzed cells.

Sister Chromatid Exchange (SCE) Assay

SCE assay was performed as previously described (Perry and Wolff, *Nature* 251:156-8, 1974). Briefly, mouse ES cells were maintained in complete ES medium containing doxycycline. For Zscan4 induction, doxycycline was removed from the medium for total of 3 days. Medium with BrdU was added for the last 24 hours, allowing the cells to complete two cell cycles. Medium was supplemented with 0.1 µg/ml colcemid for the last 4 hours to arrest the cells in metaphase. Metaphase spreads were prepared and taken for SCE analysis. SCE were counted in n>50 metaphases per sample and the experiment was repeated for 3-4 independent experiments per sample (total of n>150 metaphases).

Immunofluorescence Staining Analysis

Cells were plated in 24-well plates on sterilized coverslips. Replicates were maintained in doxycycline medium (Dox+) while for three replicates doxycycline was removed (Dox−) for 3 days in order to induce Zscan4 over-expression. Medium was changed every day. Cells were either fixed in 4% PFA for 10 minutes at room temperature or taken for metaphase spreads as described above. Cells in PFA were permeabilized with 0.25% NP-40 for 10 minutes. Cells were blocked for 10 minutes at room temperature in 1% BSA, 10% FBS, and 0.2% saponin and incubated overnight at 4° C., with the primary antibodies: anti-FLAG antibody diluted 1:1000, anti-ZSCAN4 1:400, anti-SPO11 1:200, anti DMC1 1:200, anti-TRF1 1:500, anti-TRF2 1:400 in blocking solution. As negative controls, cells stained without primary antibody were used, as well as the Dox+ cells stained with anti-FLAG antibody. The bound antibody was visualized with a fluorescent Alexa546 secondary antibody (Invitrogen) under a Zeiss 510-confocal microscope. Nuclei were visualized with DAPI (Roche) staining for 5 minutes at room temperature.

Example 2

Zscan4 is Expressed in 5% of ES Cells in Undifferentiated Conditions

Figure 1A:
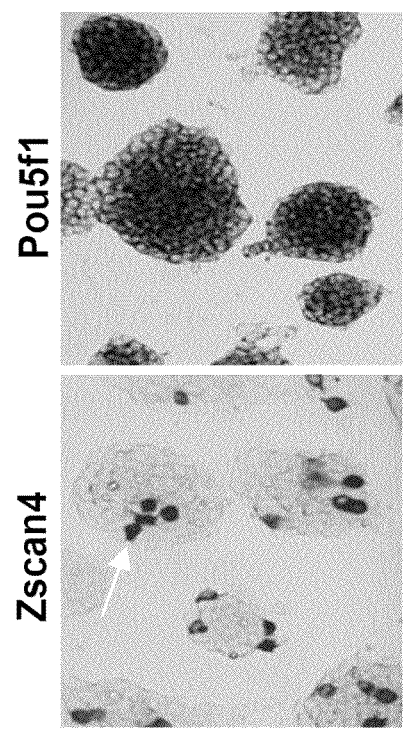
FIG. 1A is a pair of digital images showing expression of Zscan4 is highly heterogeneous in mouse ES cell colonies, as demonstrated by RNA whole-mount in situ hybridization (WISH), whereas that of control Pou5f1 is homogeneous.
Figures 1C, 1D:
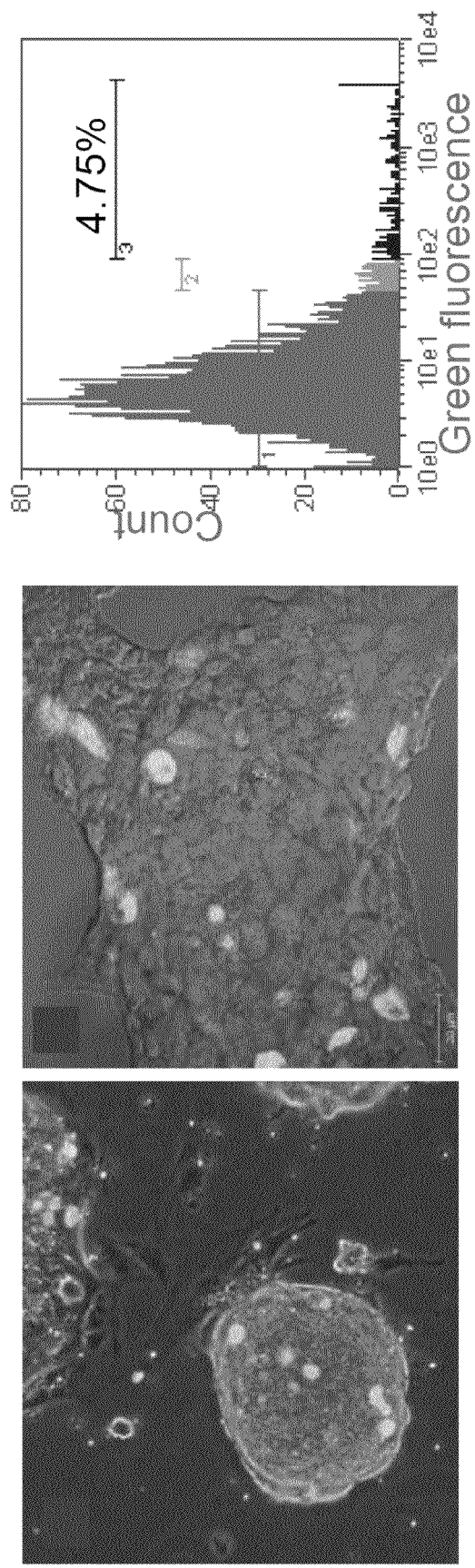
FIG. 1C is a pair of digital images showing visualization of Emerald expression under the Zscan4 promoter in pZscan4-Emerald cells by phase-contrast fluorescent microscope (left panel) and confocal microscope section (right panel). All nuclei were labeled with DAPI.
FIG. 1D is a FACS plot of pZscan4 Emerald cells.
Figure 1E:
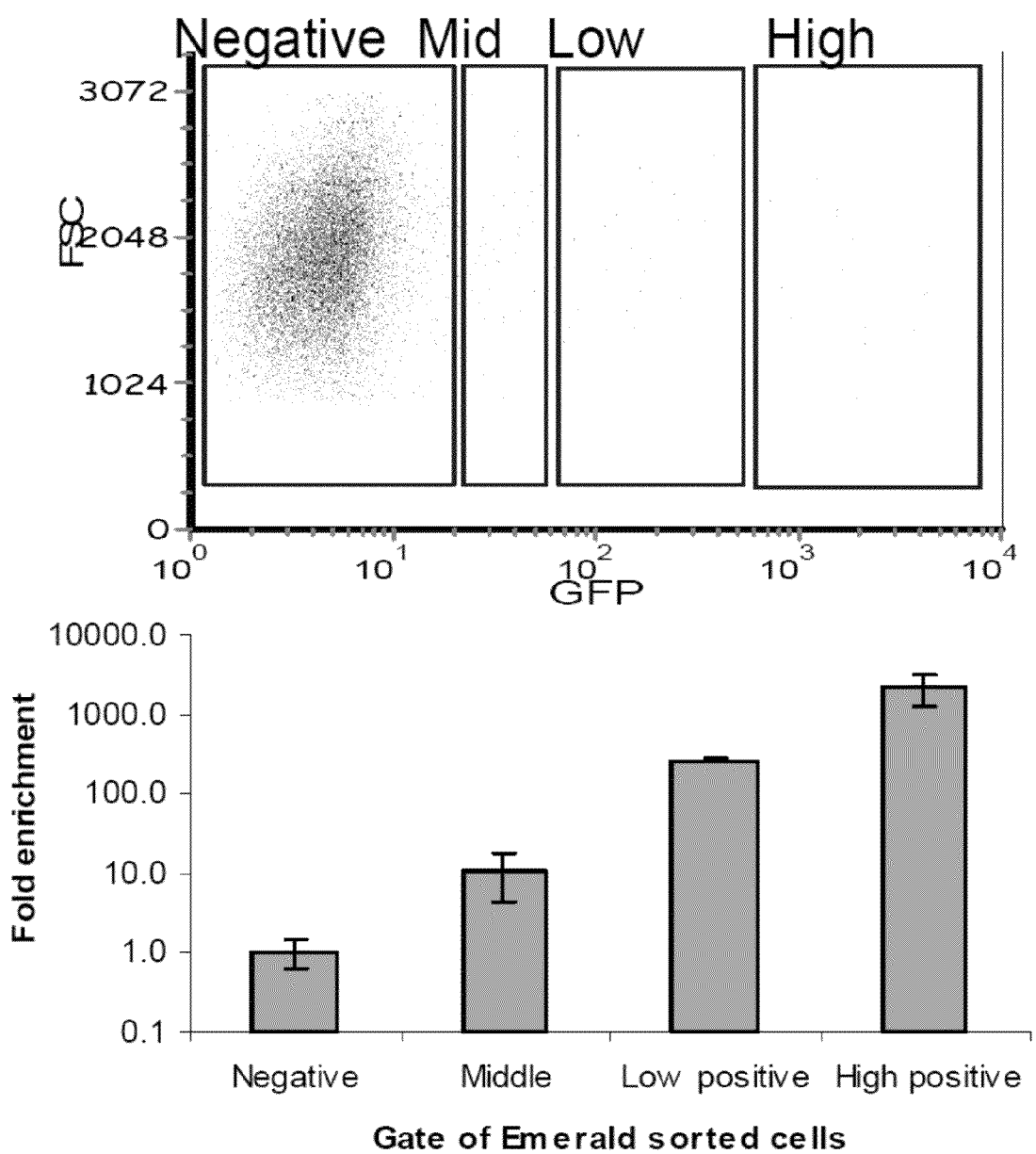
FIG. 1E shows FACS-sorting of pZscan4-Emerald cells into four groups according to their fluorescent intensities (upper panel). The expression levels of Zscan4c in each cell population were measured by qRT-PCR (lower panel).

RNA in situ hybridization of Zscan4 showed a highly heterogeneous staining pattern in MC1 mouse ES cell colonies (FIG. 1A) (Carter et al., *Gene Expr. Patterns* 8:181-198, 2008; Falco et al., *Dev. Biol.* 307:539-550, 2007). As a first step to characterize Zscan4-expressing ES cells, a reporter plasmid designed to express the green fluorescence protein (GFP)-Emerald under Zscan4c promoter (FIG. 1B) was transfected into MC1 ES cells and a stable transformant, pZscan4-Emerald cells, was isolated. As expected, Emerald expression was observed in a small number of the ES cells in culture, recapitulating previous observations by RNA in situ hybridization (FIG. 1C). FACS analysis indicated that approximately 5% of the ES cells were Emerald-positive (FIG. 1D), although the number slightly varied (2-7%) even when the same culture conditions were used. Quantitative real-time reverse-transcription polymerase chain reaction (qRT-PCR) analysis of FACS-sorted cells demonstrated about 1,000-fold enrichment of Zscan4 mRNA in Emerald(+) (Em(+)) cells relative to Em(−) cells. Furthermore, when the cells were sorted into subgroups according to respective Emerald intensity, a direct correlation between Emerald-fluorescence intensity and Zscan4 mRNA levels was observed (FIG. 1E), thus establishing that Em(+) cells are also Zscan4 (+) cells.

Example 3

Figure 1F:
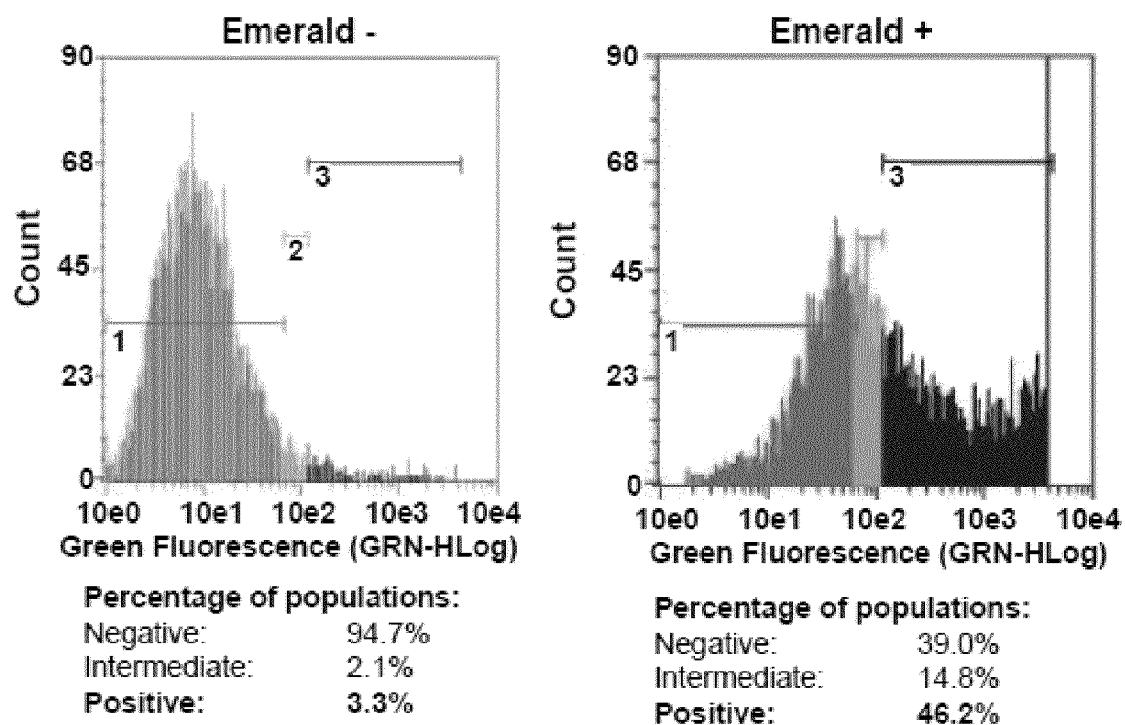
FIGS. 1F-1H are a series of FACS plots showing a time-course FACS analysis of pZscan4-Emerald cells.
Figure 1G:
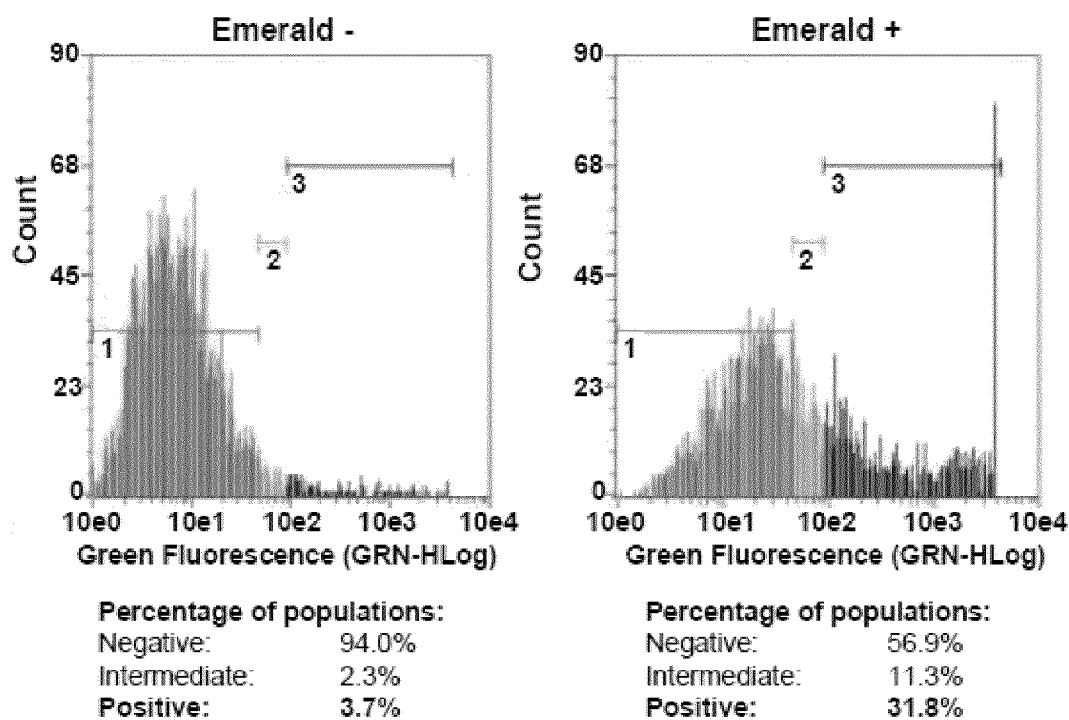
Figure 1H:
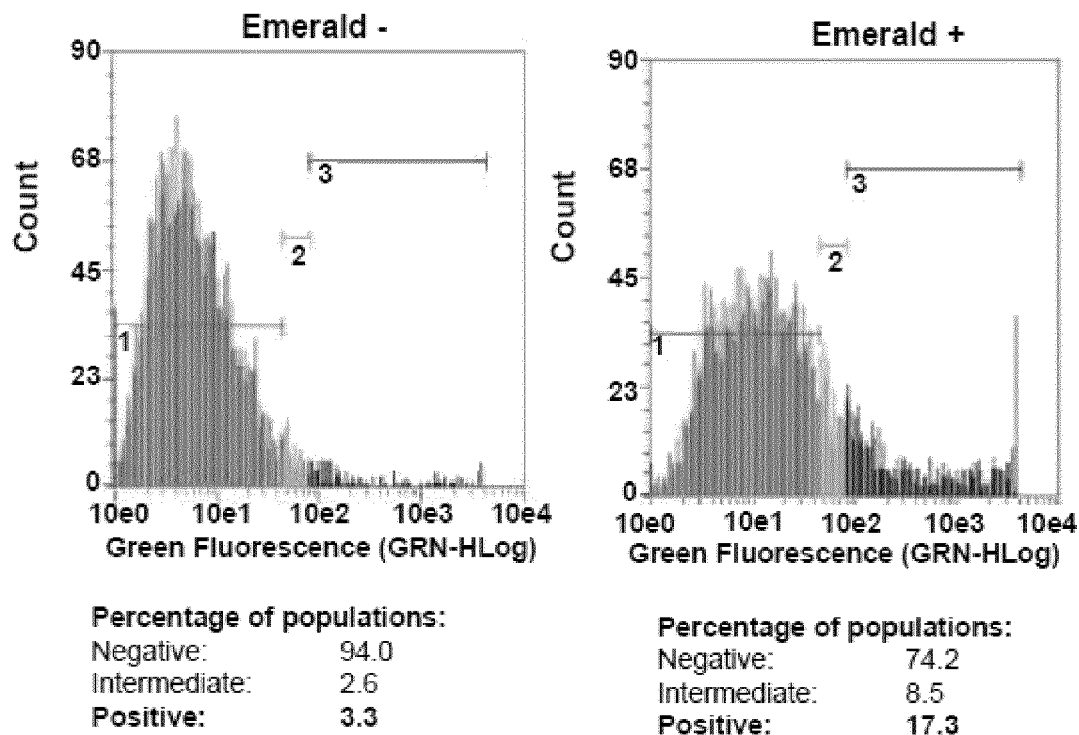

Zscan4 Expression Marks a Transient and Reversible State in Undifferentiated ES Cells To investigate whether Zscan4 expression marks distinctive cell types within ES cell colonies, pZscan4-Emerald cells were FACS-sorted into Em(+) cells and Em(−) cells, and subsequently replated separately in a standard ES cell culture medium. Both Em(+) and Em(−) cells were able to establish viable, undifferentiated ES cell colonies. However, by 24 hours in culture 54% of the Em(+) cells became Em(−), whereas 3.3% of Em(−) cells became Em(+) as shown by FACS analysis (FIGS. 1F-1H). Furthermore, live-cell imaging on pZscan4-Emerald cells in a time-lapse experiment documented the transition of cells between the two states, and confirmed that both Em(+) and Em(−) cells can replicate properly and establish new colonies with a heterogeneous Emerald expression pattern. Therefore, Zscan4 is expressed transiently in ES cells, and the transition between Zscan4(+) state and Zscan4(−) state is reversible. The transient Zscan4 (+) state of ES cells is referred to herein as "ES-star (ES*) state."

Example 4

ES* State is Associated with Up-Regulation of Early-Embryonic Markers

Figure 1I:
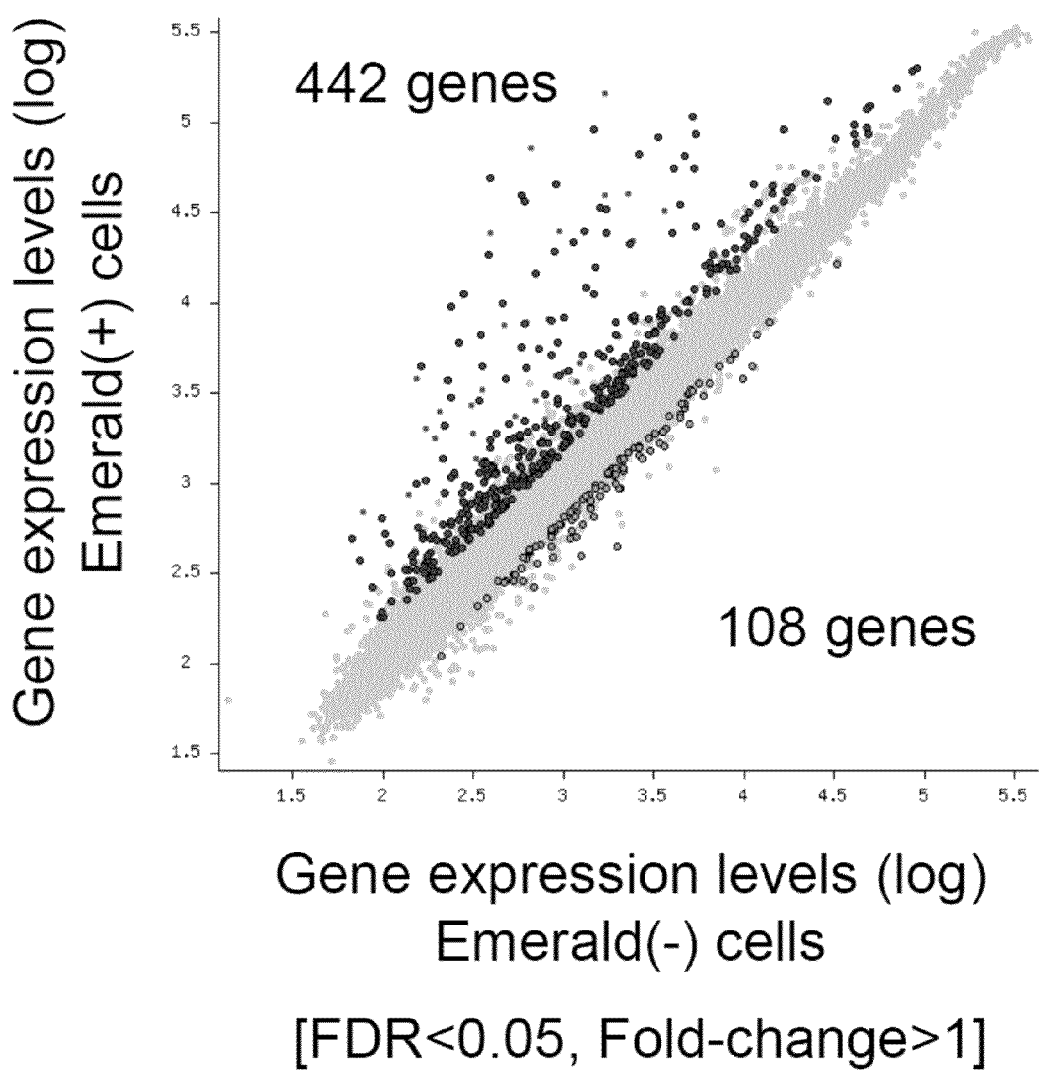
FIG. 1I is a scatter plot showing a pair-wise comparison of gene expression profiles between Emerald(+) and Emerald(−) cells by DNA microarray analysis. Color-coded spots are genes that are differentially expressed with statistical significance (FDR<0.05 and fold-change>1).

ES* state was further characterized by DNA microarray analysis of FACS-sorted Em(+) and Em(−) cells. The Em(+) cells showed a very similar gene expression profile to the Em(−) cells with only 550 differentially expressed genes (FIG. 1I). Pluripotency-related markers remained unchanged in Em(+) cells compared to Em(−) cells, but Tcstv1 and Tcstv3 (two cell-specific transcript variant 1 and 3) genes (GenBank accession AF067057.1; Zhang et al., *Nucleic Acids Res.* 34:4780-90, 2006) were found among the top 20 most highly up-regulated genes (FIG. 1J).

Figure 2A:
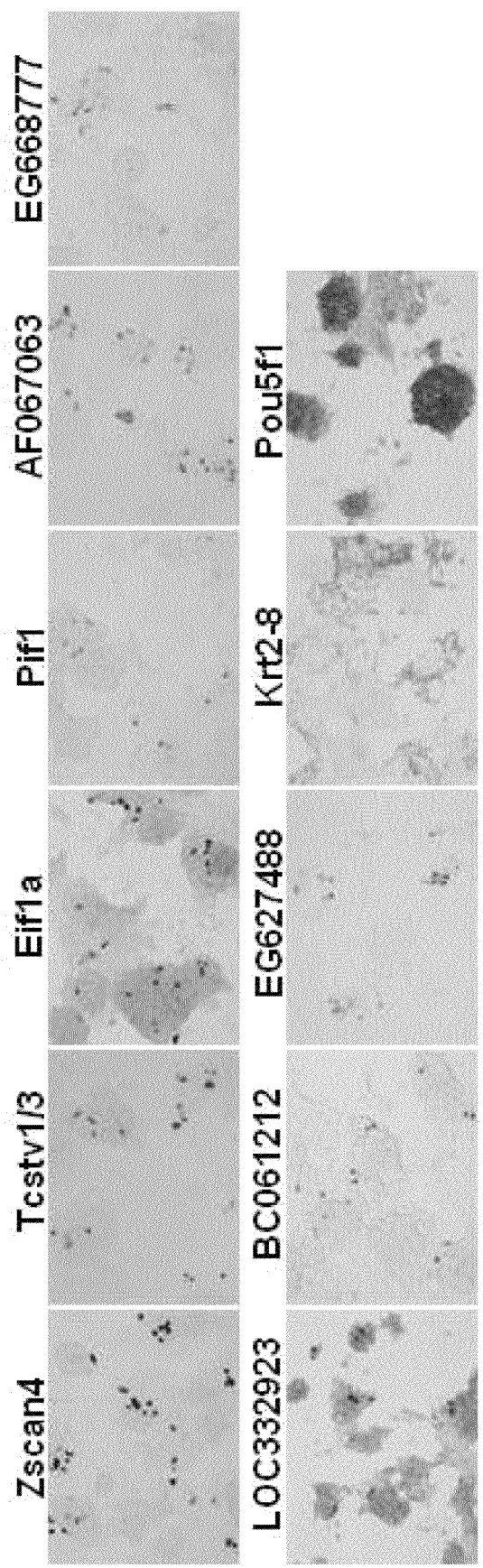
FIG. 2A is a series of digital images showing RNA in situ hybridization of Zscan4 and 8 additional genes (Tcstv1, Eif1a, Pif1, AF067063, EG668777, LOC332923, BC061212, and EG627488), selected for upregulation in Em(+) cells and showing a "Zscan4-like" expression pattern. Control genes are Krt2-8/EndoA, a trophectoderm and visceral-endoderm marker that stains differentiated cells surrounding undifferentiated ES colonies; and Pou5f1 (Oct4 or Oct3/4), as a pluripotency marker.
Figure 2B:
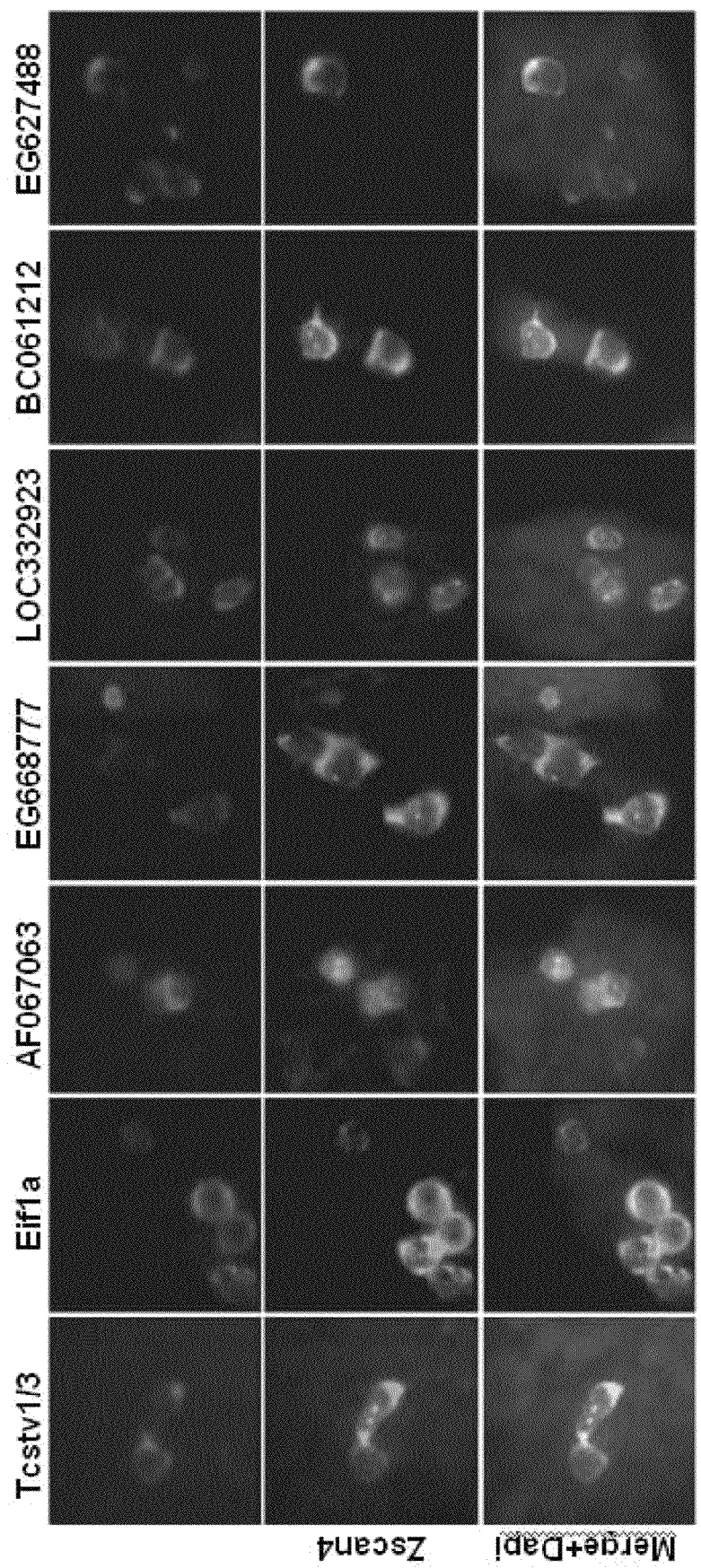
FIG. 2B is a set of digital images of double-fluorescence RNA in situ hybridization showing co-expression of Zscan4 transcript (FITC) and transcripts of: Tcstv3, Eif1a, AF067063, EG668777, LOC332923, BC061212 and EG627488.
Figure 2C:
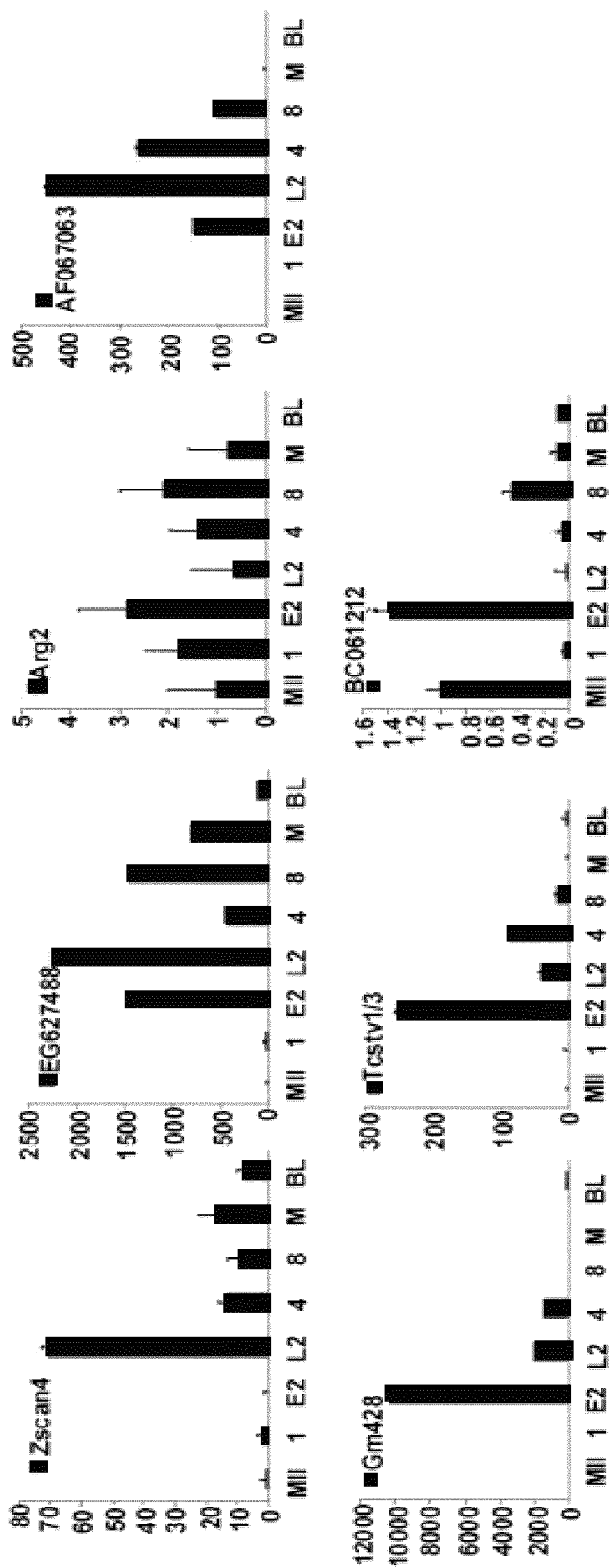
FIG. 2C is a series of bar graphs showing qRT-PCR analysis of Zscan4 and six other selected genes upregulated in Em(+) cells (EG627488, Arg2, AF067063, Gm428, Tcstv1/3, BC061212). Results from unfertilized oocytes (MII), 1-cell embryos (1), early 2-cell embryos (E2), late 2-cell embryos (L2), 4-cell embryos (4), 8-cell embryos (8), Morulae (M) and Blastocysts (BL) are shown.

RNA in situ hybridization revealed "Zscan4-like" expression for eight other genes in the list (Tcstv1/3, Eif1a, Pif1, AF067063, EG668777, LOC332923, BC061212, and EG627488) (FIG. 2A). Furthermore, double-labeling fluorescence RNA in situ hybridization confirmed co-expression of these genes with Zscan4 (FIG. 2B). As Zscan4 is a 2-cell embryo marker, the expression profile of six genes from the top 20 genes most highly upregulated in Em(+) cells were examined by qRT-PCR in preimplantation embryos. All six genes examined showed a high expression peak in 2-cell embryos; 3 genes showed the highest peak at the late 2-cell stage as Zscan4, whereas 3 others showed the highest expression at the early 2-cell stage (FIG. 2C). Taken together, these results indicate that some of the early-stage embryo programs are reactivated in the ES* state.

Example 5

Most ES Cells in Culture go Through the ES* State

Figure 3A:
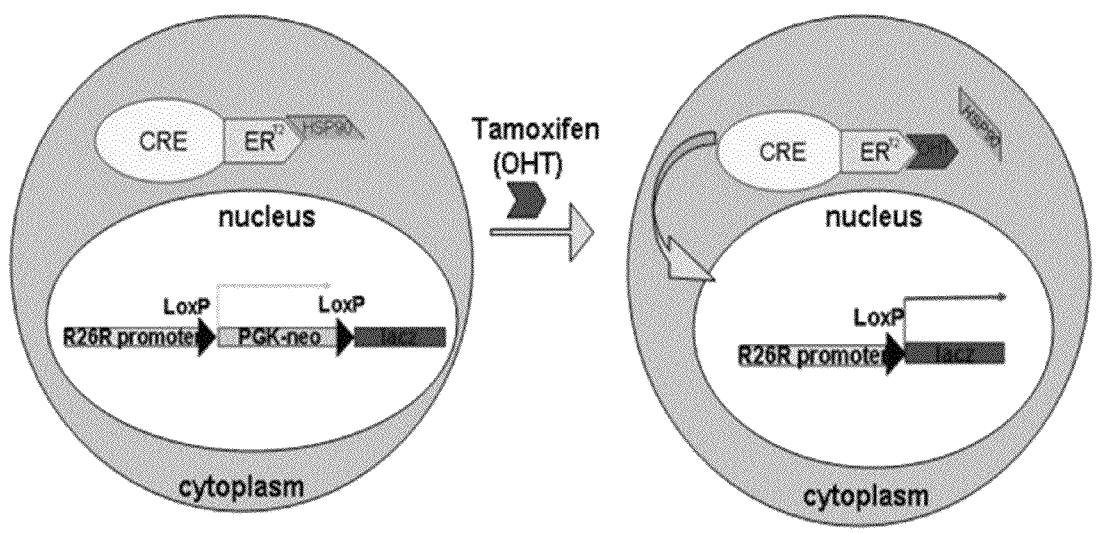
FIG. 3A is a schematic diagram of the pZscan4-CreERT2 vector. The cre-recombinase gene is expressed under the Zscan4 promoter. In the presence of tamoxifen, CreERT2 fusion enzyme translocates into the nucleus, excises the neomycin resistance gene upstream of LacZ gene, and activates LacZ expression.

To trace the fate of ES* cells, a plasmid carrying CreERT2 (Feil et al., *Biochem. Biophys. Res. Commun.* 237:752-7, 1997) driven by the Zscan4c promoter was transfected into a ROSA26-knockin ES cell line carrying a floxed neomycin cassette in a LacZ open reading frame (ORF) (Soriano, *Nat. Genet.* 21:70-71, 1999) and a stable cell line, pZscan4-CreERT2 ES cells, isolated (FIG. 3A). In this system, Cre-recombinase is expressed in cells in the ES* state, translocates from the cytoplasm into the nucleus only in the presence of tamoxifen, and excises a neomycin cassette from LacZ-ORF, leading to a constitutive LacZ expression (FIG. 3A). Cells in the ES* state are thus heritably labeled with LacZ.

Figure 3D:
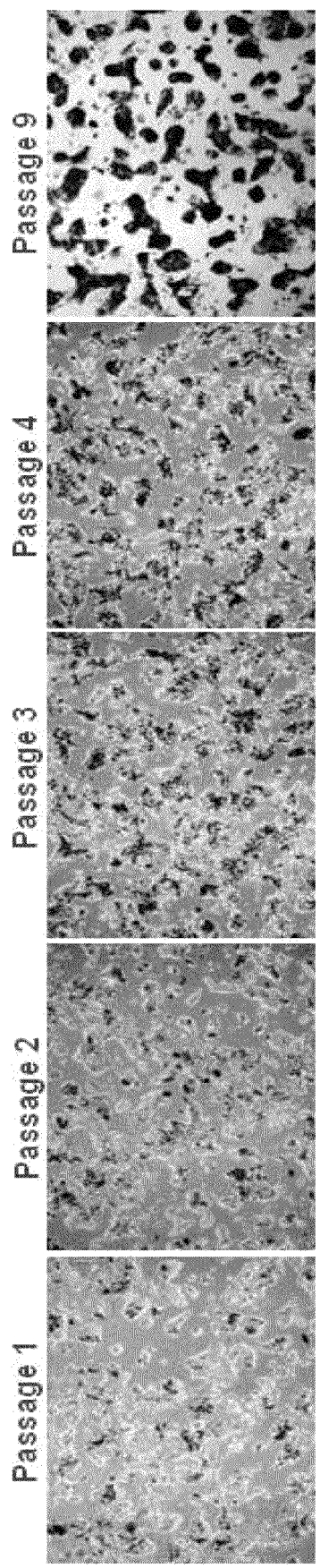
FIG. 3D is a series of phase contrast images of pZscan4-CreERT2 cells maintained in the presence of tamoxifen for up to 9 passages (27 days) and subsequently stained with X-gal to demonstrate LacZ activity. By passage 9, the majority of the cells are marked by LacZ.
Figure 3E:
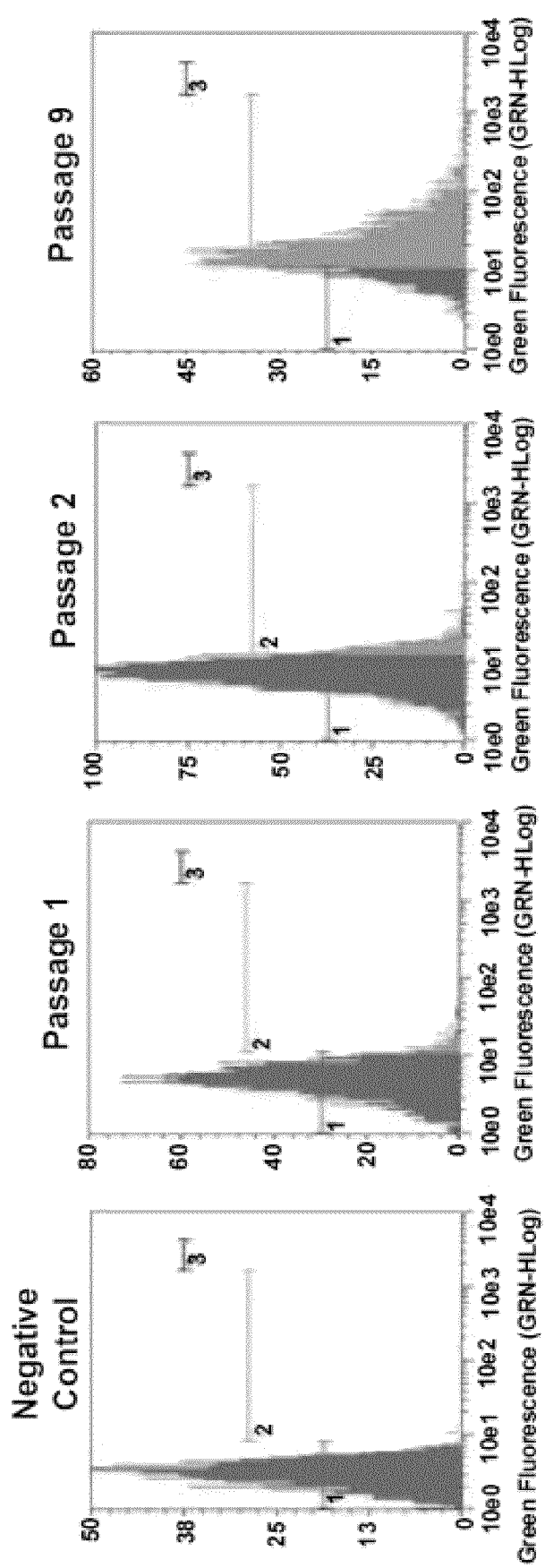
FIG. 3E is a series of FACS plots showing analysis of LacZ expression by CMFDG-staining. A continuous increase in the LacZ-positive cell population in the continuous presence of tamoxifen was observed.
Figure 3F:
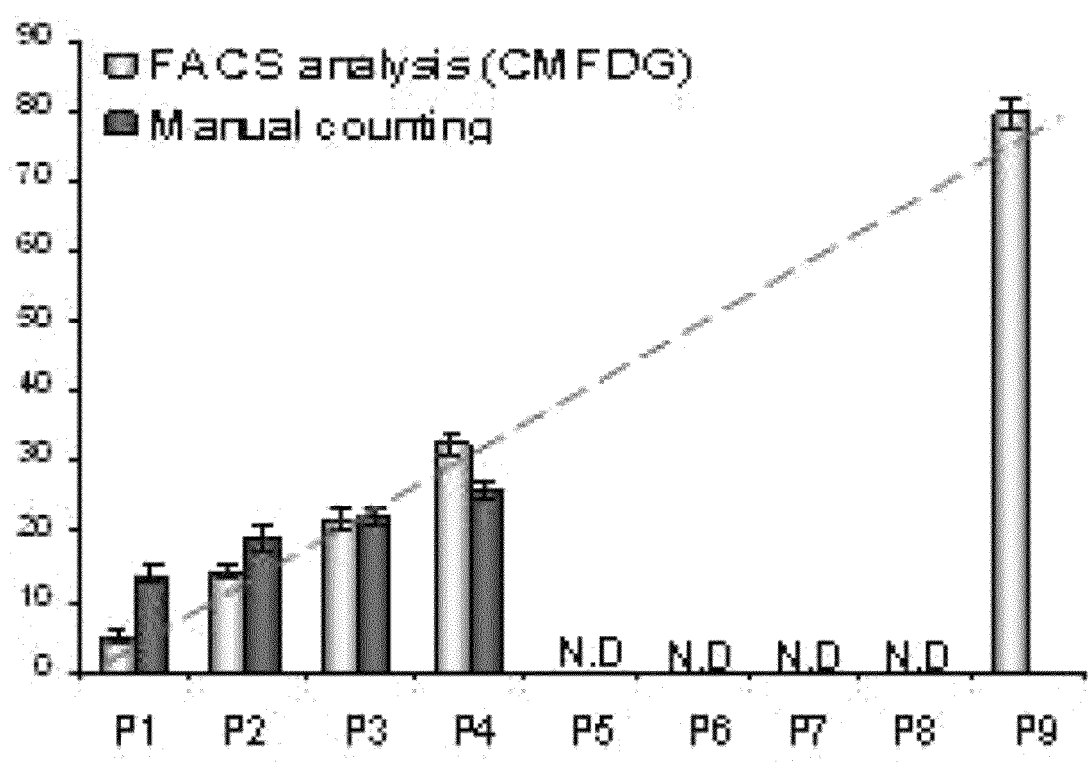
FIG. 3F is a graph showing LacZ-positive cells counted by two different methods: FACS analysis using CMFDG and manual counting after staining cells with X-gal. Both methods show similar results with linear increase of LacZ-positive cells with passages.

As expected, cells positive for Zscan4 RNA by fluorescence in situ hybridization were co-stained with nuclear-localized Cre-recombinase protein as demonstrated by immunostaining (FIG. 3B). To identify the total population of cells marked by Zscan4 expression, pZscan4-CreERT2 ES cells were maintained continuously in undifferentiated conditions in the presence of tamoxifen for 9 passages (27 days). Immunostaining analysis of the cells demonstrated that Pou5f1 (Oct4 or Oct 3/4) was co-stained with LacZ, indicating that they were still undifferentiated (FIG. 3C). Visualization of LacZ activity by X-gal staining showed that the number of cells marked with LacZ steadily increased with passages and the majority of ES cell colonies became LacZ-positive by passage 9 (FIGS. 3D and 3F). These observations were further confirmed by FACS analysis following CMFDG staining (a green fluorescence LacZ substrate) (FIGS. 3E and 3F). Taken together with the observation from pZscan4-Emerald ES cells, cell fate tracing experiments confirmed that at a given time only 5% of ES cells are positive for Zscan4 expression, but after 9 passages most ES cells in culture experience Zscan4 expression (i.e., ES* state).

Example 6

Cells in ES* State Maintain Pluripotency In Vitro and In Vivo

Figure 3G:
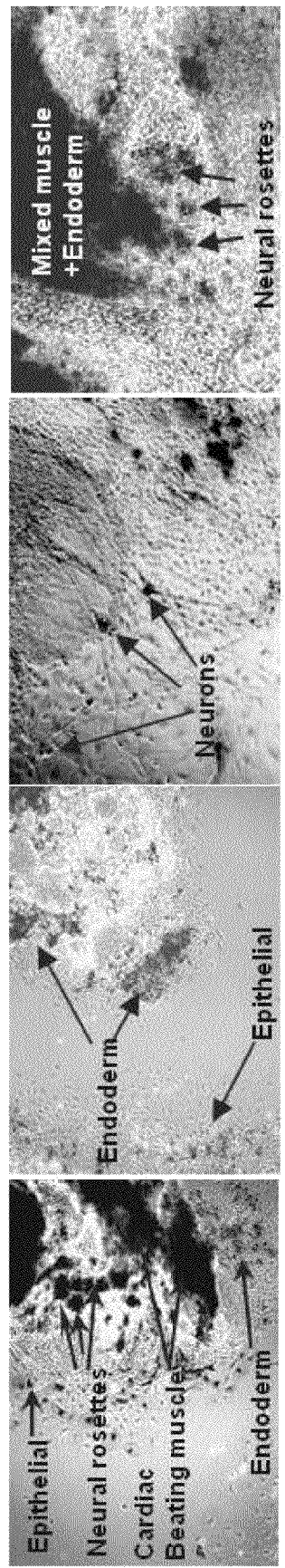
FIG. 3G is a series of digital images showing pZscan4-CreERT2 LacZ-positive cells are able to contribute to all three major cell lineages by embryoid body (EB) differentiation assay. Phase contrast images of X-gal staining of the cells show LacZ-positive Zscan4-daughter cells in endoderm, ectoderm (epithelia, neural rosettes by the 3rd day of differentiation, neurons by the 7th day of differentiation) and mesoderm (beating muscles).
Figure 3H:
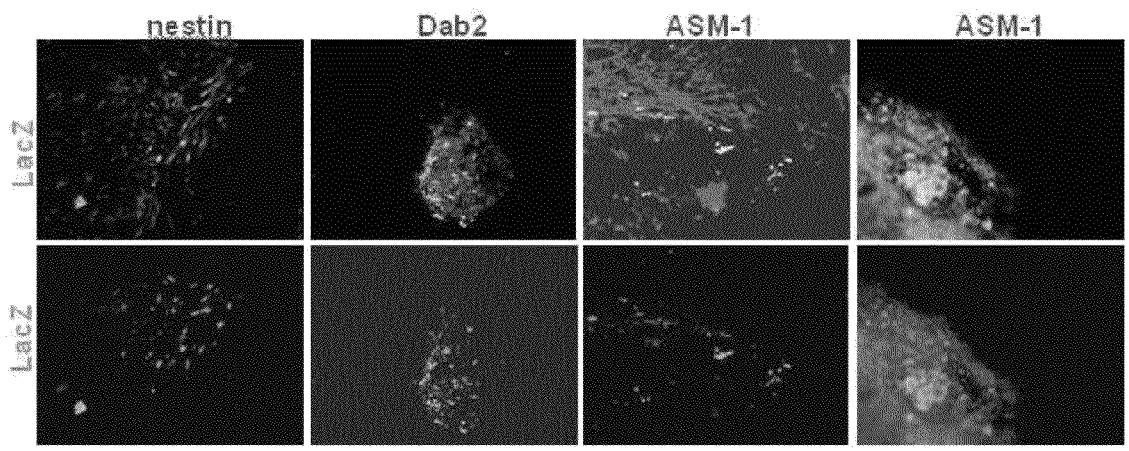
FIG. 3H is a series of digital images showing co-immunostaining for LacZ and different germ layer markers. Zscan4-daughter cells (marked by LacZ expression) are able to contribute to all three germ layers: Dab2 for endoderm; ASM-1 for mesoderm; and Nestin for neuroectoderm.

To determine if Zscan4 expression leads to a certain cell lineage commitment in ES cells, pZscan4-CreERT2 cells were exposed to a pulse of tamoxifen, followed by embryoid body (EB) formation and attachment assay (Doetschman et al., *J. Embryol. Exp. Morphol.* 87:27-45, 2007). In the EB differentiation, cells derived from the ES* state were able to contribute to a variety of cell types including lineages from all three embryonic germ layers, as judged by cell morphology as well as immunostaining for specific lineage markers (FIGS. 3G and 3H).

Figure 3I:
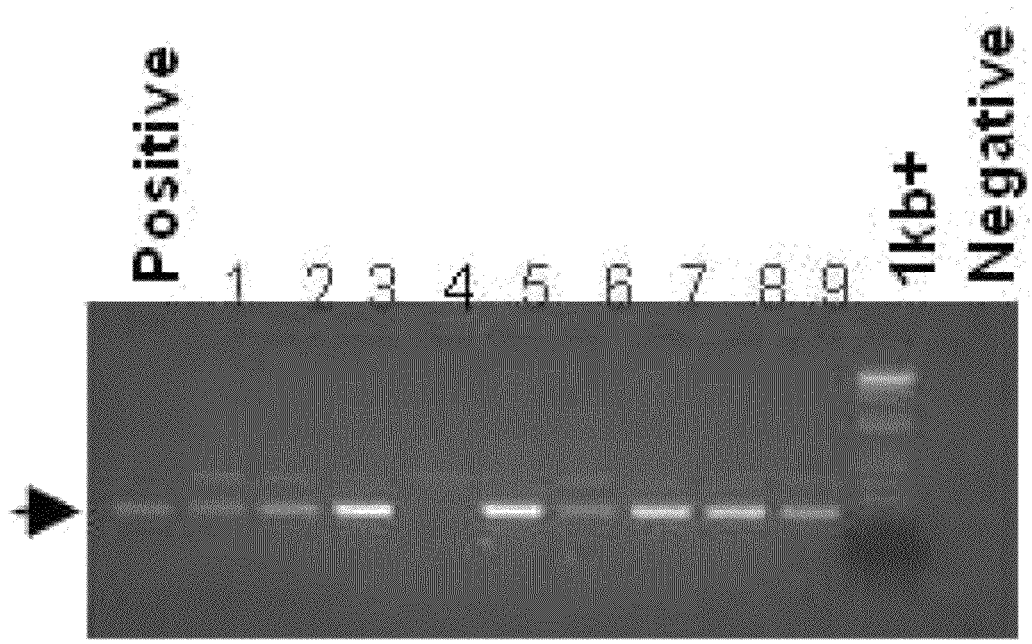
FIG. 3I is an image of a gel showing genotyping of 9 embryos (E10.5), which demonstrates chimerism in 8 out of the 9 embryos tested.

To test the pluripotency of cells in ES* state in vivo, FACS-sorted Em(+) cells were microinjected into 16 mouse blastocysts and four pups were obtained, two of which were chimeric based on coat color. In another experiment, 8 out of 9 embryos (E10.5) produced were chimeric based on genotyping by PCR analysis (FIG. 3I). Therefore, the data demonstrate that cells in ES* state retain their pluripotency in vitro and in vivo, as they can contribute to all cell lineages after in vitro differentiation by EB formation, and have the ability to form chimera in vivo. Taken together, these results indicate that physiological Zscan4 expression in cell culture is transient and reversible in undifferentiated ES cells, and does not affect the pluripotency of the cells.

Example 7

Zscan4c Knockdown Leads to a Cell Culture Crisis of ES Cells by 8 Passages

Figure 4A:
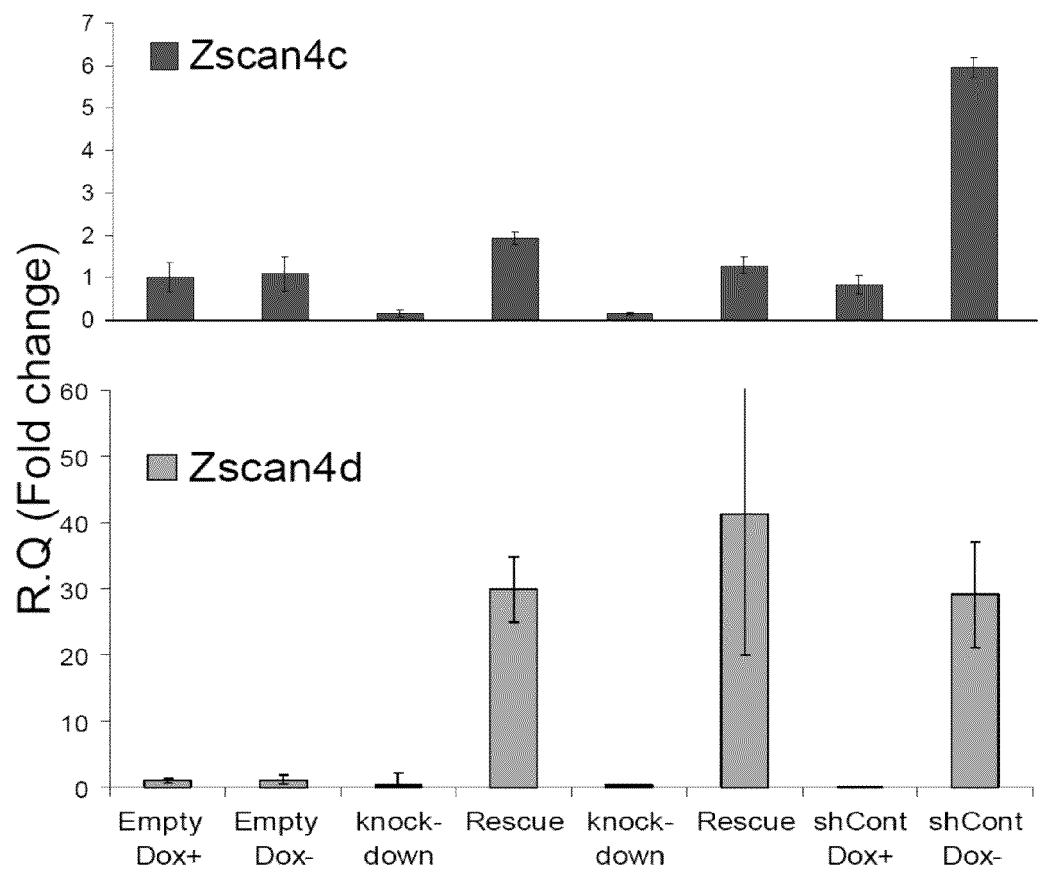
FIG. 4A is a pair of graphs showing qRT-PCR analysis demonstrating Zscan4 shRNA vector downregulated Zscan4 expression by ~90%, whereas Zscan4c-ORF induction by Dox removal rescued Zscan4 expression (upper panel). shRNA against Luciferase was used in the same parental cells as negative control. qRT-PCR analysis showed Zscan4c overexpression led to Zscan4d induction (lower panel); both paralogs were knocked down by shRNA.

To directly test whether the intermittent expression of Zscan4 is essential for ES cells, Zscan4-knockdown and -rescue cells were generated. First, tet-Zscan4c ES cells were generated by integrating a tetracycline (tet)-repressible ORF of Zscan4c into the ROSA26 locus of the mouse genome using the Cre-LoxP system (Masui et al., *Nucleic Acids Res.* 33:e4, 2005). In the tet-Zscan4c ES cells, a Venus reporter gene, linked to Zscan4c RNA by an IRES, allowed monitoring gene induction. Subsequently, tet-Zscan4c ES cells were transfected with a Zscan4-shRNA vector targeting a common 3'-untranslated region of both Zscan4c and Zscan4d, and ES cell clones with normal morphology were isolated. The system was designed to knockdown the expression of both Zscan4c and Zscan4d in the presence of doxycycline (Dox+) and to provide a rescue by expressing the exogenous copy of Zscan4c-ORF by doxycycline removal (Dox−). qRT-PCR analysis confirmed the downregulation of Zscan4c expression by 90±2.4% as well as Zscan4d by 70±7.0% (FIG. 4A). Culturing the cells in the Dox− condition for 3 days induced Zscan4c-ORF expression by 5.9±0.22 fold, whereas the control shRNA did not affect Zscan4 gene expression in the same parental cells. Zscan4c induction also resulted in upregulation of Zscan4d, a paralog expressed predominantly in the 2-cell embryo, suggesting a positive feedback between the two paralogs (FIG. 4A).

Figure 4B:
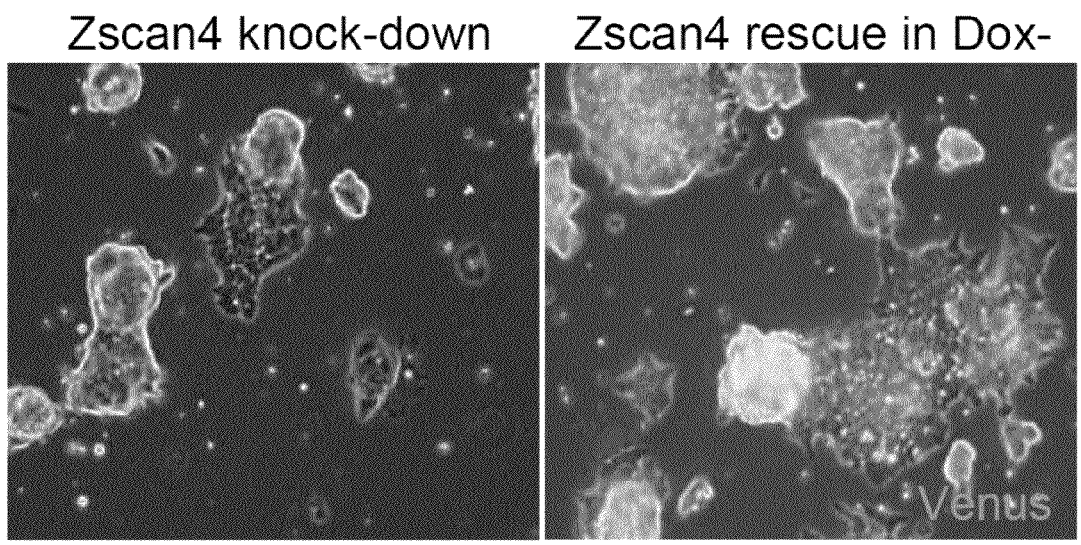
FIG. 4B is a pair of representative images of Zscan4-knockdown cells and the cells rescued by Zscan4-ORF induction by the removal of Dox for 3 days. Venus was used as a reporter for gene induction.
Figure 4C:
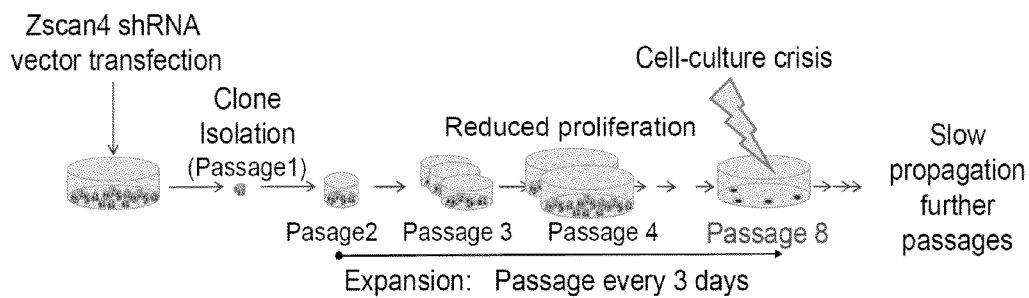
FIG. 4C is a schematic illustration of Zscan4 knockdown phenotype. Cells presented normal colony morphology during the first few passages; however, 8 passages after clone isolation (approximately 31 cell doublings), cell culture crisis was observed. The surviving cells could be maintained, but their doubling time was abnormally long.
Figure 4D:
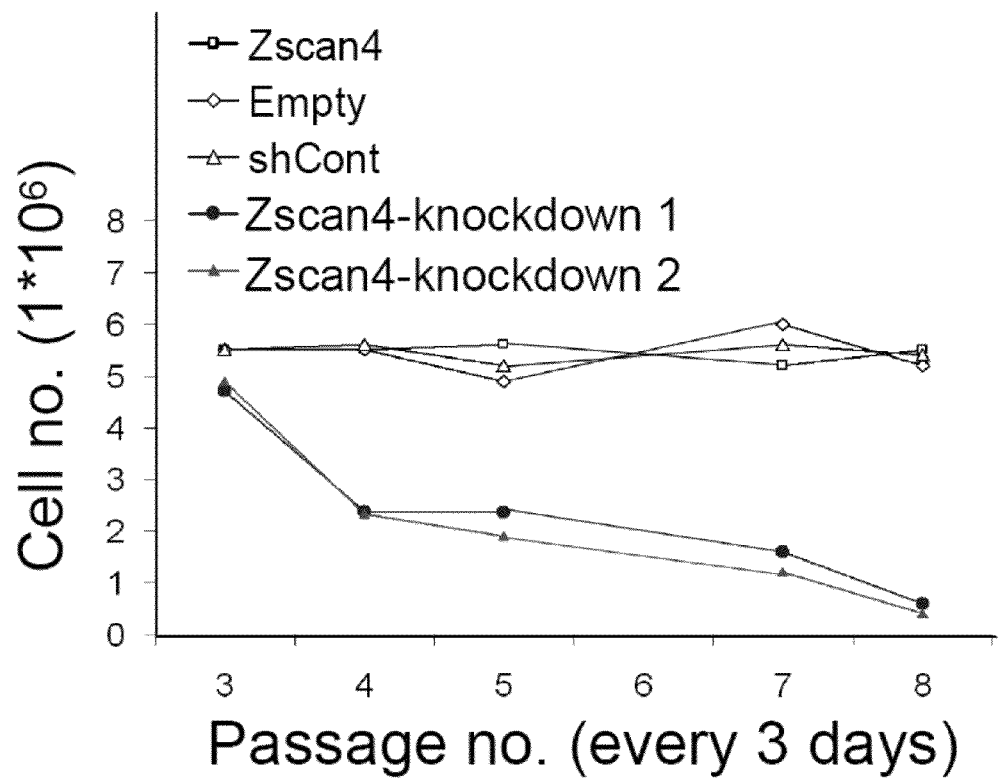
FIG. 4D is a graph showing reduced cell proliferation by Zscan4 knockdown. For each passage, 4×10$^5$ cells were plated and cells were counted after 3 days in culture.

As expected from the transient and intermittent expression of Zscan4, Zscan4-knockdown did not affect the ES cells immediately and showed typical ES cell morphology upon clonal isolation (FIG. 4B). However, with passages, the population doubling time of the Zscan4-knockdown cells became longer than control cells and flat non-dividing cells began to accumulate in culture (FIGS. 4C and 4D). During passage 8 (approximately 31 cell doublings after transfection), most of the cells died abruptly 1-2 days after plating, leaving very few surviving small colonies (FIGS. 4C and 4D). It was possible to recover the surviving colonies by passaging the cells every 3 days without splitting for two weeks. However, the surviving cells had an abnormally long doubling time. This phenotype was reproducible in multiple independent experiments.

Example 8

Decreased Cell Proliferation in Zscan4-Knockdown Cells

Figure 4E:
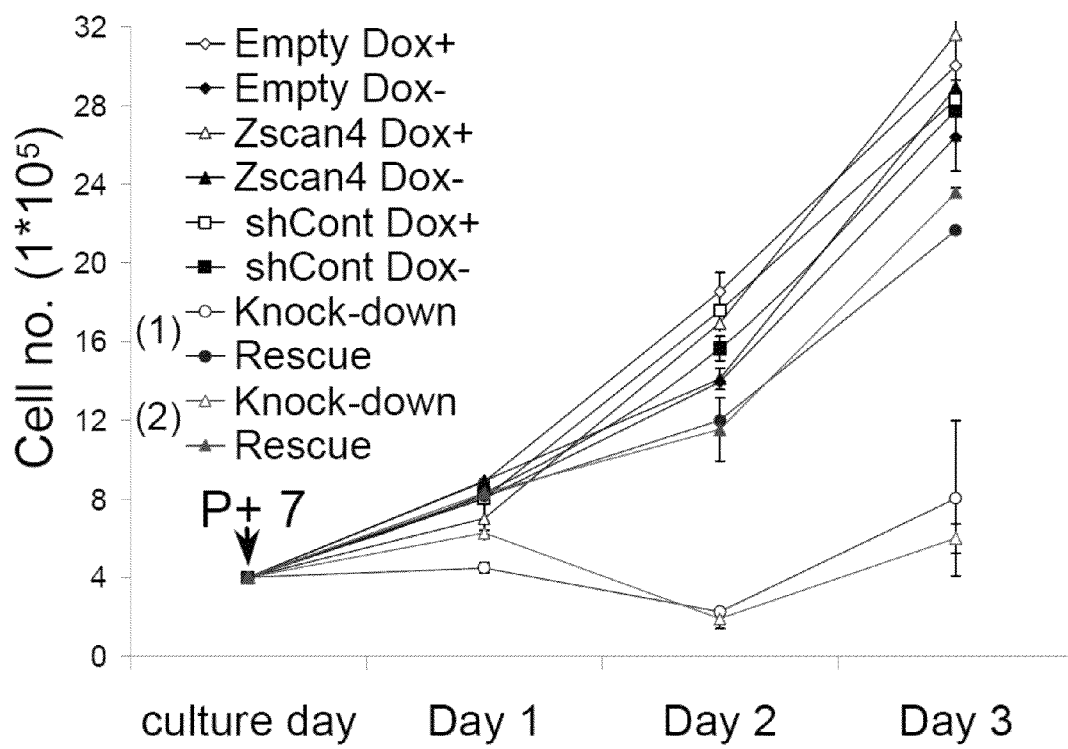
FIG. 4E is a graph showing reduced proliferation by Zscan4 knockdown at passage 7, prior to cell culture crisis (o, Δ), whereas rescue of Zscan4 improved proliferation rate (●, ▲). Controls included Tet-Empty cells in Dox+ (◇) and Dox− (◆); tet-Zscan4c cells in Dox+ (Δ) and Dox− (▲); and shCont cells in Dox+ (□) and Dox− (■). Assays were performed in biological triplicate in two independent experiments.

To investigate the event leading to cell culture crisis during passage 8, cell proliferation and apoptosis assays were performed at passage 7. The presence or absence of Dox alone did not affect the proliferation rate of the cells, as all the control cells, including tet-Empty cells, tet-Zscan4c cells, and shRNA control cells in Dox+ and Dox− conditions, showed normal proliferation curves (FIG. 4E). In contrast, a significant reduction in proliferation was observed in Zscan4-knockdown cell lines 1 and 2 in Dox+ conditions (FIG. 4E). A rescue experiment by induction of the exogenous copy of Zscan4c in Dox− condition was able to recover cell proliferation (FIG. 4E).

Figure 4F:
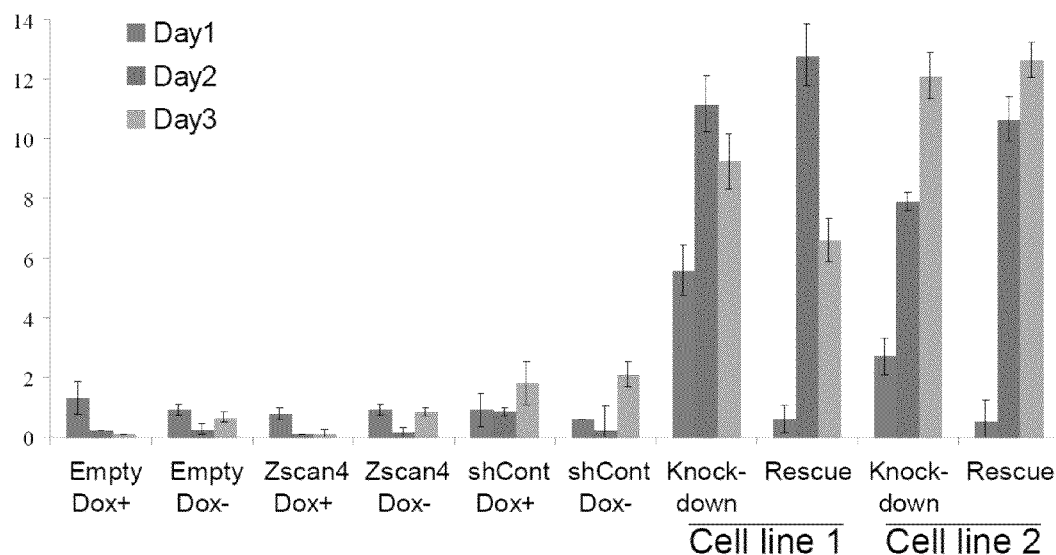
FIG. 4F is a graph showing increased apoptosis in Zscan4-knockdown cells. Apoptosis assay by Annexin-V was performed by FACS analysis. Controls included tet-Zscan4c cells (Zscan4) for basal apoptosis levels; shRNA control cells (shCont) for possible off-target effects; and tet-Empty cells (Empty) for doxycycline effect. Apoptotic cells were visualized by V-PE-conjugated Annexin-V antibody as well as the cell impermeant dye (7-AAD) as an indicator for dead cells. Dead cells were excluded to give the total number of apoptotic-live cells in culture.

Apoptosis and viability tests were further performed on Zscan4-knockdown cell lines at passage 7 and control cells daily for three days (FIG. 4F). Although the level of apoptosis in Zscan4-knockdown cells was higher than those (up to 2%) in all control cells (i.e., tet-Zscan4c parental cells, tet-Empty cells in Dox+ and Dox− conditions as well as shRNA control cells), it reached only up to 14%, suggesting that the significant reduction of cell numbers by Zscan4 knockdown is caused mostly by the reduction of cell proliferation, but not by the apoptosis. In addition, this moderate increase of apoptosis rate was not rescued by the induction of Zscan4c-ORF in the Dox− condition, suggesting that the increase in apoptosis rate was not a direct effect of Zscan4 knockdown.

Example 9

Karyotype Deterioration and Genomic Instability in Zscan4-Knockdown Cells

Zscan4-knockdown (cell line 2) and control cells were analyzed for karyotype at passage 3, the earliest passage expanded following clone isolation (FIG. 4G). In contrast to control cells (Dox+) with 82.5% normal karyotype, Zscan4-knockdown cells (Dox+) presented only 65% euploid or normal karyotype with multiple abnormalities including various types of chromosome fusions and fragmentations. Although this is still considered acceptable for cultured ES cells, it was apparent that the rescue cells (Dox−) showed better karyotype (75% normal). Control cells and parental cells kept under similar conditions did not exhibit similar abnormalities (FIG. 4G). Similar abnormalities were observed for the Zscan4-knockdown cell line 1 (Table 2), suggesting that genomic instability was not due to a specific clonal defect, but caused by Zscan4 knockdown. When cells were karyotyped at passage 10 after cell culture crisis, only 35% of the Zscan4-knockdown cells showed normal karyotype. Remarkably, rescue cells were significantly better, presenting 60% normal karyotype.

TABLE 2

Additional Data for Karyotype Analysis
Karyotype Analysis

| | Control Cells (Passage 10) | | | | Zscan4-knockdown cell line 1 (Passage 3) | | Zscan4-knockdown cell line 1 (Passage 10) | |
|---|---|---|---|---|---|---|---|---|
| | tet-Empty (Dox+) | tet-Empty (Dox−) | tet-Zscan4 (Dox+) | tet-Zscan4 (Dox−) | Zscan4 Knockdown | Zscan4 Rescue | Zscan4 Knockdown | Zscan4 Rescue |
| No. of metaphases examined | 58 | 57 | 55 | 61 | 40 | 40 | 40 | 40 |

TABLE 2-continued

Additional Data for Karyotype Analysis
Karyotype Analysis

|  | Control Cells (Passage 10) | | | | Zscan4-knockdown cell line 1 (Passage 3) | | Zscan4-knockdown cell line 1 (Passage 10) | |
| --- | --- | --- | --- | --- | --- | --- | --- | --- |
|  | tet-Empty (Dox+) | tet-Empty (Dox−) | tet-Zscan4 (Dox+) | tet-Zscan4 (Dox−) | Zscan4 Knockdown | Zscan4 Rescue | Zscan4 Knockdown | Zscan4 Rescue |
| No. of metaphases with abnormalities | 7 | 7 | 5 | 3 | 16 | 6 | 28 | 16 |
| Mean chromosome no./metaphase | 39.93 | 39.22 | 39.89 | 39.97 | 39.75 | 39.8 | 39.55 | 39.65 |
| % of cells with normal karyotype in culture | 87.9% | 87.7% | 90.9% | 95.1% | 60% | 75% | 30% | 60% |

Similar to the data for cell line 2 shown in FIG. 4G, at passage 3 the Zscan4-knockdown cells presented multiple karyotype abnormalities, such as fusions and fragmentations, whereas Zscan4-rescue cells had improved karyotype. The karyotype at passage 10 after cell crisis further deteriorated, whereas that of Zscan4-rescue cells was 60% normal. Parental tet-Zscan4 cells, used as control, showed a slight improvement of karyotype after Zscan4 induction (in Dox− condition), whereas tet-Empty control cells had similar results in both Dox+ and Dox− conditions.

Example 10

Abnormally Short Telomeres in Zscan4-Knockdown ES Cells

Figure 5A:
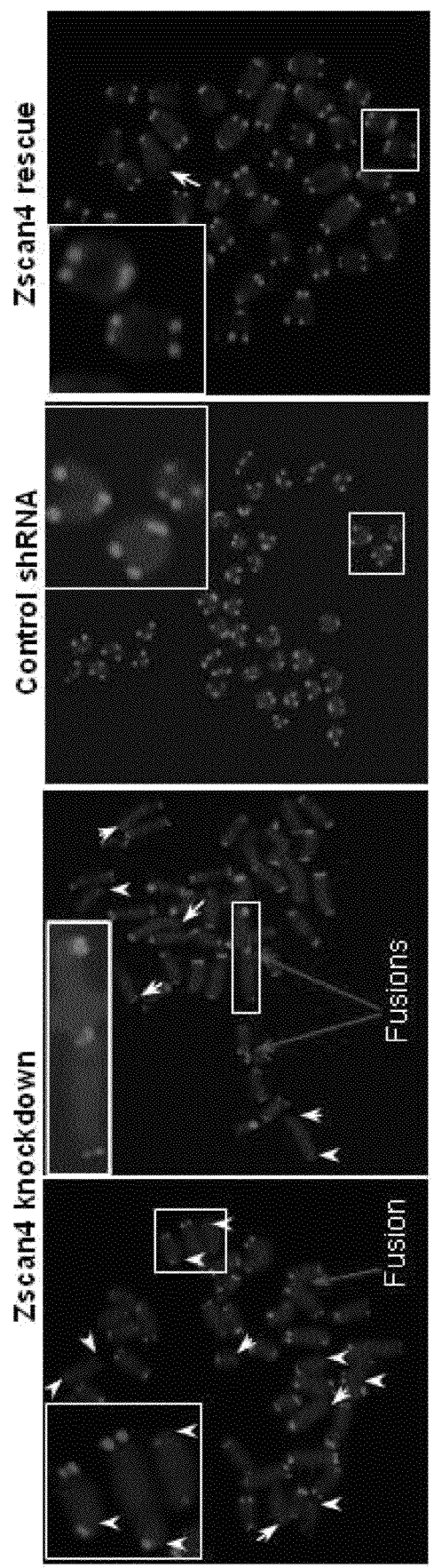
FIG. 5A is a series of images showing karyotype instability of Zscan4-knockdown cells. Shown are representative telomere FISH images in metaphase chromosome spreads stained by DAPI. Left two panels are images of Zscan4-knockdown cells. White arrows indicate missing or very short telomeres. Fusion indicates fused chromosomes. Right two panels are shRNA control cells with normal telomeres and Zscan4 rescue cells with improved telomere length and karyotype.
Figure 5B:
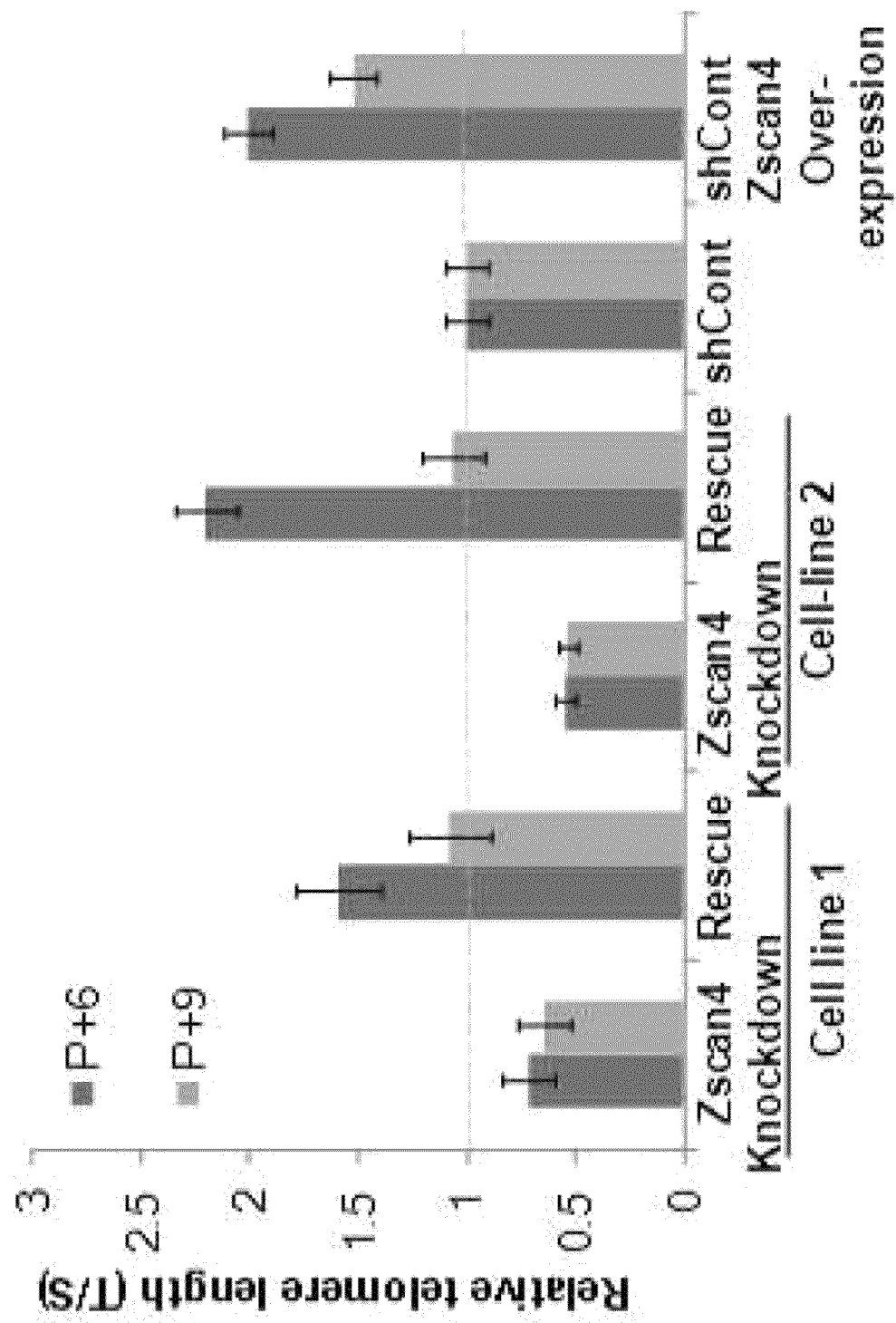
FIG. 5B is a graph showing relative telomere length ratio (T/S) measured by qPCR analysis of Zscan4-knockdown cells before (passage 6) and after (passage 9) of cell culture crisis. Relative telomere length ratio (T/S) was calculated by normalizing telomere length by a single copy gene. Error bars indicate S.E.M.

The compromised karyotype in Zscan4-knockdown cells prompted examination of their telomeres by telomere fluorescence in situ hybridization (FISH) (FIG. 5A) and telomere qPCR (FIG. 5B). For qPCR, telomere length ratios were compared to a single copy gene as previously described (Callicott and Womack, *Comp. Med.* 56:17-22, 2006; Cawthon, *Nucleic Acids Res.* 30: e47, 2002). Cells were collected in two different passages before and after cell crisis.

Remarkably, both telomere FISH and telomere qPCR showed a significant telomere shortening in both Zscan4-knockdown cell line 1 and 2. qPCR analysis showed that average telomere length decreased by 30±5% (mean±S.E.M.) in cell line 1 and 45±0.1% in cell line 2 at passage 6 (FIG. 5B). In contrast, the telomeres of shRNA control cells under the same conditions, as well as tet-Empty cells and the parental tet-Zscan4c cells in non-induced Dox+ conditions, remained intact with passages. qPCR data indicated that telomere shortening was rescued by Zscan4c over-expression (FIG. 5B), suggesting that knockdown of Zscan4 causes telomere shortening.

Telomere qPCR data were further validated by quantitative fluorescence in situ hybridization (Q-FISH) analysis (Poon et al., *Cytometry* 36:267-278, 1999). Telomeres were visualized by Cy3-conjugated probes (FIG. 5A) and the signal intensity was measured by the TFL-Telo software. Telomere length distribution diagram demonstrated that overall telomere lengths in the Zscan4-knockdown cells at passage 6 (FIG. 5C) were shorter than those in the control cells (FIG. 5E).

Figure 5C:
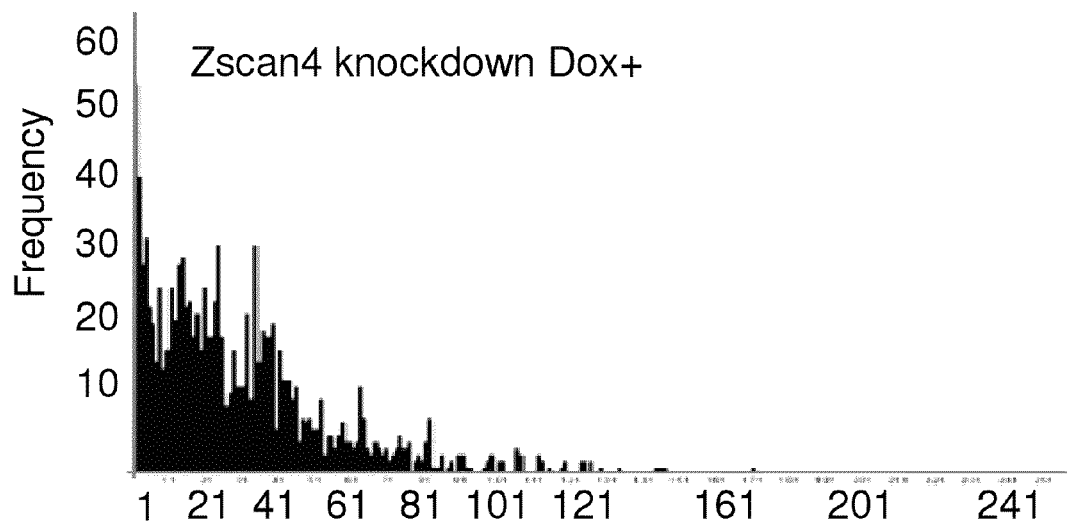
FIG. 5C is a pair of graphs showing Q-FISH, performed on Zscan4-knockdown cells, which confirmed a significant telomere shortening. A distribution diagram of relative telomere length is the result of analyzing 10 pooled nuclei (total of 1600 telomeres) by Q-FISH and TFL-Telo software. X-axis: Telomere fluorescence unit (1 TFU≈1 kb).
Figure 5C:
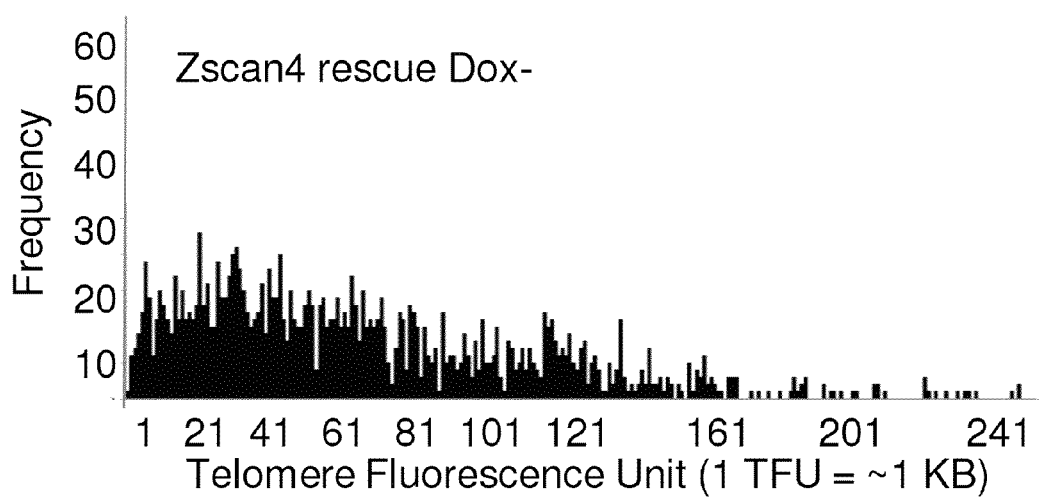

Surprisingly, telomeres were elongated in Zscan4-rescue cells by overexpressing Zscan4c; on average they were 1.7-fold longer than those in the normal cells and 2.4-fold longer than those in the knockdown cells (FIG. 5C). The distribution diagram for Zscan4-rescue cells also indicates that the average increase of telomere length was not due to abnormally long telomere, but due to an overall shift to the longer, yet normal spectrum of telomere length (FIG. 5C).

Example 11

Transient Expression of Zscan4 Extends Telomere Length in ES Cells

Figure 5D:
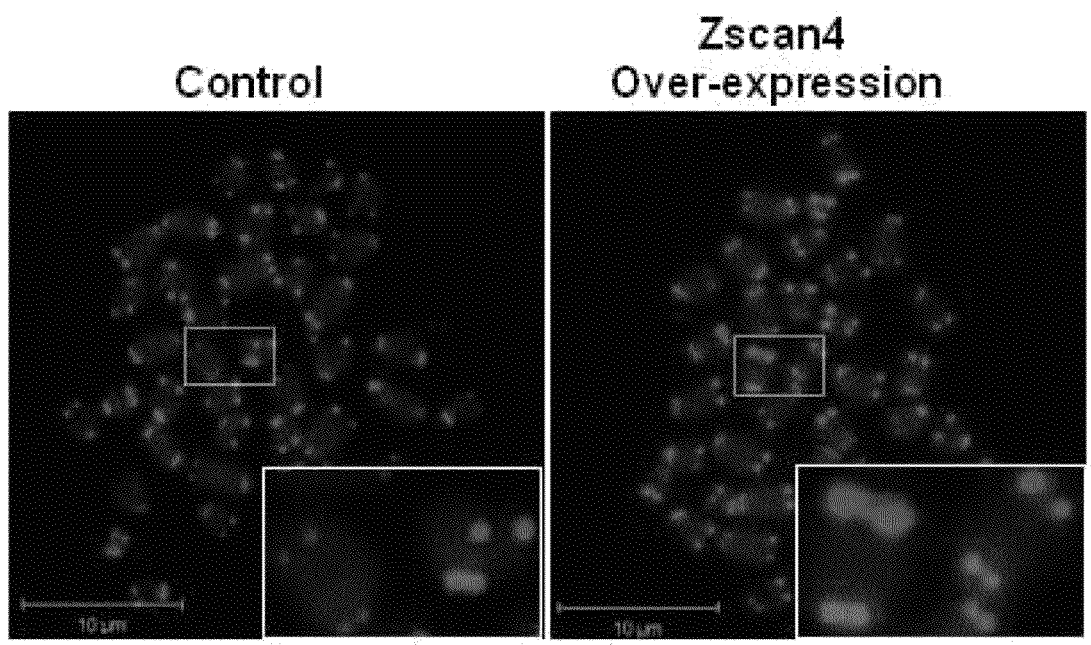
FIG. 5D is a pair of representative images of telomere FISH in Zscan4c-overexpressing cells: Cy3-conjugated PNA-telomere probes and DAPI.
Figure 5E:
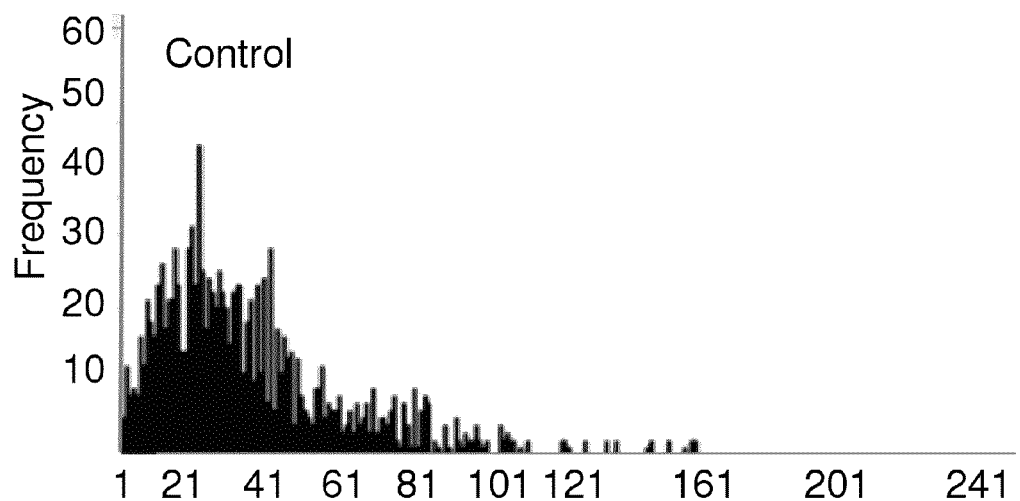
FIG. 5E is a pair of graphs showing a distribution of relative telomere length in Zscan4c-overexpressing cells.
Figure 5E:
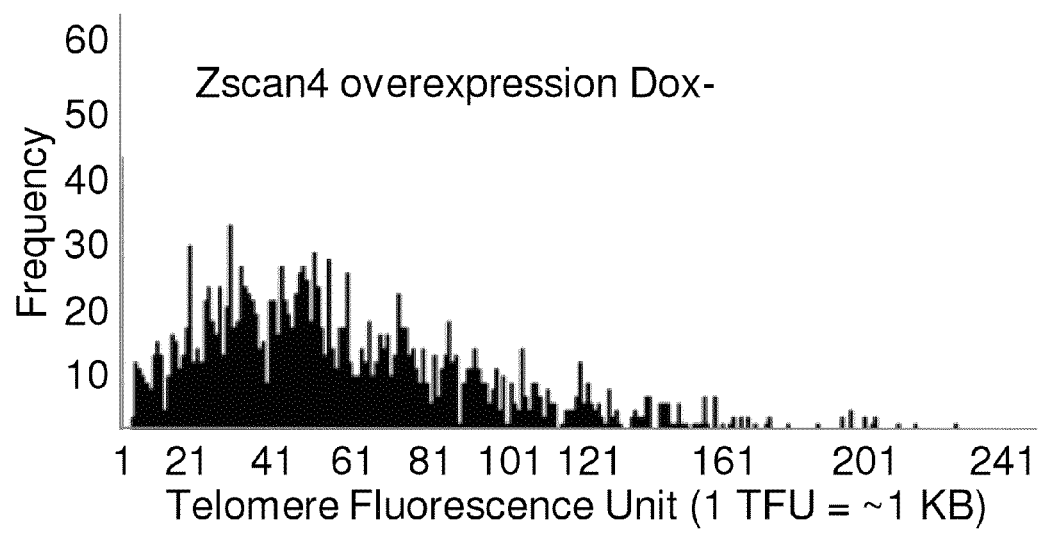

The effects of Zscan4 over-expression on telomeres was also examined in the parental tet-Zscan4c cells before and after gene induction (FIGS. 5D and 5E). Indeed, telomere Q-FISH results showed a significant increase (1.8-fold) in the average-telomere length from 39.4±0.13 kb (mean±S.E.M.) in the non-induced tet-Zscan4c cells to 65.9±0.2 kb in Zscan4 overexpressing cells (FIG. 5E). Consistent with the results of Zscan4 rescue shown in FIG. 5C, the telomere length distribution diagram indicated a shift to a longer but normal spectrum of telomere length (FIG. 5E).

Figure 5F:
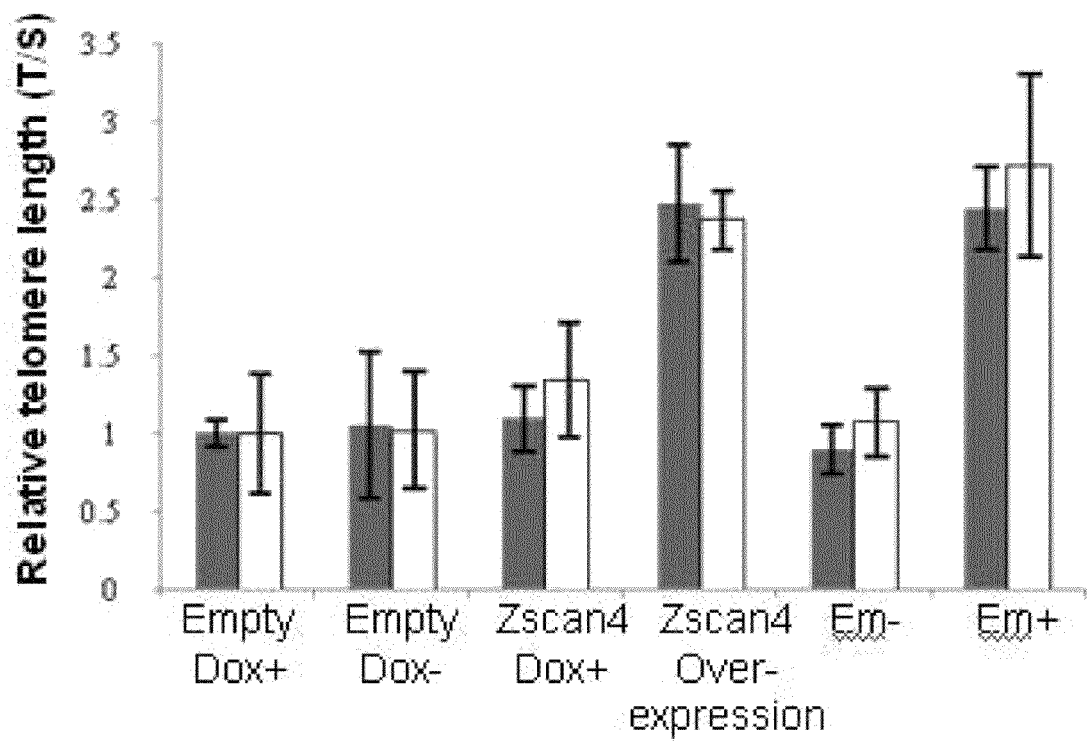
FIG. 5F is a graph showing relative telomere length ratio (T/S) measured by qPCR analysis of Zscan4c-overexpressing cells and FACS-sorted pZscan4-Emerald cells (Em+ and Em−). Error bars indicate S.E.M.

To verify Q-FISH results, telomeres were also measured by telomere qPCR. In accordance to Q-FISH results, the relative telomere length in tet-Zscan4c cells in Dox− condition was greater (2.47±0.38-fold) than that in non-induced Dox+ condition (FIG. 5F). As expected, this effect was not caused by the Dox itself, as control tet-Empty cells did not show a significant difference between Dox+ and Dox− conditions. Furthermore, telomere qPCR analysis was able to correlate telomere extension to the endogenous ES* state using FACS-sorted pZscan4-Emerald cells (FIG. 5F). The relative telomere length of Em(+) cells was 2.44±0.27-fold longer than control tet-Empty cells, whereas that of Em(−) cells was 0.89±0.15-fold shorter (FIG. 5F). Taken together, the telomere Q-FISH and qPCR data indicate that ES* state (i.e., Zscan4c expression) is associated with extended telomere length.

Figure 6A:
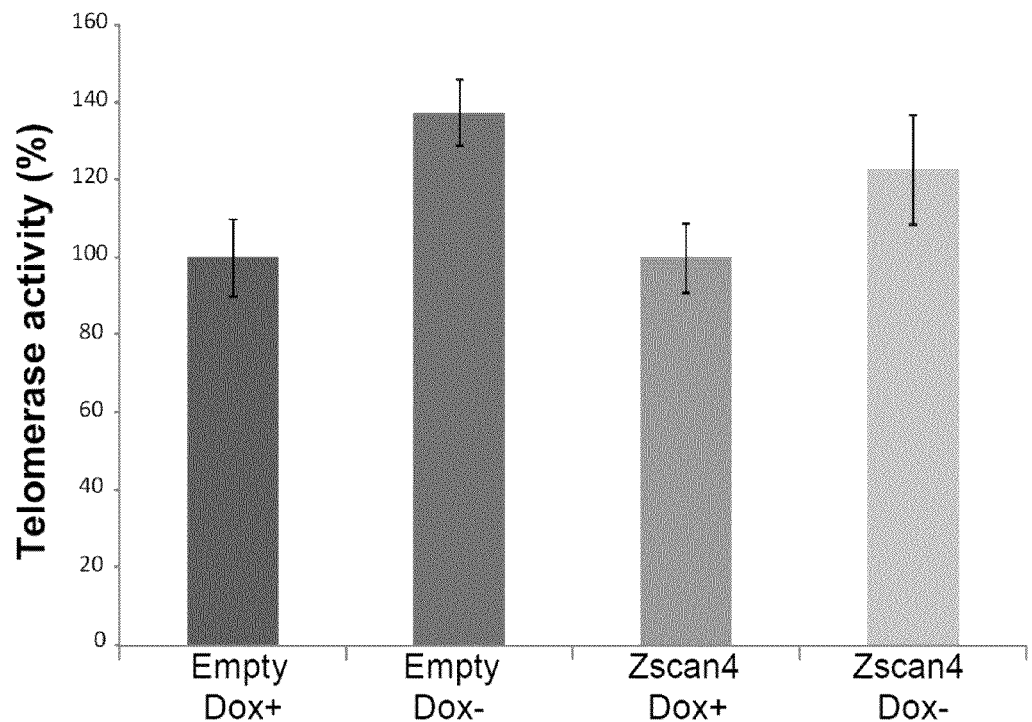
FIG. 6A is a graph showing telomerase activity measured by TRAP assay.

To test the possibility that telomere lengthening by Zscan4 is mediated by an increase in telomerase activity, Telomeric Repeat Amplification Protocol (TRAP) assay was conducted. TRAP assay demonstrated only a mild effect (30% higher) on telomerase activity in the induced Dox− tet-Zscan4c cells compared to non-induced Dox+ cells (FIG. 6A). However, tet-Empty cells also gave a similar mild response to Dox removal (FIG. 6A). Therefore, the slight increase of telomerase activity may be related to Dox removal, but not directly caused by Zscan4 induction. Furthermore, it is unlikely that the slight increase in telomerase activity could explain the rapid telomere elongation associated with Zscan4 over-expression.

Example 12

Figure 6B:
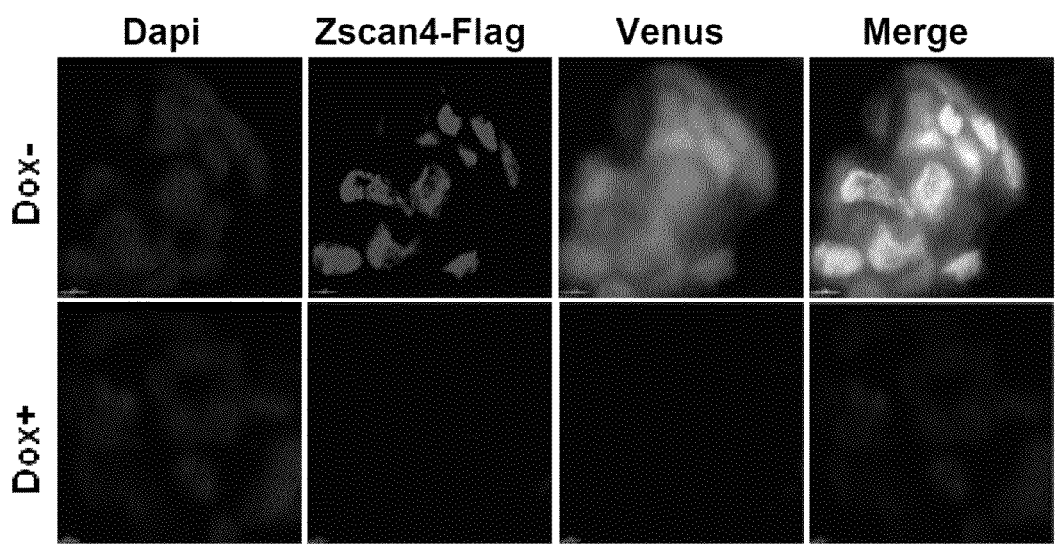
FIG. 6B is a series of representative images of tet-Zscan4c cells in Dox+ and Dox− conditions: ZSCAN4C-FLAG is visualized by Alexa546-conjugated antibody; Venus reporter; and all nuclei visualized by DAPI.

ZSCAN4 is Co-Localized with Meiosis-Specific Homologous Recombination Proteins on Telomeres The predicted structure of ZSCAN4 indicates the presence of SCAN domain as well as a DNA-binding domain indicating a role in recruitment of other proteins to chromatin. Indeed, immunostaining analysis showed nuclear localization of ZSCAN4C-FLAG after a 3-day induction by Dox removal (FIG. 6B). To determine whether ZSCAN4 protein is active on chromatin during the M phase, metaphase chromosome spreads of Zscan4-overexpressing cells before and after gene induction was assayed by immunostaining analysis (FIG. 6C). ZSCAN4C-FLAG was localized to the metaphase chromosomes; in particular, some of the chromosomes had more intense staining at both ends of chromosomes, suggesting more specific localization to telomeres of these chromosomes.

Figure 8A:
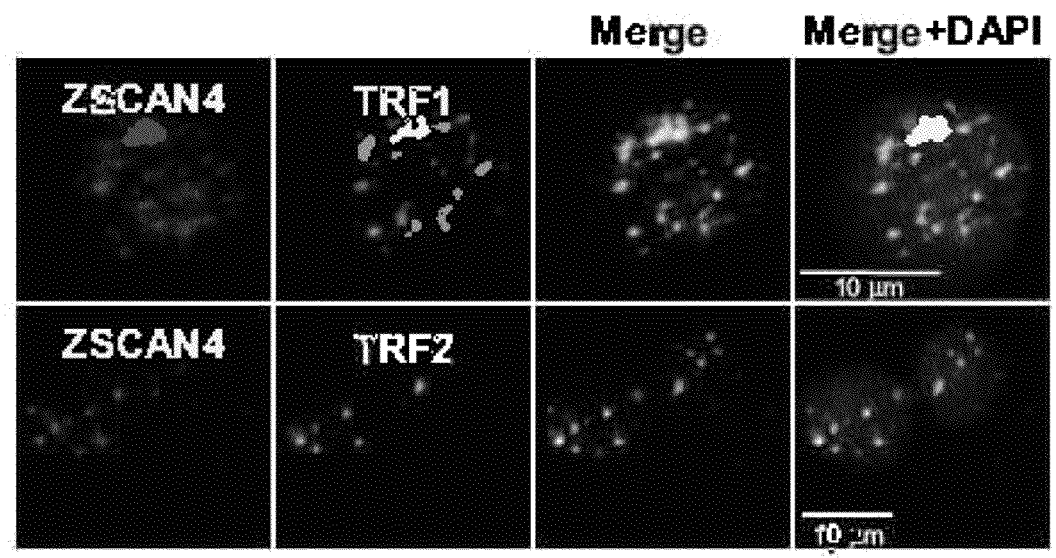
FIG. 8A is a series of images showing immunostaining and co-localization of ZSCAN4 with the telomere markers TRF1 (upper panel) and TRF2 (lower panel), as demonstrated by confocal microscopy. Nuclei are indicated by DAPI. Size bar=10 μm.
Figure 8B:
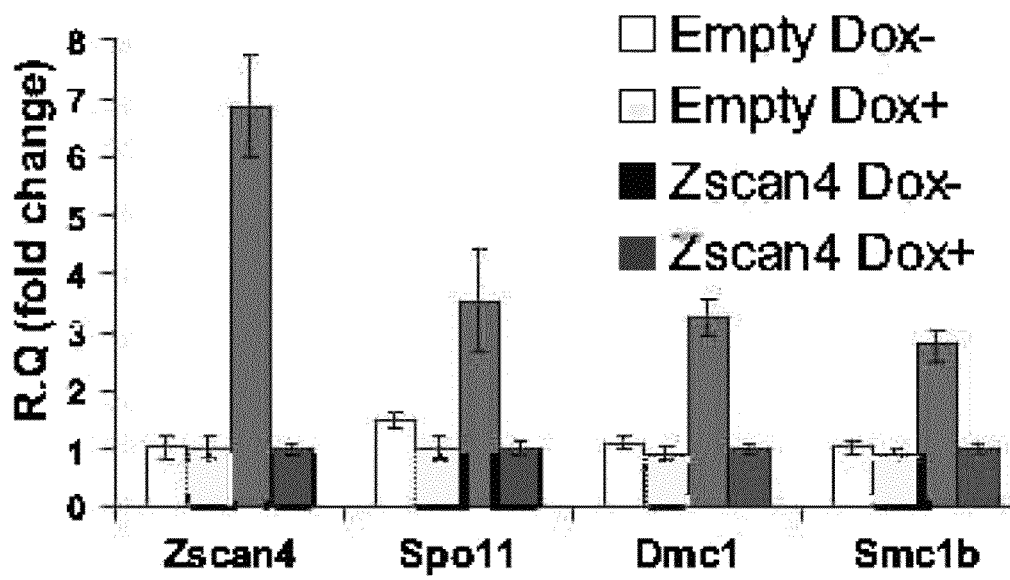
FIG. 8B is a graph showing the results of qPCR analysis, which confirmed Zscan4 induced the upregulation of meiosis-specific homologous recombination genes Spo11, Dmc1 and Smc1β.
Figure 8C:
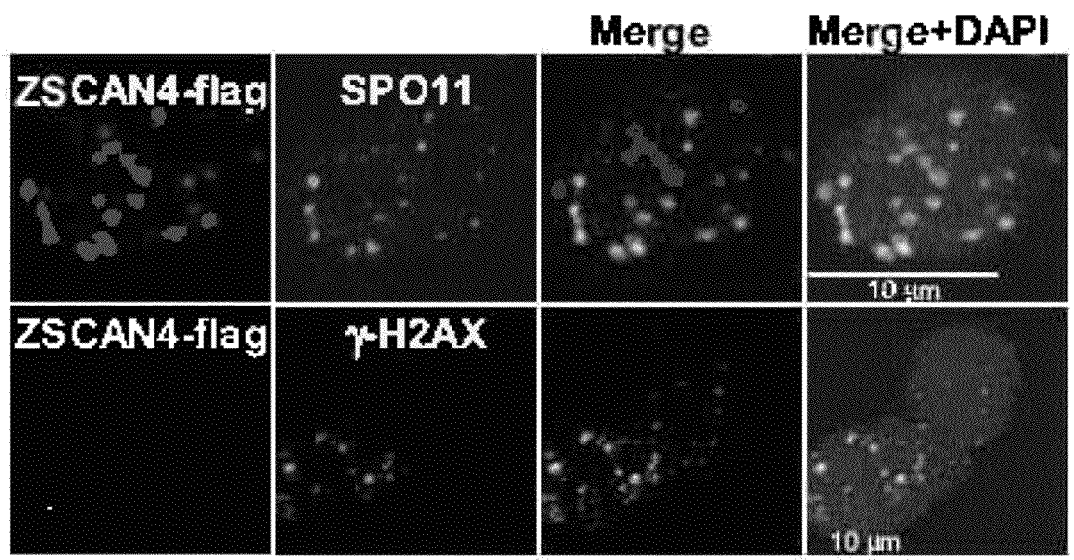
FIG. 8C is a series of images showing immunostaining analysis by confocal microscopy. ZSCAN4 foci co-localize with SPO11 (upper panel) and in most cells with γ-H2AX foci (lower panel).
Figure 8D:
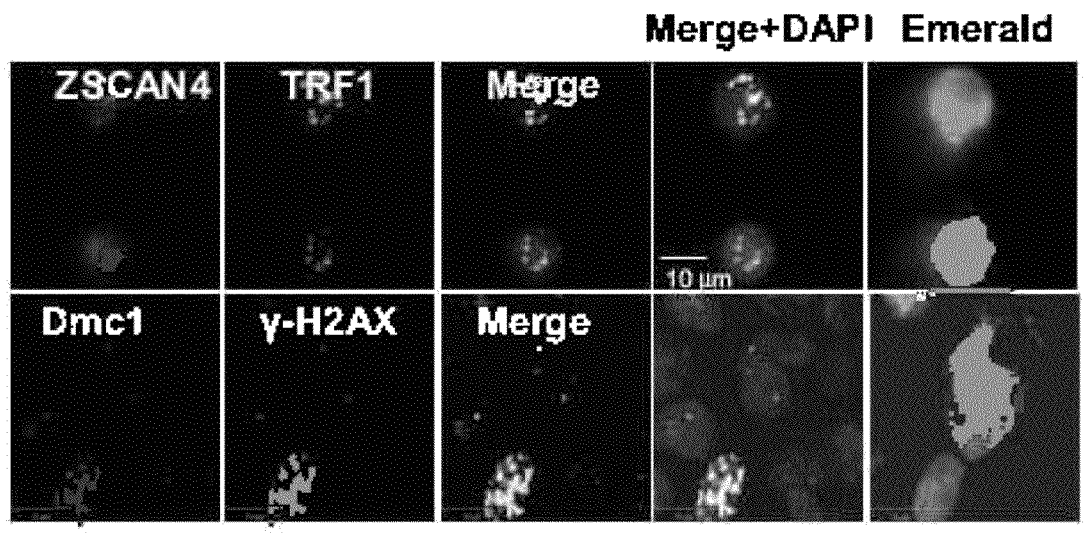
FIG. 8D is a series of images showing telomere localization of ZSCAN4 with TRF1 (upper panel) and DMC1/γ-H2AX foci (lower panel) in pZscan4-Emerald cells.

To test whether ZSCAN4 protein functions in telomere recombination, a co-localization study was performed for ZSCAN4 with telomere markers. Immunostaining analysis by confocal microscopy demonstrated ZSCAN4 foci were co-labeled on telomeres with TRF1 (Chong et al., *Science* 270:1663-7, 1995) and TRF2 (Opresko et al., *J. Biol. Chem.* 277:41110-9, 2002) (FIG. 8A). Additionally, microarray analysis indicated that meiosis-specific homologous recombination genes were induced by Zscan4c over-expression in ES cells. Analyses by qRT-PCR validated the results for the enzyme Spo11 (Keeney et al., *Cell* 88:375-84, 1997; Mahadevaiah et al., *Nat. Genet.* 27:271-6, 2001), which facilitates the double strand DNA breaks (DSBs) during meiotic recombination, the recombinase Dmc1 (Reinholdt et al., *Chromosoma* 114:127-34, 2005), required for DSBs repair, and the cohesion Smc1 (Revenkova et al., *Nat. Cell Biol.* 6:555-62, 2004) (FIG. 8B). Immunostaining showed SPO11 was co-localized with ZSCAN4 foci (FIG. 8C, upper panel), indicating SPO11 plays a role in induction of DSBs in telomeres to initiate T-SCEs. During meiotic recombination, DSBs are enclosed in γ-H2AX/ZSCAN4 foci forming after Zscan4c over-expression (FIG. 8C, lower panel). The RecA homolog DMC1 was further co-localized with TRF1 in Em+ cells (FIG. 8D, lower panel); moreover, ZSCAN4 foci were confirmed to be co-localized with TRF1 in Em+ cells (FIG. 8D, upper panel). Taken together, these results indicate that Zscan4 is involved in the induction and recruitment of the meiosis-specific homologous recombination machinery to telomeres.

Example 13

Zscan4 Over-Expression Promotes Telomere Recombination

A recent discovery has established that preimplantation embryos have the ability to activate rapid telomere extension, within 1 cell cycle, through telomere sister chromatid exchange (T-SCE) (Liu et al., *Nat. Cell Biol.* 9:1436-41, 2007). As Zscan 4 is a common marker for ES cells and 2-cell embryos, it was investigated whether the alternative lengthening of telomeres (ALT) is activated in ES* state by carrying out telomere chromosome-orientation FISH(CO-FISH) (Bailey et al., *Mutagenesis* 11:139-144, 1996) (FIG. 6D). The frequency of telomere recombination in the tet-Empty cells (control) was very low and showed no significant difference between Dox+ and Dox− conditions: 0.19±0.13 (Mean±S.E.M.). T-SCE events per nucleus were seen in Dox+ condition and 0.24±0.14 events per nucleus, in the Dox− condition (FIG. 6E). A similar frequency was observed for the non-induced tet-Zscan4c cells in the Dox+ condition: 0.26±0.15 T-SCE events/nucleus were found. In contrast, Zscan4c induction for 3 days resulted in >10-fold increase in T-SCE events: 76% of the nuclei showed 2.97±0.21 T-SCE events/nucleus (FIG. 6E). Therefore, the data clearly indicated that transient expression of Zscan4 promoted the telomere recombination.

Example 14

Increased Incidence of Sister Chromatid Exchange in Zscan4-Knockdown Cells

To further examine the genome instability of Zscan4-knockdown cells, a sister chromatid exchange (SCE) assay was performed. A significantly higher frequency of SCE events was found in Zscan4-knockdown cells (FIG. 7A). Tet-Empty cells as well as parental tet-Zscan4c cells were used as controls.

Consistent with previous reports on ES cells (Dronkert et al., *Mol. Cell. Biol.* 20:3147-56, 2000; Tateishi et al., *Mol. Cell. Biol.* 23:474-81, 2003), the basal SCE was relatively low in all control cells: tet-Empty cells had no significant difference by Dox removal with only 5.25±2.55 SCE events per SCE-positive nucleus (i.e., 13±1.4% of all cells analyzed) in Dox+ (FIGS. 7B and 7C) and 6.25±2.65 SCE events per SCE-positive nucleus (i.e., 12.7±3% of all cells analyzed) in the Dox− condition (FIGS. 7B and 7C). The basal SCE rate for the parental tet-Zscan4c cells in the Dox+ condition was slightly lower and only 8±2% of the nuclei had 4.75±1.26 SCE/positive nucleus. In contrast, 29±0.7% of Zscan4-knockdown cells had 11.27±4.2 SCE/positive nucleus (FIGS. 7B and 7C). When Zscan4 expression was rescued by the Dox− condition for 3 days, the number of spontaneous SCE was dramatically reduced. Only 13% of the metaphase spreads were SCE-positive (FIG. 7B) with a small number (2.86±2.1) of SCE per SCE-positive nucleus (FIG. 7C), which was comparable to the control cells.

Surprisingly, Zscan4c over-expression in parental tet-Zscan4c cells reduced SCE events dramatically and only 2±1.15% of the cells had just 2.25±1.5 SCE events/positive nucleus, which was 4-fold lower than that in the Dox+ condition and 6-fold lower than in the tet-Empty controls (FIGS. 7B and 7C). The data indicate that the expression of Zscan4 can decrease the incidence of SCE in ES cells, whereas knockdown increases genomic instability and SCE rate (FIG. 7D).

Taken together, these data provide multiple lines of evidence that Zscan4 is indispensable for long-term genomic stability, for example through mechanisms including the SCE rate as well as telomere regulation.

Example 15

Retinoic Acids Induce Transient Expression of Zscan4

This example describes the finding that retinoids (including vitamin A, 13-cis-retinoic acid, 9-cis-retinoic acid, and all-trans-retinoic acid) can transiently increase Zscan4+ cells in mouse ES cell culture.

Materials

A 20 mM stock solution of all-trans retinoic acid (atRA) in ethanol was used at a final concentration of 1 μM, 2 μM, or 50 nM. 9-cis RA and 13-cis RA were used at a final concentration of 1 μM final. Vitamin A (retinol) was used at a final concentration of 5 μM.

Results

Zscan4 Expression is Induced Transiently by all-Trans Retinoic Acid (atRA) Mouse ES cells (referred to as pZscan4-Emerald7 (MC1-ZE7) cells) in which a plasmid carrying a green fluorescent protein (Emerald: Em) regulated under the promoter of Zscan4c is integrated in the genome were used in these studies. The inventors' earlier work showed that the induction of Zscan4 expression can be monitored by the induction of Emerald fluorescence. Cells were first passaged to gelatin-coated plates in the presence of leukemia inhibitory factor (LIF+) and absence of atRA (atRA−). The next day (Day 0), the culture medium of each well was changed to four different conditions: LIF+ atRA−, LIF+ atRA+, LIF− atRA−, and LIF− atRA+. The final concentration of atRA was 2 M. The cells were maintained in the same culture medium for 8 days with medium changes every day, but without passaging. Cells were harvested every day and the number of Emerald GFP$^+$ cells was measured by flow cytometry (Guava).

Figure 9:
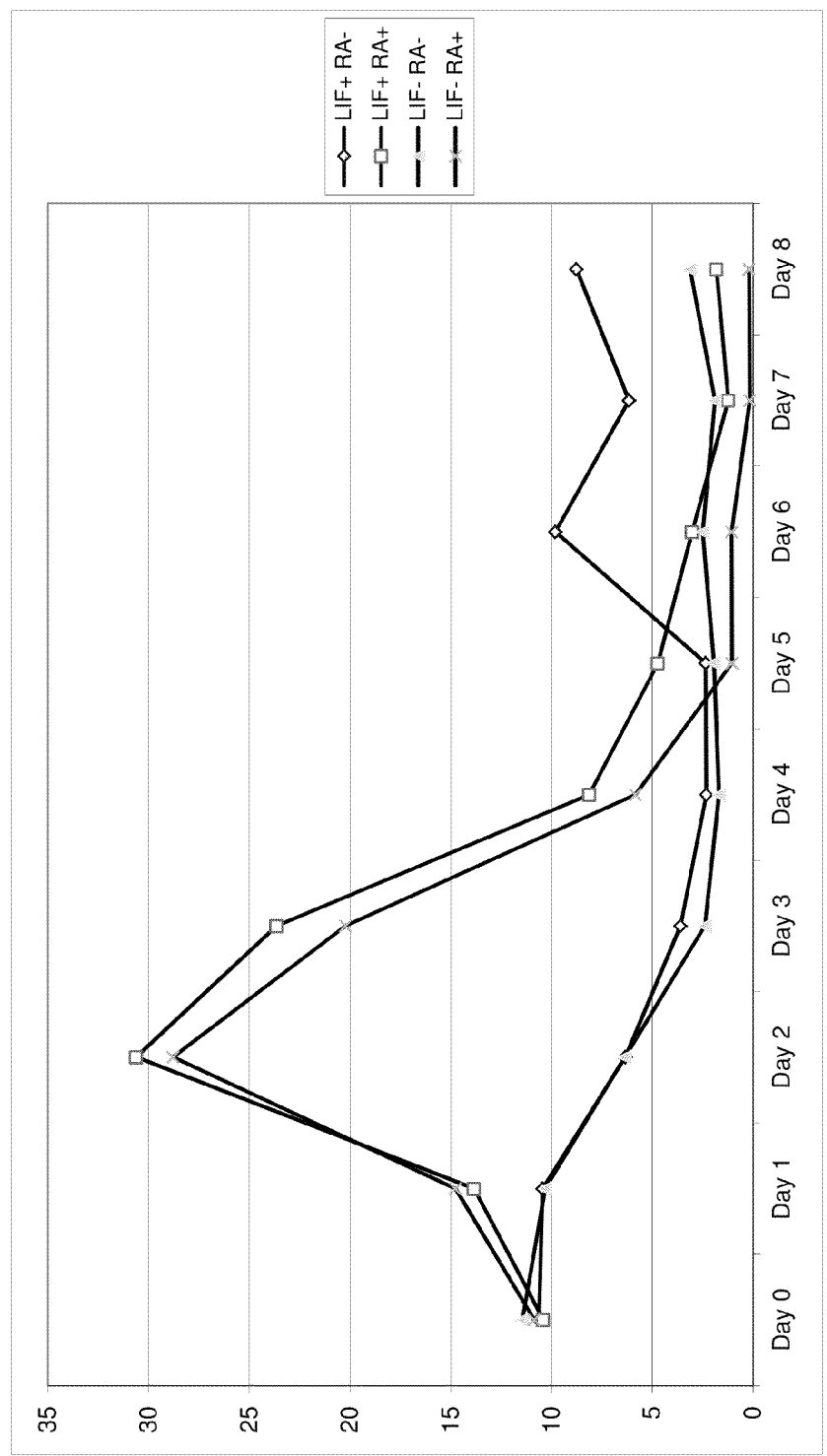
FIG. 9 is a line graph showing the percentage of Emerald cells following treatment of MC1-ZE7 cells in the presence or absence of leukemia inhibitory factor (LIF) and in the presence or absence of retinoic acid (RA). Cells were passaged to gelatin-coated plates in the presence of LIF (LIF+) and absence of atRA (atRA−). The next day (Day 0), the culture medium of each well was changed to four different conditions: LIF+ atRA−, LIF+ atRA+, LIF− atRA−, and LIF− atRA+. The cells were maintained in the same culture medium for 8 days with the medium changes every day, but without passaging. Cells were harvested every day and the number of Emerald GFP$^+$ cells was measured by flow cytometry.

The fraction of Em$^+$ cells (i.e., Zscan4$^+$ cells) in the culture was dramatically induced by atRA and peaked on the second day of atRA treatment (FIG. 9). However, this induction of Zscan4$^+$ cells was transient and declined to the basal level by the fourth day of atRA treatment. LIF is a well-established factor that can maintain ES cells in an undifferentiated state and is a part of the standard ES cell culture medium. The transient induction of Zscan4$^+$ cells by atRA was observed in both LIF+ and LIF− conditions.

Zscan4 Expression is Induced Transiently by Other Retinoids

Figure 10A:
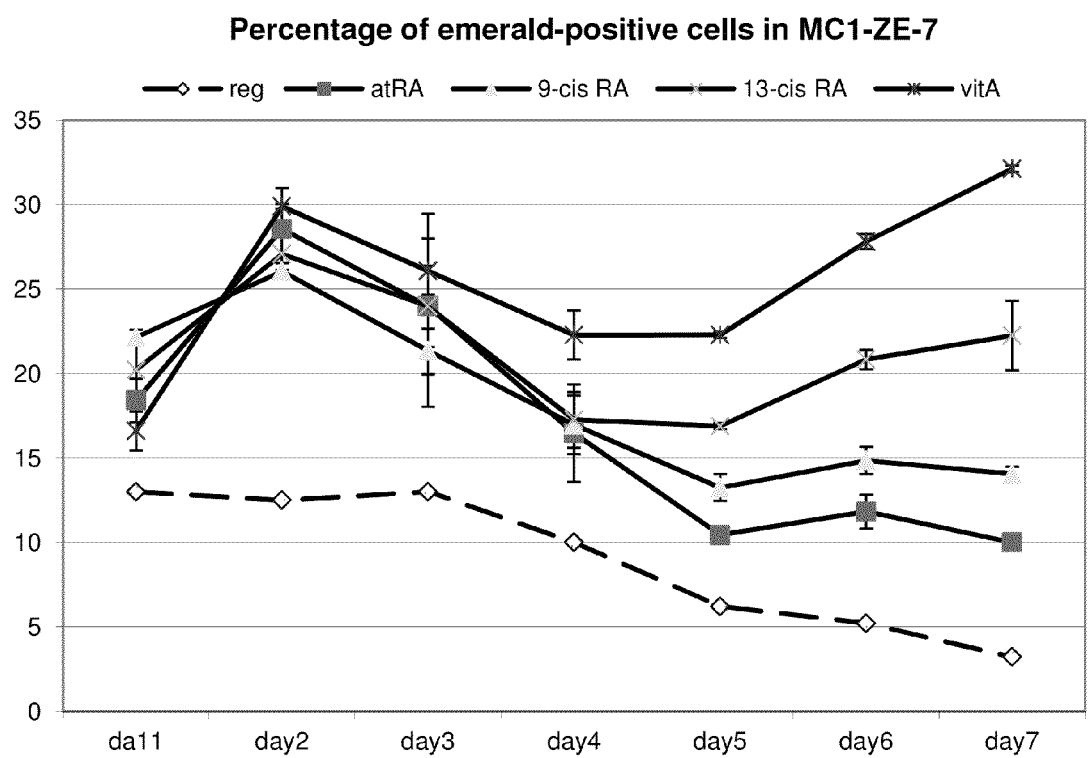
FIG. 10A is a line graph showing the effect of different retinoids (atRA, 9-cis RA, 13-cis RA or vitamin A) on the percentage of Zscan4$^+$ cells in culture. Shown is the percentage of Emerald$^+$ MC1-ZE-7 cells up to seven days following exposure to the retinoid.
Figure 10B:
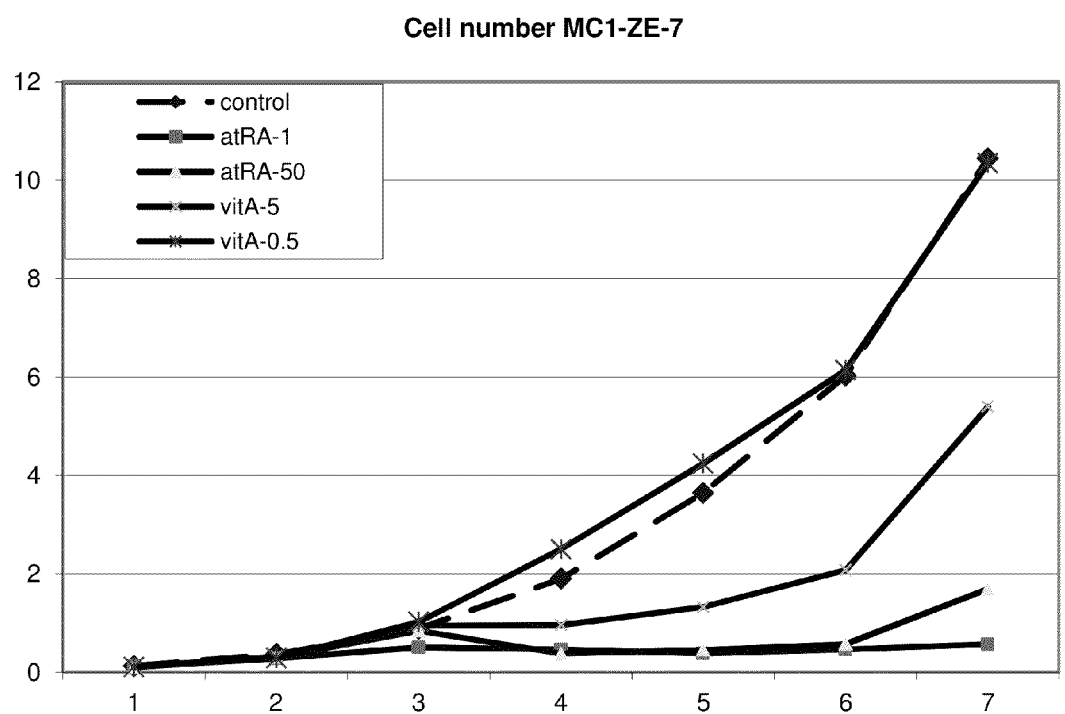
FIG. 10B is a line graph showing the effect of the different reintoids on ES cell proliferation.

Although atRA is most commonly used for mammalian cell culture systems, there are other retinoids that sometimes have similar activities on the cells. To test other retinoids for Zscan4-inducibility, similar time-course kinetic assays were carried out using atRA (50 nM final concentration), 9-cis RA (50 nM final concentration), 13-cis RA (50 nM final concentration), or vitamin A (5 μM final concentration). The fraction of Zscan4$^+$ cells was transiently increased and peaked on day 2 by each retinoid (FIG. 10A). However, within 7 days of treatment, the secondary increase of Zscan4$^+$ cells was observed for vitamin A and 13-cis RA, but not for atRA and 9-cis RA. This could be partially explained by differential effects of these retinoids on cell proliferation; vitamin A did not affect cell proliferation, 13-cis RA showed moderate suppression of cell proliferation, and both atRA and 9-cis RA induced nearly complete suppression of cell proliferation (FIG. 10B). Zscan4$^+$ cells may have growth advantages over Zscan4$^-$ cells in the presence of vitamin A and 13-cis RA.

These findings demonstrate that retinoids (including vitamin A, 13-cis-RA, 9-cis-RA, and atRA) can transiently increase Zscan4$^+$ cells in mouse ES cell culture.

Example 16

Oxidative Stress Induces Zscan4 Expression

This example describes the finding that expression of Zscan4 is increased in ES cells exposed to oxidative stress.

Figure 11:
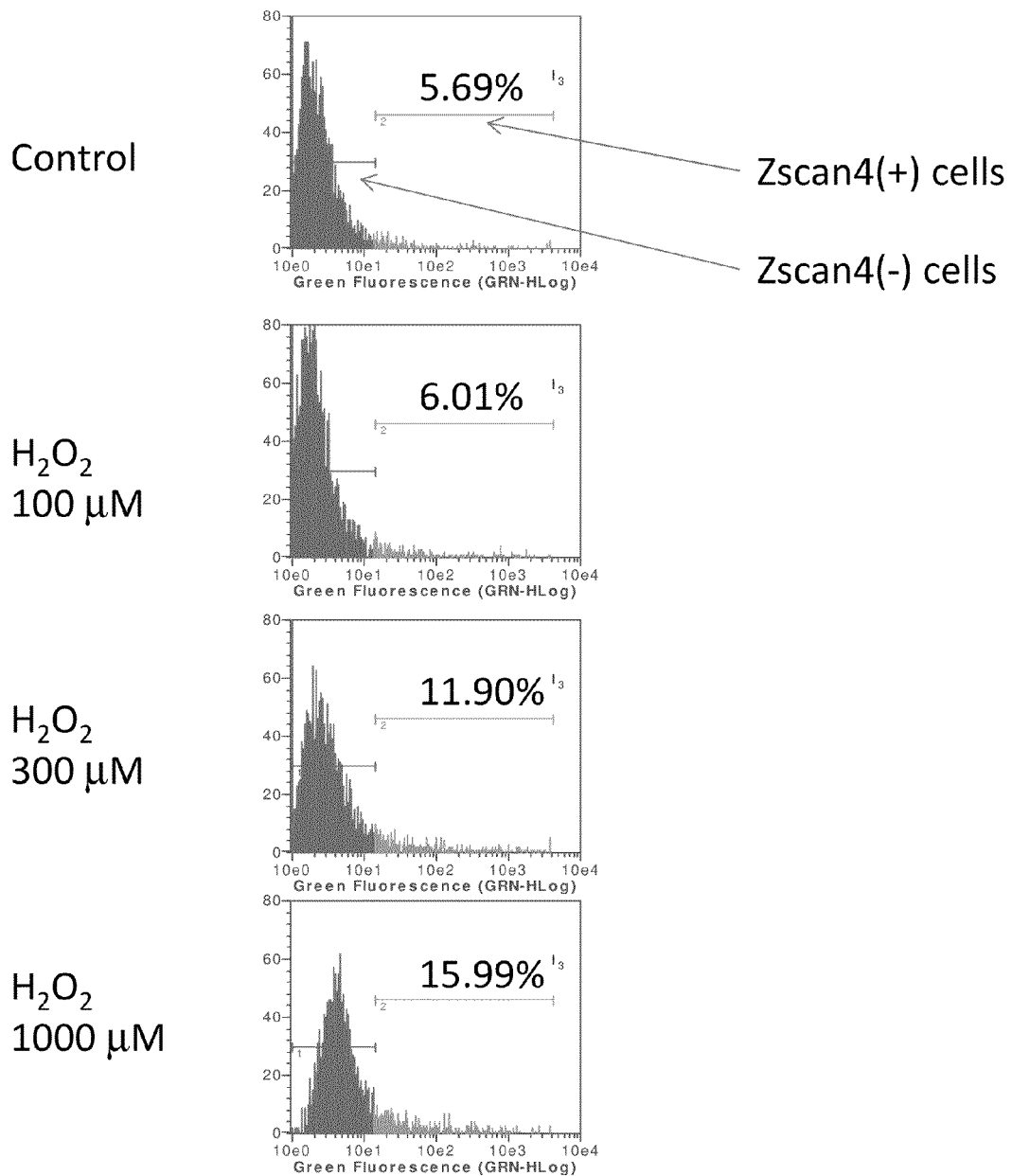
FIG. 11 is a series of flow cytometry plots showing induction of Zscan4 expression in response to oxidative stress. MC1-ZE7 cells were cultured in standard ES cell medium (LIF+). Hydrogen peroxide (H$_2$O$_2$) was added to the medium at a final concentration of 100 μM, 300 μM, or 1000 μM. The cells were cultured for two days and the fraction of Emerald$^+$ (i.e., Zscan4$^+$ cells) was measured by flow cytometry.

MC1-ZE7 cells were cultured in standard ES cell medium (LIF+). Hydrogen peroxide ($H_2O_2$) was added to the medium at a final concentration of 100 μM, 300 μM, or 1000 μM. The cells were cultured for two days and the percentage of Em$^+$ (i.e., Zscan4$^+$ cells) was determined by the Guava flow cytometry (Guava). The results demonstrate that oxidative stress (as induced by $H_2O_2$) increases the number of Zscan4$^+$ cells (FIG. 11).

Example 17

Zscan4 Protects ES Cells Against DNA-Damaging Agents

This example describes the finding that overexpression of Zscan4 in ES cells enhances survival of the cells following exposure to DNA-damaging agents, including mitomycin C (MMC) and cisplatin.

Control cells (carrying the tet-Empty plasmid) and Zscan4-expressing cells (carrying the tet-Zscan4 plasmid) were used in this study. The cells were cultured in standard ES medium (LIF+). Cells were passaged into two groups: (1) in the absence of doxycycline (Dox−), or (2) in the presence of doxycycline (Dox+) at a final concentration of 0.2 μg/ml. The Dox+ and Dox− media were changed every day. On the fourth day, the cells were cultured for 6 hours in the presence of MMC at a final concentration ranging from 0 to 600 ng/ml. The MMC was then removed from the culture by replacing the media. The cells were incubated for 3 more days in the Dox+ medium, and the medium was changed every day. Cells were harvested and the number of live cells was counted.

Figure 12B:
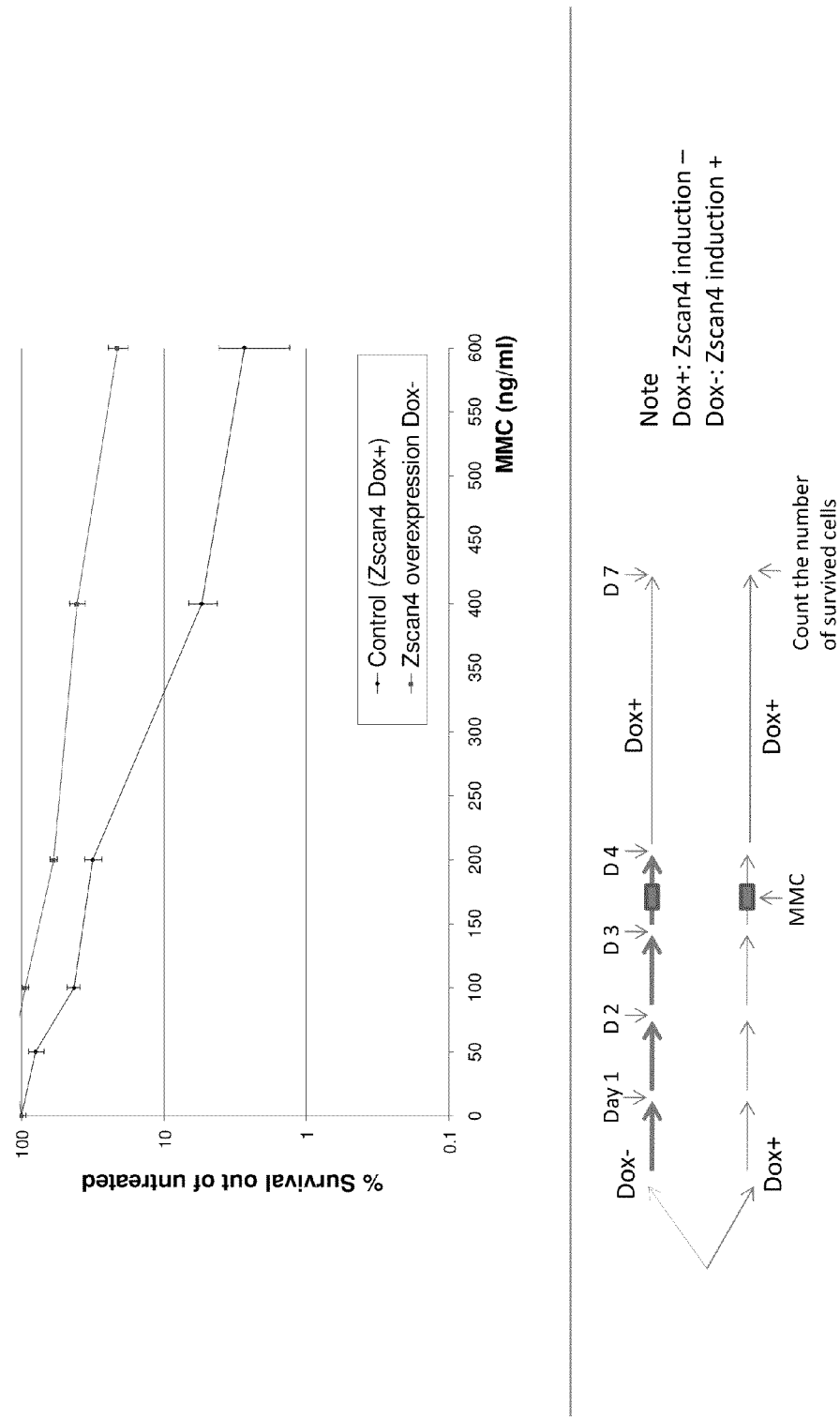

The results show that in control cells, the higher the dose of MMC, the lower the cell survival rate (FIG. 12A). However, there are no significant difference between Dox+ and Dox− conditions for control cells (in which Zscan4 expression is not induced). In contrast, there were significant difference between Dox+ and Dox− conditions in the Zscan4-expressing ES cells (FIG. 12B). These cells exhibited increased survival against the MMC treatment. These results indicate that Zscan4-overexpression protects ES cells from genotoxic assaults by DNA-damaging agents, such as MMC. Similar results were obtained with cisplatin.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

The invention claimed is:

1. A method for increasing genome stability of an isolated mouse induced pluripotent stem (iPS) cell; or increasing telomere length in an isolated mouse iPS cell; or both, comprising transfecting an isolated nucleic acid molecule encoding mouse Zscan4c into the iPS cell under conditions sufficient to allow for expression of mouse Zscan4c in the iPS cell.

2. The method of claim 1, wherein the isolated nucleic acid molecule comprises a vector.

3. The method of claim 2, wherein the vector is a viral vector.

4. The method of claim 2, wherein the vector is a plasmid vector.

5. The method of claim 2, wherein the vector encodes mouse Zscan4c operably linked to a promoter.

6. The method of claim 5, wherein the promoter is a constitutive promoter.

7. The method of claim 5, wherein the promoter is an inducible promoter.

8. The method of claim 1, wherein the nucleotide sequence of mouse Zscan4c is at least 95% identical to the nucleotide sequence of SEQ ID NO: 28.

9. The method of claim 1, wherein the nucleotide sequence of mouse Zscan4c comprises the nucleotide sequence of SEQ ID NO: 28.

10. The method of claim 1, wherein the nucleotide sequence of mouse Zscan4c consists of the nucleotide sequence of SEQ ID NO: 28.

11. The method of claim 1, wherein expression of mouse Zscan4c is transient.

12. The method of claim 1, wherein the isolated nucleic acid molecule encoding mouse Zscan4c is integrated into the genome of the iPS cell.

* * * * *